US008431604B2

(12) United States Patent
Netz et al.

(10) Patent No.: US 8,431,604 B2
(45) Date of Patent: Apr. 30, 2013

(54) GUANIDINE COMPOUNDS, AND USE THEREOF AS BINDING PARTNERS FOR 5-HT5 RECEPTORS

(75) Inventors: Astrid Netz, Mannheim (DE); Wilhelm Amberg, Mannheim (DE); Udo Lange, Mannheim (DE); Michael Ochse, Bad Duerkheim (DE); Charles W. Hutchins, Green Oaks, IL (US); Francisco-Xavier Garcia-Ladona, Kandel (DE); Wolfgang Wernet, Neustadt/Weinstrasse (DE); Andreas Kling, Mannheim (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 956 days.

(21) Appl. No.: 10/590,265

(22) PCT Filed: Feb. 15, 2005

(86) PCT No.: PCT/EP2005/001521
§ 371 (c)(1),
(2), (4) Date: Jun. 14, 2007

(87) PCT Pub. No.: WO2005/082871
PCT Pub. Date: Sep. 9, 2005

(65) Prior Publication Data
US 2007/0299074 A1 Dec. 27, 2007

(30) Foreign Application Priority Data
Feb. 19, 2004 (DE) .......................... 10 2004 008 141

(51) Int. Cl.
*A61K 31/155* (2006.01)
*A61K 31/421* (2006.01)
*A61P 19/02* (2006.01)
*C07D 263/30* (2006.01)
*C07D 277/20* (2006.01)

(52) U.S. Cl.
USPC ............ 514/370; 514/377; 548/190; 548/233

(58) Field of Classification Search ................... 514/370, 514/377; 548/190, 233
See application file for complete search history.

(56) References Cited

U.S. PATENT DOCUMENTS

| 3,562,258 | A | * | 2/1971 | Loop et al. | 548/233 |
| 4,089,965 | A | * | 5/1978 | Angier et al. | 514/370 |
| 4,355,004 | A | * | 10/1982 | Cantello et al. | 514/228.2 |
| 4,409,216 | A | * | 10/1983 | Cantello | 514/227.8 |
| 4,560,690 | A | | 12/1985 | Reiter | |
| 7,199,264 | B2 | | 4/2007 | Watanabe et al. | |
| 8,071,650 | B2 | | 12/2011 | Suh et al. | |
| 2008/0085900 | A1 | | 4/2008 | Gerlach et al. | |

FOREIGN PATENT DOCUMENTS

| EP | 0 259085 A1 | 3/1988 |
| EP | 0545376 A1 | 6/1993 |
| GB | I 031 165 A | 5/1966 |
| GB | 1409768 | * 10/1975 |
| GB | 1409768 A | 10/1975 |
| JP | 59-36674 | * 2/1984 |
| JP | 59 036674 A | 2/1984 |
| JP | 08 245621 A | 9/1996 |
| JP | 08337579 A | 12/1996 |
| JP | 09 040671 A | 2/1997 |
| WO | 92/16526 A1 | 10/1992 |
| WO | 95/18126 A1 | 7/1995 |
| WO | 96/05187 A1 | 2/1996 |
| WO | 98/47880 A1 | 10/1998 |
| WO | 99/20599 A | 4/1999 |
| WO | 02/16318 A | 2/2002 |
| WO | WO 02/16318 | * 2/2002 |
| WO | 02/30881 A1 | 4/2002 |
| WO | 02/36544 A | 5/2002 |
| WO | 03/050261 A2 | 6/2003 |
| WO | 03/105779 A2 | 12/2003 |

OTHER PUBLICATIONS

Registry No. 260443-24-1, entered into Registry file on Mar. 31, 2000.*
Registry No. 672884-90-1, entered into Registry file on Apr. 8, 2004.*
Chemical Abstracts, 101:7147, 1984.*
Bhargava, Prithwi N. et al., "Benzothiazolyl Guanidines as Antibacterials", Chemical Abstracts, 73:87831, 1970.*
Hogberg, Marita et al., "Bioisosteric Modificaton of PETT-HIV-1 RT-Inhibitors: Synthesis and Biological Evaluation", Bioorganic & Medicinal Chemistry Letters, 10(3), 265-268, 2000.*
LaMattina, John L. et al., "Antiulcer Agents. 4-Substituted 2-Guanidothiazoles: Reversible, Competitive, and Selective Inhibitors of Gastric H+, K+-ATPase", Journal of Medicinal Chemistry, 33, 543-552, 1990.*
Hogberg, et al., Bio. & Med. Chem. Lett., 10(3), 265-268, 2000.*
Hogberg, et al., Bioorganic and Medicinal Chemistry Letters, 10(3), 265-268, 2000.*

(Continued)

Primary Examiner — Susannah Chung
(74) Attorney, Agent, or Firm — Lisa V. Mueller; MIchael Best & Friedrich LLP

(57) ABSTRACT

The present invention relates to guanidine compounds of the general formula I

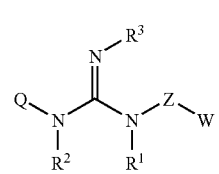

I corresponding enantiomeric, diastereomeric and/or tautomeric forms thereof as well as pharmaceutically acceptable salts thereof. The present compound further relates to the use of guanidine compounds as binding partners for 5-HT5 receptors for the treatment of diseases which are modulated by a 5-HT5 receptor activity, in particular for the treatment of neurodegenerative and neuropsychiatric disorders as well as the associated signs, symptoms and dysfunctions.

12 Claims, No Drawings

OTHER PUBLICATIONS

Katsura Yousuke. et al Anti-Helicobacter pylori Agents. 5. 2-(Substituted guanidino)-4-arylthiazoles and Aryloxazole Analogues Journal of Medicinal Chemistry, vol. 45, No. I (2002) pp. 143-150. (Abstract only).

Katsura Yousuke, et al Anti-Helicobacter pylori Agents. 4. 2-(Substituted guanidino)-4-phenylthiazoles and Some Structurally Rigid Derivatives Journal of Medicinal Chemistry vol. 43, No. 17 (2000) pp. 3315-3321. (Abstract only).

Hogberg Marita, et al Bioisosteric modification of PETT-HIV-I RT-inhibitors: synthesis and biological evaluation Bioorganic & Medicinal Chemistry Letter vol. 10, No. 3 (2000) pp. 265-268.

Katsura Yousuke, et al Anti-Helicobacter pylori agents. 3. 2-'(Arylalkyl)guanidino1-4-furylthiazoles Journal of Medicinal Chemistry vol. 42, No. 15 (1999) pp. 2920-2926. (Abstract only).

Gupta S., et al Superpendentic Index: A novel topological descriptor for predicting biological activity Journal of Chemical Information and Computer Sciences vol. 39, No. 2 (1999) pp. 272-77. (Abstract only).

Katsura Yosuke, et al Preparation of furylthiazoles as ulcer inhibitors Doc. No. XO002341494 CAPLUS Chemical Abstracts Service Columbus, OH Database Accession No. 1997: 195723; 126:212142t; Heterocyclic Compounds, vol. 126, No. 16, 1997, p. 583.

Katsura Yosuke, et al Preparation of guanidinothiazole derivatives as histamine H2 antagonists Doc. No. XP002341495 CAPLUS Chemical Abstracts Service Columbus, OH Database Accession No. 1997:140933; 126:157500f; Heterocyclic Compounds, vol. 126, No. 12, 1997, p. 589.

Kawanishi, Y., et al., "Synthesis and biological evaluation of a new reversely linked type of dual histamine H2 and gastrin receptor antagonist," Chemical & Pharmaceutical Bulletin vol. 45, No. 1(1997) pp. 116-124.

Preparation of 4-thienylthiazole derivatives as antiulcer and antibacterial agents Doc. No. XP002341497 CAPLUS Chemical Abstracts Service Columbus, OH Database Accession No. 1997:42; 126:47211e; Heterocyclic Compounds, vol. 126, No. 4, 1997, p. 580.

Goel Anshu, et al Structure-Activity Study on Antiulcer Agents Using Wiener's Topological Index and Molecular Connectivity Index Journal of Chemical Information and Computer Sciences vol. 35, No. 3 (1995) pp. 504-509. (Abstract only).

Buschauer, A., et al., "Synthesis and histamine H2-receptor antagonist activity of 4-(1-Pyrazoly1) butanamides, guanidinopyrazoles, and related compounds," Archiv Der Pharmazie, Jan. 1, 1995, pp. 349-358. (Abstract only).

* cited by examiner

GUANIDINE COMPOUNDS, AND USE THEREOF AS BINDING PARTNERS FOR 5-HT5 RECEPTORS

CROSS-REFERENCE TO RELATED APPLICATIONS

This application is a 371(c) National Stage application of international application no. PCT/EP2005/001521, filed Feb. 15, 2005, which claims priority of German application no. 10 2004 008 141.7 filed Feb. 19, 2004, the contents of which are incorporated herein by reference.

FIELD OF THE INVENTION

The present invention relates to guanidine compounds and the use of guanidine compounds as binding partners for 5-HT5 receptors for the treatment of diseases that are modulated by a 5-HT5 receptor activity, in particular for the treatment of neurodegenerative and neuropsychiatric disorders as well as the signs, symptoms and dysfunctions associated therewith.

BACKGROUND OF THE INVENTION

At least seven different receptor classes mediate the physiological activities which are attributed to an involvement of the neurotransmitter serotonin (5-hydroxytryptamine, or 5-HT for short). They are designated according to an internationally recognized classification as 5-HT1, 5-HT2, 5-HT3, 5-HT4, 5-HT5, 5-HT6 and 5-HT7. The majority of these classes additionally include further distinguishable receptor sub-types. For example, receptors belonging to the 5-HT1 class can be further subdivided in at least five sub-classes and are termed 5-HT1A, 5-HT1B, 5-HT1C 5-HT1D and 5-HT1E (Boess, Martin; Neuropharmacology 33:275-317 (1994).

The 5-HT5-class was first described by Plassat et al., The EMBO Journal Bd. 11 Nr. 13, S. 4779-4786 (1992). One distinguishes between 5-HT5A and 5-HT5B receptors (Erlander et al., Proc. Natl. Acad. Sci. USA 90:3452-3456 (1993). There exists only minimal sequence homology between 5-HT5 and other 5-HT receptors, and the pharmacological profile of these receptors is markedly different. 5-HT5 receptors can be localized with the help of molecular biological techniques in the olfactory bulb, in the hippocampus, in the cortex, in the cerebral ventricles, in the corpus callosum and in the cerebellum. It was shown by immunohistochemical methods that 5-HT5 receptors are expressed in different regions of the brain (Oliver et al. Brain Res 2000, 867, 131-142; Pasqualetti et al. Mol Brain Res 1998, 56, 1-8)). These 5-HT5 receptors can on the one hand modulate functions of the brain directly or indirectly, but on the other hand they may also participate in mechanisms involved in neuropathological, neurodegenerative and neuropsychiatric diseases. 5-HT5 receptors were also localized in astrocytes (Carson et al., GLIA 17:317-326 (1996). Astrocytes lie directly on the basal membrane of brain capillaries of the blood brain barrier and an abnormal astrocyte-endothelium-structure is associated with a loss of the blood brain barrier. The exact significance of astrocytes is unclear, but they seem to assume transport roles and connective functions. Reactive astrocytes were observed in connection with reactive gliosis in a series of pathological brain changes and neuropsychiatric diseases. These astrocytes modify their morphology as a result of brain injuries. The protein expression pattern changes and growth factors are produced. In-vitro studies on cultivated astrocytes showed 5-HT5 receptor mediated responses. For this reason, it is on the one hand assumed that the 5-HT5 receptor plays a role in recovery processes of the brain after disorders; on the other hand, it cannot be excluded that they contribute to the development of damage or even to an augmentation of damage.

Diseases of the CNS currently affect large sections of the population. The numbers of patients are continually rising, especially due to the increase of older people. Neuropathological conditions such as cerebral ischemia, stroke, epilepsy and seizures in general, chronic schizophrenia, other psychotic diseases, depression, states of anxiety, bipolar disorders, dementia, in particular Alzheimer dementia, demyelinizing diseases, in particular multiple sclerosis, and brain tumors, lead to damage of the brain and to the neuronal deficits associated therewith. Up to now, therapeutic treatments of the neurodegenerative and neuropsychiatric disorders described have been directed to different membrane receptors with the goal of compensating deficits in neurotransmission processes. Neuroprotective effects with different serotoninergic compounds have been achieved in animal models for neuropathological conditions such as ischemia, stroke and excitotoxicity; in some cases beneficial effects on mood disorders, such as depression or states of anxiety, could be observed. For example 5-HT1A agonists such as buspiron, or the compound 8-hydroxy-2-(di-n-propylamino)tetraline (8-OH-DPAT), characterized as a selective 5-HT1A receptor-ligand, are noteworthy in this regard. However, these agents alleviate the neurological deficits described only under certain conditions; an effective therapy for these diseases does not yet exist at the present time A further neuropathological disease effecting large segments of the population, is migraine. In most cases, migraine manifests itself in recurring headaches, affecting an estimated 8 million people, i.e. 3-5% of all children, 7% of all men and 14% of all women. Although a genetic predisposition is propagated, the causes seem to be complex. (Diener H. C. et al., Arzneimitteltherapie 15:387-394 (1997). Two hypotheses dominate. The vessel theory, known for a long time, suggests a dilation process of the inner and outer cerebral vessel system as a cause. The neurogenic theory is based on a release of vasoactive neurotransmitters, primarily neuropeptides, such as substance P and neurokinin from axons of the vasculature, as a result of a stimulation of certain ganglia which innervate brain tissue, which supposedly leads to inflammatory reactions and thus to pain.

A causal therapy for the treatment of migraines does not yet exist at the present time. Two different treatment methods are currently employed: a first, prophylactic therapy for the prevention of recurring migraine attacks and a second, symptomatic therapy for suppressing acute symptoms during attacks. Migraine-specific agents such as Sanmigran®, Nocerton®, Desernil® and Vidora®, as well as other agents typically used for other indications, such as beta-blockers, antiemetic agents such as Sibelium®, anti-depressives such as Laroxyl®, or anti-epileptic agents such as Depakin®, are prophylactically administered. In the context of acute therapy, one gives analgesics, such as Aspirin®, Paracetamol® or Optalidon®, non-steroidal anti-inflammatory agents, such as Cebutid®, Voltaren®, Brufen®, Ponstyl®, Profenid®, Apranx® and Naprosin® against the pain and inflammation, ergotalkaloids, such as ergotamine, dihydroergotamine, which can trigger a vasoconstriction, or substances of the triptan-family, such as sumatriptan, Naramig®, and AscoTop® with high affinity for 5-HT1D receptors. The latter substances function as agonists and block vasodilation.

The agents described are however not optimally suited for the treatment of migraines. Non-opioide analgesics often have side effects. The complex mode of action of ergotalkaloids leads to side effects such as hypertonia and gangrene due to the strong peripherla vasoconstriction. Compounds belonging to the triptan-family also are not completely satisfactory in their function. (Pfaffenrath V. Munch. Med. Wschr. 625-626 (1998).

The use of 5-HT5 receptor ligands in general for the treatment of migraines and other cerebralvascular diseases, is described in WO 00/041472, and in WO 00/041696 for the treatment of neurodegenerative and neuropsychiatric diseases.

Guanidine compounds have not been used as 5-HT5 ligands up to now.

Substituted guanidines are generally known as H2-antagonists, as inhibitors of the H+K+-ATPase, inhibitors of the secretion of stomach acid, and in these capacities as a means for treating PUD-syndrome (Peptic Ulcer Disease). The most diversely substituted thiazole-guanidines are generally described in the literature as compounds with anti-viral, bactericidal, anti-microbial and/or anti-inflammatory affect, as protease-inhibitors or vitronectin-antagonists.

WO-9911637 describes generally substituted N-{4-[anilinoalkyl)phenyl]-1,3-thiazole-2-yl}-N'-benzylguanidine and their use as protease-inhibitors. WO-9850373 describes N-substituted N-[4-(phenoxyphenyl)-1,3-thiazole-2-yl] guanidine and their use as bactericides. In WO-9605187 and EP-545376 the preparation of substituted 4-(3-aminomethylphenyl)-2-thiazolylguanidines and their use as H2 receptor antagonists is described. JP-59225172 generally describes N-alkyl-substituted 4-phenylthiazolguanidines as H1 and H2 receptor antagonists and their use as inhibitors of stomach acid secretion. NL-7700083, U.S. Pat. No. 4,089,965, DE-2700951, BE-850148 describe N-aryl-substituted 4-phenyl-thiazolguanidines with anti-viral properties, especially as anti-rhinovirus agents. EP-3640 generally describes substituted N-[4-(3-aminophenyl)-1,3-thiazole-2-yl]guanidines and their anitsecretory properties. JP-0817614 describes the preparation of 2-[(diaminomethylene)amino]-4-pyrimidinylthiazolguanidines with H2-antagonistic, anti-ulcer and anti-bacterial properties.

WO-9518126, JP-09040671, WO-9403450, WO-9303028, EP-355612, U.S. Pat. No. 4,814,341 describe N-substituted 4-furylthiazolguanidines with anti-bacterial properties (in particular *heliobacter pylori*) and their use for the treatment of gastritis and general PUD syndrome (ulcer, Zollinger-Ellison syndrome, oseophagititis, gastrointestinal bleeding). WO-9429304 and JP-08245621 describe corresponding 4-thienylthiazolguanidines with similar applications. WO-9216526, EP-417751 generally describe the preparation of N-substituted 4-hetaryl-substituted thiazolguanidines, especially corresponding pyridyl- and thiazolyl-derivatives, H2-antagonistic properties and their use as anti-ulcer- and anti-microbial agents. EP-259085 also describes the preparation of 4-hetaryl-substituted thiazolguanidines, especially corresponding pyrrolyl- and indolyl-derivatives for the treatment of PUD syndrome. JP-59225186 and JP-59036674 describe 4-hetaryl-substituted thiazolguanidines, especially 2-furyl- and 2-pyridyl-derivatives, and their anti-secretory properties.

WO-9324485, JP-07188197 describe 4-phenyloxazolguanidines as H2 receptor antagonists with additional anti-bacterial properties for the treatment of gastrointestinal diseases.

In the Journal of Chemical and Engineering Data 1978, 23 (2), 177-8, N-aryl-N''-2-(thiazolyl-, napthothiazolyl-, benzothiazolyl)guanidines are described as substances with antimalaria-effect and/or analgesic properties. In Bioorg. Med. Chem. Lett. 2000 (10), 265-268, N-[2-(2-methoxyphenyl)ethyl]-N'-1,3-thiazole-2-ylguanidine is described in the context of bioisosteric modifications of PETT-HIV-1 RT-inhibitors, but the compound did not show any demonstrable biological activity. Differently substituted thiazolguanidines are described in the following literature citations as antimicrobial substances with activity against *heliobacter pyloris*: 2-(substituted guanidino)-4-arylthiazole and Aryloxazole in J. Med. Chem. 2002, 45(1), 143-150; 2-(substituted guanidino)-4-phenylthiazole and rigidized derivatives in J. Med. Chem. 2000, 17, 3315-3321; 2-[(arylalkyl)guanidino]-4-furylthiazole in J. Med. Chem. 1999, 42(15), 2920-2926; alkylguanidino-4-furylthiazole in Bioorg. Med. Chem. Lett. 1998, 8(11), 1307-1312; 2-(alkylguanidino)-4-furylthiazole and analogs in J. Med. Chem. 1997, 40(16), 2462-2465. 4-substituted 2-guanidinothiazoles and 4-indolyl-2-guanidinothiazoles are described as inhibitors of the $H^+$, $K^+$-ATPase in J. Med. Chem. 1990, 33, 543-552; and THEOCHEM 2001, 539, 245-251; THEOCHEM 2002, 580, 263-270, respectively.

SUMMARY OF THE INVENTION

The aim of the present invention is to provide compounds enabling the treatment of neuropathological, neuropsychiatric and neurodegenerative disorders with sufficient efficacy and low side-effects.

It was surprisingly found that substances of the general formula I or IA function as ligands of the 5-HT5 receptors, and a treatment of the above-described disease states associated therewith, as well as the symptoms and dysfunctions associated therewith, is thereby made possible.

The present invention therefore relates to a guanidine compound of the general formula I

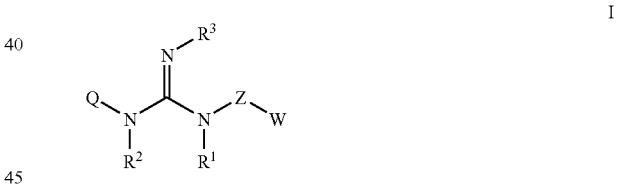

I corresponding enantiomeric, diastereomeric and/or tautomeric forms thereof, as well as pharmaceutically acceptable salts thereof, wherein the given moieties have the following definitions:

W:
a moiety of the general formula W1 or W2

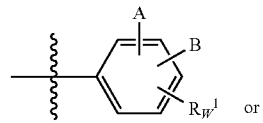

W1 or

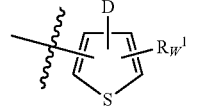

W2 wherein

A:
NO$_2$, NH$_2$, OH, CN, CF$_3$, OCF$_3$, CHF$_2$, OCHF$_2$, COOH, O—CH$_2$—COOH, halogen, SH, or each optionally substituted C$_1$-C$_6$-alkyl, C$_2$-C$_6$-alkenyl, C$_2$-C$_6$-alkynyl, C$_3$-C$_7$-cycloalkyl, C$_1$-C$_4$-alkylene-C$_3$-C$_7$-cycloalkyl, C$_1$-C$_4$-alkylene-heterocycloalkyl, aryl, hetaryl, heterocycloalkyl, C$_1$-C$_4$-alkylene-hetaryl or C$_1$-C$_4$-alkylene-aryl, or O—R$_A^1$, CO—R$_A^1$, S—R$_A^1$, SO—R$_A^1$, CO—O—R$_A^1$, NR$_A^4$—CO—O—R$_A^1$, O—CH$_2$—COO—R$_A^1$, NR$_A^2$R$_A^3$, CONH$_2$, SO$_2$NH$_2$, NR$_A^4$—CO—R$_A^1$, SO$_2$—R$_A^1$, NR$_A^4$—SO$_2$—R$_A^1$, SO$_2$—NR$_A^2$R$_A^3$ or CO—NR$_A^2$R$_A^3$;

R$_A^1$:
each optionally substituted C$_1$-C$_6$-alkyl, C$_2$-C$_6$-alkenyl, C$_2$-C$_6$-alkynyl, C$_3$-C$_7$-cycloalkyl, C$_1$-C$_4$-alkylene-C$_3$-C$_7$-cycloalkyl, C$_1$-C$_4$-alkylene-heterocycloalkyl, aryl, hetaryl, heterocycloalkyl, C$_1$-C$_4$-alkylene-aryl, C$_2$-C$_6$-alkenylene-aryl or C$_1$-C$_4$-alkylene-hetaryl;

R$_A^2$:
hydrogen, OH, CN, or
each optionally substituted C$_1$-C$_6$-alkyl, C$_2$-C$_6$-alkenyl, C$_2$-C$_6$-alkynyl, C$_1$-C$_4$-alkylene-C$_3$-C$_7$-cycloalkyl, C$_1$-C$_4$-alkylene-heterocycloalkyl, aryl, hetaryl, heterocycloalkyl, C$_1$-C$_4$-alkylene-aryl, C1-C$_4$-alkylene-hetaryl, C$_1$-C$_6$-alkylene-O—C$_1$-C$_6$-alkyl, CO—C$_1$-C$_6$-alkyl, CO-aryl, CO-hetaryl, CO—C$_1$-C$_4$-alkylene-aryl, CO—C$_1$-C$_4$-alkylene-hetaryl, CO—O—C$_1$-C$_6$-alkyl, CO—O-aryl, CO—O—C$_1$-C$_4$-alkylene-aryl, CO—O-hetaryl, CO—O—C$_1$-C$_4$-alkylene-hetaryl, SO$_2$—C$_1$-C$_6$-alkyl, SO$_2$-aryl, SO$_2$-hetaryl, SO$_2$—C$_1$-C$_4$-alkylene-aryl or SO$_2$—C$_1$-C$_4$-alkylene-hetaryl;

R$_A^3$:
each optionally substituted C$_1$-C$_6$-alkyl, C$_2$-C$_6$-alkenyl, C$_2$-C$_6$-alkynyl, C$_1$-C$_4$-alkylene-C$_3$-C$_7$-cycloalkyl, C$_1$-C$_4$-alkylene-heterocycloalkyl, aryl, hetaryl, heterocycloalkyl, C$_1$-C$_4$-alkylene-aryl, C$_1$-C$_4$-alkylene-hetaryl, C$_1$-C$_6$-alkylene-O—C$_1$-C$_6$-alkyl, CO—C$_1$-C$_6$-alkyl, CO-aryl, CO-hetaryl, CO—C$_1$-C$_4$-alkylene-aryl, CO—C$_1$-C$_4$-alkylene-hetaryl, CO—O—C$_1$-C$_6$-alkyl, CO—O-aryl, CO—O—C$_1$-C$_4$-alkylene-aryl, CO—O-hetaryl, CO—O—C$_1$-C$_4$-alkylene-hetaryl, SO$_2$—C$_1$-C$_6$-alkyl, SO$_2$-aryl, SO$_2$-hetaryl, SO$_2$—C$_1$-C$_4$-alkylene-aryl or SO$_2$—C$_1$-C$_4$-alkylene-hetaryl;

or the moieties R$_A^2$ and R$_A^3$ form, together with the nitrogen, a 3 to 7-membered, optionally substituted, saturated or aromatic heterocycle, which may contain one, two or three further different or identical heteroatoms from the group O, N, S; wherein optionally two substituted moieties on this heterocycle can together form an anellated, saturated, unsaturated or aromatic carbocycle or heterocycle, wherein the heterocycle can contain up to three different or identical heteroatoms O, N, S, and wherein the so formed cycle can optionally be substituted or a further, optionally substituted cycle can be condensed onto this cycle;

R$_A^4$:
hydrogen, or
each optionally substituted C$_1$-C$_6$-alkyl, C$_1$-C$_5$-alkylene-O—C$_1$-C$_6$-alkyl, C$_2$-C$_6$-alkenyl, C$_3$-C$_{12}$-alkynyl, CO—C$_1$-C$_6$-alkyl, CO—O—C$_1$-C$_6$-alkyl, SO$_2$—C$_1$-C$_6$-alkyl, C$_3$-C$_7$-cycloalkyl, aryl, C$_1$-C$_4$-alkylene-aryl, CO—O-arylalkyl, CO—C$_1$-C$_4$-alkylene-aryl, CO-aryl, SO$_2$-aryl, hetaryl, CO-hetaryl or SO$_2$—C$_1$-C$_4$-alkylene-aryl;

B:
hydrogen or as moiety A is defined,
or each independently of one another, two of the moieties A, B or R$_W^1$ together form a 3 to 7-membered, optionally substituted, saturated or unsaturated carbocycle or an optionally substituted, saturated or unsaturated or aromatic heterocycle which may contain one, two or three further different or identical heteroatoms from the group O, N, S; wherein optionally two moieties substituted on this carbo- or heterocycle may together form an anellated, saturated, unsaturated or aromatic carbocycle or heterocycle, wherein the heterocycle may contain up to three different or identical heteroatoms O, N, S, and wherein the formed cycle can optionally be substituted or a further, optionally substituted cycle can be condensed onto this cycle;

R$_W^1$:
hydrogen, OH, halogen, NO$_2$, NH$_2$, CN, CF$_3$, CHF$_2$, O—CF$_3$, O—CHF$_2$, or
each optionally substituted C$_1$-C$_6$-alkyl, C$_3$-C$_7$-cycloalkyl, C$_1$-C$_6$-alkylene-O—C$_1$-C$_6$-alkyl, C$_1$-C$_6$-thioalkyl, aryl, hetaryl, O—C$_1$-C$_6$-alkyl, O-aryl, O-benzyl, C$_1$-C$_6$-alkylamino, C$_1$-C$_6$-dialkylamino, pyrrolidinyl, piperidinyl, morpholinyl, CO—C$_1$-C$_6$-alkyl, SO$_2$—C$_1$-C$_6$-alkyl, CO-aryl, SO$_2$-aryl, CO—C$_1$-C$_4$-alkylene-aryl, SO$_2$—C$_1$-C$_4$-alkylene-aryl, SO-aryl, CONH$_2$, CONH—C$_1$-C$_6$-alkyl, SO$_2$NH—C$_1$-C$_6$-alkyl, CON—(C$_1$-C$_6$-alkyl)$_2$, SO$_2$N—(C$_1$-C$_6$-alkyl)$_2$, NH—SO$_2$—C$_1$-C$_6$-alkyl or NH—CO—C$_1$-C$_6$-alkyl;

D:
as moiety A is defined;

Z:
a moiety of the general formula Z1

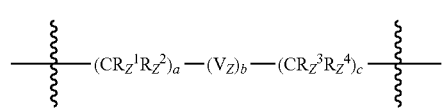

with the indices
a=0-4
b=0, 1
c=0-4
wherein the sum of a, b and c is at least 1 and no more than 5;

R$_Z^1$, R$_Z^2$, R$_Z^3$, R$_Z^4$ independently of one another:
hydrogen, halogen, OH, or
each optionally substituted C$_1$-C$_6$-alkyl, C$_2$-C$_6$-alkenyl, C$_2$-C$_6$-alkynyl, C$_1$-C$_6$-alkylene-C$_3$-C$_7$-cycloalkyl, C$_3$-C$_7$-cycloalkyl, aryl, C$_1$-C$_4$-alkylene-aryl, hetaryl or C$_1$-C$_4$-alkylene-hetaryl, or
each independently of one another, two moieties are R$_Z^1$ and R$_Z^2$ or R$_Z^3$ and R$_Z^4$ together form a 3 to 7-membered, optionally substituted, saturated or unsaturated carbo- or heterocycle, wherein the heterocycle can contain up to three heteroatoms from the group O, N or S;

V$_Z$:
—CO—, —CO—NR$_Z^5$—, —NR$_Z^5$—CO—, —O—, —S—, —SO—, —SO$_2$—, —SO$_2$—NR$_Z^5$—,

—NR$_z^5$—SO$_2$—, —CS—, —CS—NR$_z^5$—,
—NR$_z^5$—CS—, —CS—O—, —O—CS—, —CO—
O—, —O—CO—, —O—, ethynylene,
—C(=CR$_z^5$R$_z^7$)—, —CR$_z^6$=CR$_z^7$—, —NR$_z^5$—
CO—NR$_z^5$*—, —O—CO—NR$_z^5$—, —NR$_z^5$—;

R$_z^5$, R$_z^5$* independently of one another:
  hydrogen or
  each optionally substituted C$_1$-C$_6$-alkyl, C$_1$-C$_6$-alkylene-O—C$_1$-C$_6$-alkyl, C$_2$-C$_6$-alkenyl, C$_3$-C$_{12}$-alkynyl, CO—C$_1$-C$_6$-alkyl, CO—O—C$_1$-C$_6$-alkyl, SO$_2$—C$_1$-C$_6$-alkyl, C$_3$-C$_7$-cycloalkyl, aryl, C$_1$-C$_4$-alkylene-aryl, CO—O—C$_1$-C$_4$-alkylene-aryl, CO—C$_1$-C$_4$-alkylene-aryl, CO-aryl, SO$_2$-aryl, hetaryl, CO-hetaryl or SO$_2$—C$_1$-C$_4$-alkylene-aryl;

R$_z^6$, R$_z^7$ independently of one another:
  hydrogen, OH or
  each optionally substituted C$_1$-C$_6$-alkyl, C$_1$-C$_4$-alkoxy, C$_2$-C$_6$-alkenyl, C$_2$-C$_6$-alkynyl, C$_1$-C$_6$-alkylene-C$_3$-C$_7$-cycloalkyl, C$_3$-C$_7$-cycloalkyl, aryl, C$_1$-C$_4$-alkylene-aryl, hetaryl or C$_1$-C$_4$-alkylene-hetaryl;

R$^1$, R$^2$, R$^3$ independently of one another:
  hydrogen, OH, CN, or
  each optionally substituted C$_1$-C$_6$-alkyl, O—C$_1$-C$_6$-alkyl, C$_1$-C$_6$-alkylene-O—C$_1$-C$_6$-alkyl, C$_3$-C$_7$-cycloalkyl, O—C$_3$-C$_7$-cycloalkyl, aryl, hetaryl, C$_1$-C$_4$-alkylene-aryl, C$_1$-C$_4$-alkylene-hetaryl, O-aryl, O—C$_1$-C$_4$-alkylene-aryl, O-hetaryl, O—C$_1$-C$_4$-alkylene-hetaryl, CO—C$_1$-C$_6$-alkyl, CO-aryl, CO-hetaryl, CO—C$_1$-C$_4$-alkylene-aryl, CO—C$_1$-C$_4$-alkylene-hetaryl, CO—O—C$_1$-C$_6$-alkyl, CO—O-aryl, CO—O-hetaryl, CO—O—C$_1$-C$_4$-alkylene-aryl, SO$_2$—C$_1$-C$_6$-alkyl, SO$_2$-aryl, SO$_2$-hetaryl, SO$_2$—C$_1$-C$_4$-alkylene-aryl, OCO—C$_1$-C$_6$-alkyl, OCO—aryl, OCO-hetaryl, OCO—C$_1$-C$_4$-alkylene-aryl, OCO—C$_1$-C$_4$-alkylene-hetaryl, SO$_2$—C$_1$-C$_6$-alkyl, SO$_2$-aryl, SO$_2$-hetaryl or SO$_2$—C$_1$-C$_4$-alkylene-aryl, or
  each independently from the third moiety, two moieties of R$^1$, R$^2$ or R$^3$ together form a 5 to 7-membered, optionally substituted, saturated or unsaturated carbocycle or an optionally substituted, saturated or unsaturated heterocycle, which can contain one, two or three further different or identical heteroatoms from the group O, N, S, wherein optionally two moieties substituted on this carbo- or heterocycle together form an anellated, saturated, unsaturated or aromatic carbocycle or heterocycle, wherein the heterocycle can contain up to three different or identical heteroatoms O, N, S, and wherein the cycle formed can optionally be substituted or a further, optionally substituted cycle can be condensed onto this cycle;

Q:
  a doubly substituted 5-membered hetaryl-moiety, chosen from Q1 to Q7

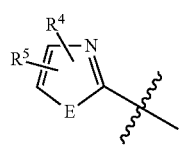
Q1

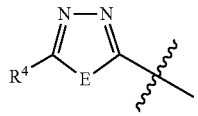
Q2

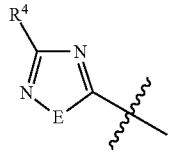
Q3

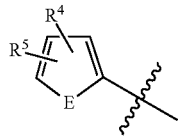
Q4

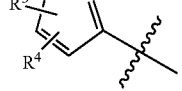
Q5

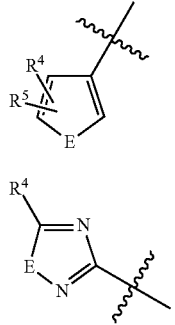
Q6

Q7

E: O, N—R$_Q^1$ or S;
R$_Q^1$:
  hydrogen or
  each optionally substituted C$_1$-C$_4$-alkyl, CO—C$_1$-C$_4$-alkyl, SO$_2$—C$_1$-C$_4$-alkyl, CO—O—C$_1$-C$_4$-alkyl, aryl, C$_1$-C$_4$-alkylene-aryl, CO-aryl, CO-hetaryl, SO$_2$-aryl, SO$_2$-hetaryl, CO—O-aryl, CO—C$_1$-C$_4$-alkylene-aryl, SO$_2$—C$_1$-C$_4$-alkylene-aryl or CO—O—C$_1$-C$_4$-alkylene-aryl;

R$^4$, R$^5$ each independently of one another a moiety chosen from the groups 1.), 2.), 3.), 4.), 5.), 6.) or 7.):
  1.) hydrogen, halogen, CN, CF$_3$, CHF$_2$, or
    each optionally substituted C$_1$-C$_{10}$-alkyl, C$_2$-C$_{10}$-alkenyl, C$_2$-C$_{10}$-alkynyl, C$_3$-C$_7$-cycloalkyl, C$_1$-C$_6$-alkylene-C$_3$-C$_7$-cycloalkyl, C$_1$-C$_4$-alkylene-aryl, C$_1$-C$_4$-alkylene-hetaryl, C$_1$-C$_6$-alkylene-O—C$_1$-C$_6$-alkyl, C$_1$-C$_6$-alkylene-O-aryl, COO—C$_1$-C$_4$-alkyl or C$_1$-C$_4$-alkylene-COO—C$_1$-C$_4$-alkyl;
  2.) Phenyl or naphthyl, which are each substituted with R$_Q^2$, R$_Q^3$ and R$_Q^4$, wherein
    R$_Q^2$, R$_Q^3$ and R$_Q^4$ each independently of one another represent a substituent from the following group: hydrogen, NO$_2$, NH$_2$, OH, CN, CF$_3$, CHF$_2$, OCF$_3$, OCHF$_2$, COOH, O—CH$_2$—COOH, SH, halogen, or
    each optionally substituted aryl, hetaryl, heterocycloalkyl, C$_1$-C$_6$-alkyl, C$_2$-C$_6$-alkenyl, C$_2$-C$_6$-alkynyl, C$_3$-C$_7$-cycloalkyl, C$_1$-C$_4$-alkylene-C$_3$-C$_7$-cycloalkyl, $C_1$-$C_4$-alkylene-heterocycloalkyl, $C_1$-$C_4$-alkylene-aryl or $C_1$-$C_4$-alkylene-hetaryl, or O—$R_Q^5$, S—$R_Q^5$, N$R_Q^7R_Q^8$, CO—O$R_Q^6$, N$R_Q^8$—CO—O—$R_Q^6$, O—CH$_2$—COO—$R_Q^6$, N$R_Q^8$—CO—$R_Q^6$, SO$_2$—$R_Q^6$, N$R_Q^8$—SO$_2$—$R_Q^6$, SO$_2$NH$_2$, CONH$_2$, SO$_2$—N$R_Q^7R_Q^8$ or CO—N$R_Q^7R_Q^8$, or two of the moieties $R_Q^2$, $R_Q^3$ or $R_Q^4$ together form a 3 to 7-membered, optionally substituted, saturated, unsaturated or aromatic carbocycle or an optionally substituted, saturated, unsaturated aromatic heterocycle, which can contain up to three further different or identical heteroatoms O, N, S, and optionally two moieties substituted on this heterocycle can together form an anellated, saturated, unsaturated or aromatic carbocycle or heterocycle, wherein the heterocycle can contain up to three different or identical heteroatoms O, N, S, and the formed cycle can optionally be substituted or a further, optionally substituted cycle can be condensed onto this cycle;

$R_Q^5$ each optionally substituted $C_2$-$C_6$-alkenyl, $C_2$-$C_6$-alkynyl, $C_1$-$C_4$-alkylene-$C_3$-$C_7$-cycloalkyl, $C_1$-$C_4$-alkylene-heterocycloalkyl, heterocycloalkyl or hetaryl, or $C_1$-$C_6$-alkyl, which is optionally substituted with a substituent from the group consisting of halogen, NO$_2$, NH$_2$, OH, CN, CF$_3$, CHF$_2$, OCF$_3$, OCHF$_2$, NH—($C_1$-$C_6$-alkyl) and N($C_1$-$C_6$-alkyl)$_2$;

$R_Q^6$ each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl or $C_1$-$C_6$-alkylene-O—$C_1$-$C_6$-alkyl;

$R_Q^7$ hydrogen, OH, CN, or each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl, $C_1$-$C_6$-alkylene-O—$C_1$-$C_6$-alkyl, CO—$C_1$-$C_6$-alkyl, $C_1$-$C_4$-alkylene-aryl, $C_1$-$C_4$-alkylene-hetaryl, CO-aryl, CO-hetaryl, CO—$C_1$-$C_4$-alkylene-aryl, CO—$C_1$-$C_4$-alkylene-hetaryl, CO—O—$C_1$-$C_6$-alkyl, CO—O-aryl, CO—O—$C_1$-$C_4$-alkylene-aryl, CO—O-hetaryl, CO—O—$C_1$-$C_4$-alkylene-hetaryl, SO$_2$—$C_1$-$C_6$-alkyl, SO$_2$-aryl, SO$_2$-hetaryl, SO$_2$—$C_1$-$C_4$-alkylene-aryl or SO$_2$—$C_1$-$C_4$-alkylene-hetaryl;

$R_Q^8$ hydrogen or each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl, $C_1$-$C_6$-alkylene-O—$C_1$-$C_6$-alkyl, CO—$C_1$-$C_6$-alkyl, CO-aryl, CO-hetaryl, CO—$C_1$-$C_4$-alkylene-aryl, CO—$C_1$-$C_4$-alkylene-hetaryl, CO—O—$C_1$-$C_6$-alkyl, CO—O-aryl, CO—O—$C_1$-$C_4$-alkylene-aryl, CO—O-hetaryl, CO—O—$C_1$-$C_4$-alkylene-hetaryl, SO$_2$—$C_1$-$C_6$-alkyl, SO$_2$-aryl, SO$_2$-hetaryl, SO$_2$—$C_1$-$C_4$-alkylene-aryl or SO$_2$—$C_1$-$C_4$-alkylene-hetaryl;

or the moieties $R_Q^7$ and $R_Q^8$ form, together with the nitrogen, a 3 to 7-membered, optionally substituted, saturated or aromatic heterocycle, which can contain one, two or three further different or identical heteroatoms O, N, S; and optionally two moieties substituted on this heterocycle can together form an anellated, saturated, unsaturated or aromatic carbocycle or heterocycle, wherein the heterocycle can contain up to three different or identical heteroatoms O, N, S, and the cycle formed can optionally be substituted or a further, optionally substituted cycle can be condensed onto this cycle;

3.) a 5- or 6-membered hetaryl moiety, optionally substituted with 1 or 2 substituents, from the group consisting of:

2-pyrrolyl, 3-pyrrolyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl or triazinyl or their anellated derivatives indazolyl, benzothiophenyl, benzofuranyl, indolinyl, benzimidazolyl, benzthiazolyl, benzoxazolyl, chinolinyl and isochinolinyl; or 2-thienyl or 3-thienyl optionally substituted with one or two substituents, wherein the substituents are chosen from the group consisting of halogen, NO$_2$, NH$_2$, OH, CN, CF$_3$, OCF$_3$, CHF$_2$, O—CHF$_2$, $C_1$-$C_6$-alkyl, O—$C_1$-$C_6$-alkyl, NH—($C_1$-$C_6$-alkyl), N($C_1$-$C_6$-alkyl)$_2$, NHCO—$C_1$-$C_4$-alkyl, NHSO$_2$—$C_1$-$C_4$-alkyl and SO$_2$—$C_1$-$C_4$-alkyl;

4.) both moieties $R^4$ and $R^5$ together form a 4 to 7-membered, optionally substituted, saturated or unsaturated or aromatic carbocycle or a 5- or 6-membered optionally substituted, saturated or unsaturated or aromatic heterocycle, which can contain up to three further different or identical heteroatoms O, N, S, and which can be substituted with up to two further moieties, wherein optionally two moieties substituted on this carbo- or heterocycle can together form an anellated, saturated, unsaturated or aromatic carbocycle or heterocycle, wherein the heterocycle can contain up to three different or identical heteroatoms O, N, S and wherein the cycle formed can optionally be substituted or a further, optionally substituted cycle can be condensed onto this cycle;

5.) a $C_5$-$C_{18}$-bi- or tricyclic, saturated hydrocarbon moiety;

6.) each optionally substituted $C_1$-$C_8$-alkyl-NH$_2$, $C_1$-$C_8$-alkyl-N$R_Q^7R_Q^8$, $C_1$-$C_8$-alkyl-CO—N$R_Q^7R_Q^8$, $C_1$-$C_8$-alkyl-SO$_2$N$R_Q^7R_Q^8$, $C_1$-$C_8$-alkyl-CO—NH$_2$, $C_1$-$C_8$-alkyl-SO$_2$NH$_2$, CO—NH$_2$, CO—N$R_Q^7R_Q^8$, SO$_2$NH$_2$, SO$_2$N$R_Q^7R_Q^8$, N$R_Q^7R_Q^8$;

7.) a 4-7-membered mono- or bicyclic saturated or unsaturated heterocycle, which can contain up to two different or identical heteroatoms from the group O, N or S, wherein this cycle can also be multiply substituted. In the case that the heterocycle contains an N-atom, this can be substituted with a moiety $R_Q^7$.

In one embodiment the present invention relates to the guanidine compounds of the formula (I), wherein W:
a moiety of the general formula W1 or W2

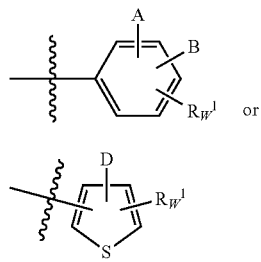

W1 or

W2 wherein

A:
NO$_2$, NH$_2$, OH, CN, CF$_3$, OCF$_3$, CHF$_2$, OCHF$_2$, COOH, O—CH$_2$—COOH, halogen, SH, or each optionally substituted C$_1$-C$_6$-alkyl, C$_2$-C$_6$-alkenyl, C$_2$-C$_6$-alkynyl, C$_3$-C$_7$-cycloalkyl, C$_1$-C$_4$-alkylene-C$_3$-C$_7$-cycloalkyl, C$_1$-C$_4$-alkylene-heterocycloalkyl, aryl, hetaryl, heterocycloalkyl, C$_1$-C$_4$-alkylene-hetaryl or C$_1$-C$_4$-alkylene-aryl, or
O—R$_A^1$, CO—R$_A^1$, S—R$_A^1$, SO—R$_A^1$, CO—O—R$_A^1$, NR$_A^4$—CO—O—R$_A^1$, O—CH$_2$—COO—R$_A^1$, NR$_A^2$R$_A^3$, CONH$_2$, SO$_2$NH$_2$, NR$_A^4$—CO—R$_A^1$, SO$_2$—R$_A^1$, NR$_A^4$—SO$_2$—R$_A^1$, SO$_2$—NR$_A^2$R$_A^3$ or CO—NR$_A^2$NR$_A^3$;

R$_A^1$:
each optionally substituted C$_1$-C$_6$-alkyl, C$_2$-C$_6$-alkenyl, C$_2$-C$_6$-alkynyl, C$_3$-C$_7$-cycloalkyl, C$_1$-C$_4$-alkylene-C$_3$-C$_7$-cycloalkyl, C$_1$-C$_4$-alkylene-heterocycloalkyl, aryl, hetaryl, heterocycloalkyl, C$_1$-C$_4$-alkylene-aryl, C$_2$-C$_6$-alkenylene-aryl or C$_1$-C$_6$-alkylene-hetaryl;

R$_A^2$:
hydrogen, OH, CN, or
each optionally substituted C$_1$-C$_6$-alkyl, C$_2$-C$_6$-alkenyl, C$_2$-C$_6$-alkynyl, C$_1$-C$_4$-alkylene-C$_3$-C$_7$-cycloalkyl, C$_1$-C$_4$-alkylene-heterocycloalkyl, aryl, hetaryl, heterocycloalkyl, C$_1$-C$_4$-alkylene-aryl, C$_1$-C$_4$-alkylene-hetaryl, C$_1$-C$_6$-alkylene-O—C$_1$-C$_6$-alkyl, CO—C$_1$-C$_6$-alkyl, CO-aryl, CO-hetaryl, CO—C$_1$-C$_4$-alkylene-aryl, CO—C$_1$-C$_4$-alkylene-hetaryl, CO—O—C$_1$-C$_6$-alkyl, CO—O-aryl, CO—O—C$_1$-C$_4$-alkylene-aryl, CO—O-hetaryl, CO—O—C$_1$-C$_4$-alkylene-hetaryl, SO$_2$—C$_1$-C$_6$-alkyl, SO$_2$-aryl, SO$_2$-hetaryl, SO$_2$—C$_1$-C$_4$-alkylene-aryl or SO$_2$—C$_1$-C$_4$-alkylene-hetaryl;

R$_A^3$:
each optionally substituted C$_1$-C$_6$-alkyl, C$_2$-C$_6$-alkenyl, C$_2$-C$_6$-alkynyl, C$_1$-C$_4$-alkylene-C$_3$-C$_7$-cycloalkyl, C$_1$-C$_4$-alkylene-heterocycloalkyl, aryl, hetaryl, heterocycloalkyl, C$_1$-C$_4$-alkylene-aryl, C$_1$-C$_4$-alkylene-hetaryl, C$_1$-C$_6$-alkylene-O—C$_1$-C$_6$-alkyl, CO—C$_1$-C$_6$-alkyl, CO-aryl, CO-hetaryl, CO—C$_1$-C$_4$-alkylene-aryl, CO—C$_1$-C$_4$-alkylene-hetaryl, CO—O—C$_1$-C$_6$-alkyl, CO—O-aryl, CO—O—C$_1$-C$_4$-alkylene-aryl, CO—O-hetaryl, CO—O—C$_1$-C$_4$-alkylene-hetaryl, SO$_2$—C$_1$-C$_6$-alkyl, SO$_2$-aryl, SO$_2$-hetaryl, SO$_2$—C$_1$-C$_4$-alkylene-aryl or SO$_2$—C$_1$-C$_4$-alkylene-hetaryl;

or the moieties R$_A^2$ and R$_A^3$ form, together with the nitrogen, a 3 to 7-membered, optionally substituted, saturated or aromatic heterocycle, which can contain one, two or three further different or identical heteroatoms from the group O, N, S; wherein optionally two moieties substituted on this heterocycle can together form an anellated, saturated, unsaturated or aromatic carbocycle or heterocycle, wherein the heterocycle can contain up to three different or identical heteroatoms O, N, S, and wherein the so-formed cycle can optionally be substituted or a further, optionally substituted cycle can be condensed onto this cycle;

R$_A^4$:
hydrogen, or
each optionally substituted C$_1$-C$_6$-alkyl, C$_1$-C$_6$-alkylene-O—C$_1$-C$_6$-alkyl, C$_2$-C$_6$-alkenyl, C$_3$-C$_{12}$-alkynyl, CO—C$_1$-C$_6$-alkyl, CO—O—C$_1$-C$_6$-alkyl, SO$_2$—C$_1$-C$_6$-alkyl, C$_3$-C$_7$-cycloalkyl, aryl, C$_1$-C$_4$-alkylene-aryl, CO—O-arylalkyl, CO—C$_1$-C$_4$-alkylene-aryl, CO-aryl, SO$_2$-aryl, hetaryl, CO-hetaryl or SO$_2$—C$_1$-C$_4$-alkylene-aryl;

B:
hydrogen or as moiety A is defined,
or each independently from one another, two of the moieties A, B or R$_w^1$ together form a 3 to 7-membered, optionally substituted, saturated or unsaturated carbocycle or an optionally substituted, saturated or unsaturated or aromatic heterocycle which can contain one, two or three further different or identical heteroatoms from the group O, N, S; wherein optionally two moieties substituted on this carbo- or heterocycle can together form an anellated, saturated, unsaturated or aromatic carbocycle or heterocycle, wherein the heterocycle can contain up to three different or identical heteroatoms O, N, S and wherein the cycle formed can be optionally substituted or a further, optionally substituted cycle can be condensed onto this cycle;

R$_W^1$:
hydrogen, OH, halogen, NO$_2$, NH$_2$, CN, CF$_3$, CHF$_2$, OCF$_3$, OCHF$_2$, or each optionally substituted C$_1$-C$_6$-alkyl, C$_3$-C$_7$-cycloalkyl, C$_1$-C$_6$-alkylene-O—C$_1$-C$_6$-alkyl, C$_1$-C$_6$-thioalkyl, aryl, hetaryl, O—C$_1$-C$_6$-alkyl, O-aryl, O-benzyl, C$_1$-C$_6$-alkylamino, C$_1$-C$_6$-dialkylamino, pyrrolidinyl, piperidinyl, morpholinyl, CO—C$_1$-C$_6$-alkyl, SO$_2$—C$_1$-C$_6$-alkyl, CO-aryl, SO$_2$-aryl, CO—C$_1$-C$_4$-alkylene-aryl, SO$_2$—C$_1$-C$_4$-alkylene-aryl, SO-aryl, CONH$_2$, CONH—C$_1$-C$_6$-alkyl, SO$_2$NH—C$_1$-C$_6$-alkyl, CON—(C$_1$-C$_6$-alkyl)$_2$, SO$_2$N—(C$_1$-C$_6$-alkyl)$_2$, NH—SO$_2$—C$_1$-C$_6$-alkyl or NH—CO—C$_1$-C$_6$-alkyl;

D:
as moiety A is defined;

Z:
a moiety of the general formula Z1

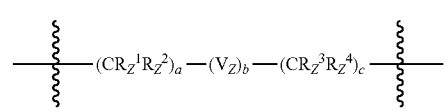

Z1 with the indices
a=0-4
b=0, 1
c=0-4
wherein the sum of a, b and c is at least 1 and no more than 5;

$R_Z^1$, $R_Z^2$, $R_Z^3$, $R_Z^4$ independently of one another:
  hydrogen, halogen, OH, or
    each optionally substituted $C_1$-$C_6$-alkyl, $C_2$-$C_6$-alkenyl, $C_2$-$C_6$-alkynyl, $C_1$-$C_6$-alkylene-$C_3$-$C_7$-cycloalkyl, $C_3$-$C_7$-cycloalkyl, aryl, $C_1$-$C_4$-alkylene-aryl, hetaryl or $C_1$-$C_4$-alkylene-hetaryl, or
    each independently of one another two moieties $R_Z^1$ and $R_Z^2$ or $R_Z^3$ and $R_Z^4$ together form a 3 to 7-membered, optionally substituted, saturated or unsaturated carbo- or heterocycle, wherein the heterocycle can contain up to three heteroatoms of the group O, N, or S;

$V_Z$:
  —CO—, —CO—$NR_Z^5$—, —$NR_Z^5$—CO—, —O—, —S—, —SO—, —$SO_2$—, —$SO_2$—$NR_Z^5$—, —$NR_Z^5$—$SO_2$—, —CS—, —CS—$NR_Z^5$—, —$NR_Z^5$—CS—, —CS—O—, —O—CS—, —CO—O—, —O—CO—, —O—, ethynylene, —C(=$CR_Z^6 R_Z^7$)—, —$CR_Z^6$=$CR_Z^7$—, —$NR_Z^5$—CO—$NR_Z^{5*}$—, —O—CO—$NR_Z^5$—, —$NR_Z^5$—;

$R_Z^5$, $R_Z^{5*}$ independently of one another:
  hydrogen or
    each optionally substituted $C_1$-$C_6$-alkyl, $C_1$-$C_6$-alkylene-O—$C_1$-$C_6$-alkyl, $C_2$-$C_6$-alkenyl, $C_3$-$C_{12}$-alkynyl, CO—$C_1$-$C_6$-alkyl, CO—O—$C_1$-$C_6$-alkyl, $SO_2$—$C_1$-$C_6$-alkyl, $C_3$-$C_7$-cycloalkyl, aryl, $C_1$-$C_4$-alkylen-aryl, CO—O—$C_1$-$C_4$-alkylene-aryl, CO—$C_1$-$C_4$-alkylene-aryl, CO-aryl, $SO_2$-aryl, hetaryl, CO-hetaryl or $SO_2$—$C_1$-$C_4$-alkylene-aryl;

$R_Z^6$, $R_Z^7$ independently of one another:
  hydrogen, OH or
    each optionally substituted $C_1$-$C_6$-alkyl, $C_1$-$C_4$-alkoxy, $C_2$-$C_6$-alkenyl, $C_2$-$C_6$-alkynyl, $C_1$-$C_6$-alkylene-$C_3$-$C_7$-cycloalkyl, $C_3$-$C_7$-cycloalkyl, aryl, $C_1$-$C_4$-alkylene-aryl, hetaryl or $C_1$-$C_4$-alkylene-hetaryl;

$R^1$, $R^2$, $R^3$ independently of one another:
  hydrogen, OH, CN, or
    each optionally substituted $C_1$-$C_6$-alkyl, O—$C_1$-$C_6$-alkyl, $C_1$-$C_6$-alkylene-O—$C_1$-$C_6$-alkyl, $C_3$-$C_7$-cycloalkyl, O—$C_3$-$C_7$-cycloalkyl, aryl, hetaryl, $C_1$-$C_4$-alkylene-aryl, $C_1$-$C_4$-alkylene-hetaryl, O-aryl, O—$C_1$-$C_4$-alkylene-aryl, O-hetaryl, O—$C_1$-$C_4$-alkylene-hetaryl, CO—$C_1$-$C_6$-alkyl, CO-aryl, CO-hetaryl, CO—$C_1$-$C_4$-alkylene-aryl, CO—$C_1$-$C_4$-alkylene-hetaryl, CO—O—$C_1$-$C_6$-alkyl, CO—O-aryl, CO—O-hetaryl, CO—O—$C_1$-$C_4$-alkylene-aryl, $SO_2$—$C_1$-$C_6$-alkyl, $SO_2$-aryl, $SO_2$-hetaryl, $SO_2$—$C_1$-$C_4$-alkylene-aryl, OCO—$C_1$-$C_6$-alkyl, OCO-aryl, OCO-hetaryl, OCO—$C_1$-$C_4$-alkylene-aryl, OCO—$C_1$-$C_4$-alkylene-hetaryl, $SO_2$—$C_1$-$C_6$-alkyl, $SO_2$-aryl, $SO_2$-hetaryl or $SO_2$—$C_1$-$C_4$-alkylene-aryl, or
    each independently from the third moiety, two moieties of $R^1$, $R^2$ or $R^3$ together form a 5 to 7-membered, optionally substituted, saturated or unsaturated carbocycle or an optionally substituted, saturated or unsaturated heterocycle, which can contain one, two or three further different or identical heteroatoms from the group O, N, S, wherein optionally two moieties substituted on this carbo- or heterocycle can together form an anellated, saturated, unsaturated or aromatic carbocycle or heterocycle, wherein the heterocycle can contain up to three different or identical heteroatoms O, N, S and wherein the cycle formed can optionally be substituted or a further, optionally substituted cycle can be condensed onto this cycle;

Q:
  a doubly substituted 5-membered hetaryl-moiety, chosen from Q1 to Q6

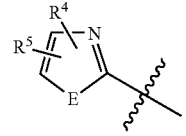

Q1

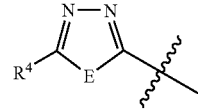

Q2

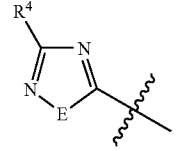

Q3

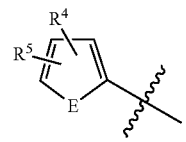

Q4

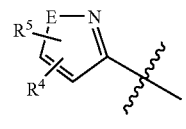

Q5

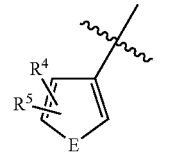

Q6

E: O, N—$R_Q^1$ or S;

$R_Q^1$:
  hydrogen, or
    each optionally substituted $C_1$-$C_4$-alkyl, CO—$C_1$-$C_4$-alkyl, $SO_2$—$C_1$-$C_4$-alkyl, CO—O—$C_1$-$C_4$-alkyl, aryl, $C_1$-$C_4$-alkylene-aryl, CO-aryl, CO-hetaryl, $SO_2$-aryl, $SO_2$-hetaryl, CO—O-aryl, CO—$C_1$-$C_4$-alkylene-aryl, $SO_2$—$C_1$-$C_4$-alkylene-aryl or CO—O—$C_1$-$C_4$-alkylene-aryl;

$R^4$, $R^5$ each independently from one another a moiety chosen from the groups 1.), 2.), 3.), 4.) or 5.):
  1.) hydrogen, halogen, CN, $CF_3$, $CHF_2$, or
    each optionally substituted $C_1$-$C_{10}$-alkyl, $C_2$-$C_{10}$-alkenyl, $C_2$-$C_{10}$-alkynyl, $C_3$-$C_7$-cycloalkyl, $C_1$-$C_6$-alkylene-$C_3$-$C_7$-cycloalkyl, $C_1$-$C_4$-alkylene-aryl, $C_1$-$C_4$-alkylene-hetaryl, $C_1$-$C_6$-alkylene-O—$C_1$-$C_6$-alkyl, $C_1$-$C_6$-alkylene-β-aryl, COO—$C_1$-$C_4$-alkyl or $C_1$-$C_4$-alkylene-COO—$C_1$-$C_4$-alkyl;
  2.) Phenyl or naphthyl, which are each substituted with $R_Q^2$, $R_Q^3$ and $R_Q^4$, wherein
    $R_Q^2$, $R_Q^3$ and $R_Q^4$ each independently from one another represent a substituent from the following group:
      hydrogen, $NO_2$, $NH_2$, OH, CN, $CF_3$, $CHF_2$, $OCF_3$, $OCHF_2$, COOH, O—$CH_2$—COOH, SH, halogen, or each optionally substituted aryl, hetaryl, heterocycloalkyl, $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, $C_1$-$C_4$-alkylene-aryl or $C_1$-$C_4$-alkylene-hetaryl, or
O—$R_Q^5$, S—$R_Q^5$, $NR_Q^7R_Q^8$, CO—$OR_Q^6$, $NR_Q^8$—COO—O—$R_Q^6$, O—$CH_2$—COO—$R_Q^6$, $NR_Q^8$—CO—$R_Q^6$, $SO_2$—$R_Q^6$, $NR_Q^8$—$SO_2$—$R_Q^6$, $SO_2NH_2$, $CONH_2$, $SO_2$—$NR_Q^7R_Q^8$ or CO—$NR_Q^7R_Q^8$, or two of the moieties $R_Q^2$, $R_Q^3$ or $R_Q^4$ together form a 3 to 7-membered, optionally substituted, saturated, unsaturated or aromatic carbocycle or an optionally substituted, saturated, unsaturated aromatic heterocycle, which can contain up to three further different or identical heteroatoms O, N, S, and optionally two moieties substituted on this heterocycle can together form an anellated, saturated, unsaturated or aromatic carbocycle or heterocycle, wherein the heterocycle can contain up to three different or identical heteroatoms O, N, S, and the cycle formed can optionally be substituted or a further, optionally substituted cycle can be condensed onto this cycle;

$R_Q^5$ each optionally substituted $C_2$-$C_6$-alkenyl, $C_2$-$C_6$-alkynyl, $C_1$-$C_4$-alkylene-$C_3$-$C_7$-cycloalkyl, $C_1$-$C_4$-alkylene-heterocycloalkyl, heterocycloalkyl or hetaryl, or $C_1$-$C_6$-alkyl, which can optionally be substituted with a substituent from the group consisting of halogen, $NO_2$, $NH_2$, OH, CN, $CF_3$, $CHF_2$, $OCF_3$, $OCHF_2$, NH—($C_1$-$C_6$-alkyl) and N($C_1$-$C_6$-alkyl)$_2$;

$R_Q^6$ each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl or $C_1$-$C_6$-alkylene-O—$C_1$-$C_6$-alkyl;

$R_Q^7$ hydrogen, OH, CN, or
each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl, $C_1$-$C_6$-alkylene-O—$C_1$-$C_6$-alkyl, CO—$C_1$-$C_6$-alkyl, $C_1$-$C_4$-alkylene-aryl, $C_1$-$C_4$-alkylene-hetaryl, CO-aryl, CO-hetaryl, CO—$C_1$-$C_4$-alkylene-aryl, CO—$C_1$-$C_4$-alkylene-hetaryl, CO—O—$C_1$-$C_6$-alkyl, CO—O-aryl, CO—O—$C_1$-$C_4$-alkylene-aryl, CO—O-hetaryl, CO—O—$C_1$-$C_4$-alkylene-hetaryl, $SO_2$—$C_1$-$C_6$-alkyl, $SO_2$-aryl, $SO_2$-hetaryl, $SO_2$—$C_1$-$C_4$-alkylene-aryl or $SO_2$—$C_1$-$C_4$-alkylene-hetaryl;

$R_Q^8$ each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl, $C_1$-$C_6$-alkylene-O—$C_1$-$C_6$-alkyl, CO—$C_1$-$C_6$-alkyl, CO-aryl, CO-hetaryl, CO—$C_1$-$C_4$-alkylene-aryl, CO—$C_1$-$C_4$-alkylene-hetaryl, CO—O—$C_1$-$C_6$-alkyl, CO—O-aryl, CO—O—$C_1$-$C_4$-alkylene-aryl, CO—O-hetaryl, CO—O—$C_1$-$C_4$-alkylene-hetaryl, $SO_2$—$C_1$-$C_6$-alkyl, $SO_2$-aryl, $SO_2$-hetaryl, $SO_2$—$C_1$-$C_4$-alkylene-aryl or $SO_2$—$C_1$-$C_4$-alkylene-hetaryl;

or the moieties $R_Q^7$ and $R_Q^8$ form, together with the nitrogen, a 3 to 7-membered, optionally substituted, saturated or aromatic heterocycle, which can contain one, two or three further different or identical heteroatoms O, N, S; and optionally two moieties substituted on this heterocycle can together form an anellated, saturated, unsaturated or aromatic carbocycle or heterocycle, wherein the heterocycle can contain up to three different or identical heteroatoms O, N, S, and the cycle formed can optionally be substituted or a further, optionally substituted cycle can be condensed onto this cycle;

3.) a 5- or 6-membered hetaryl moiety optionally substituted with one or two substituents from the group consisting of:
2-pyrrolyl, 3-pyrrolyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl or triazinyl or their anellated derivatives indazolyl, benzothiophenyl, benzofuranyl, indolinyl, benzimidazolyl, benzthiazolyl, benzoxazolyl, chinolinyl and isochinolinyl; or
2-thienyl or 3-thienyl optionally substituted with 1 or 2 substituents, wherein the substituents are chosen from the group consisting of halogen, $NO_2$, $NH_2$, OH, CN, $CF_3$, $OCF_3$, $CHF_2$, O—$CHF_2$, $C_1$-$C_6$-alkyl, O—$C_1$-$C_6$-alkyl, NH—($C_1$-$C_6$-alkyl), N($C_1$-$C_6$-alkyl)$_2$, NHCO—$C_1$-$C_4$-alkyl, NHSO$_2$—$C_1$-$C_4$-alkyl and $SO_2$—$C_1$-$C_4$-alkyl;

4.) both moieties $R^4$ and $R^5$ together form a 4 to 7-membered, optionally substituted, saturated or unsaturated or aromatic carbocycle or a 5- or 6-membered optionally substituted, saturated or unsaturated or aromatic heterocycle, which can contain up to three further different or identical heteroatoms O, N, S, and can be substituted with up to two further moieties, wherein optionally two moieties substituted on this carbo- or heterocycle can together form an anellated, saturated, unsaturated or aromatic carbocycle or heterocycle, wherein the heterocycle can contain up to three different or identical heteroatoms O, N, S and wherein the cycle formed can optionally be substituted or a further, optionally substituted cycle can be condensed onto this cycle;

5.) a $C_5$-$C_{18}$-bi- or tricyclic, saturated hydrocarbon moiety.

Advantageously, the guanadine compounds have moieties with the following definitions:
W: W1;
A: halogen, OH, CN, $CF_3$, —$CHF_2$, $OCF_3$, $OCHF_2$, or
each optionally substituted $C_1$-$C_6$-alkyl or $C_2$-$C_6$-alkenyl, O—$CH_2$—COO—$R_A^1$, O—$R_A^1$, S—$R_A^1$, $NR_A^2R_A^3$, $NR_A^4$—CO—$R_A^1$ or —CO—$NR_A^4R_a^1$;

$R_A^1$: each optionally substituted $C_1$-$C_4$-alkyl, $C_3$-$C_7$-cycloalkyl, phenyl or benzyl;

$R_A^2$: hydrogen, or
each optionally substituted $C_1$-$C_4$-alkyl, phenyl, benzyl, phenethyl, CO—$C_1$-$C_4$-alkyl, CO-aryl, CO—O—$C_1$-$C_4$-alkyl, $SO_2$—$C_1$-$C_4$-alkyl, $SO_2$-aryl, $SO_2$-hetaryl or $SO_2$—$C_1$-$C_4$-alkylene-aryl;

$R_A^3$: each optionally substituted $C_1$-$C_4$-alkyl, phenyl, benzyl, phenethyl, CO—$C_1$-$C_4$-alkyl, CO-aryl, CO—O—$C_1$-$C_4$-alkyl, $SO_2$—$C_1$-$C_4$-alkyl, $SO_2$-aryl, $SO_2$-hetaryl, or $SO_2$—$C_1$-$C_4$-alkylene-aryl;

or both moieties $R_A^2$ and $R_A^3$ together form an optionally substituted 5- or 6-membered saturated or unsaturated ring, which can contain up to two identical or different heteroatoms from the group O and N;

$R_A^4$: hydrogen or an optionally substituted $C_1$-$C_4$-alkyl moiety;

B: hydrogen or as moiety A;

$R_W^1$: hydrogen, F, Cl, CN, $CF_3$, O—$CF_3$, or each optionally substituted $C_1$-$C_4$-alkyl, aryl, $C_1$-$C_6$-alkylamino or $C_1$-$C_6$-dialkylamino;

in the formula Z1 the sum of a, b, c is 1, 2 or 3;

$R_Z^1, R_Z^2, R_Z^3, R_Z^4$ independently of one another: hydrogen, halogen, OH, optionally substituted $C_1$-$C_6$-alkyl;

$V_Z$: —CO—, —CO—$NR_z^5$—, —$NR_z^5$—CO—, —O—, —S—;

$R_Z^5$: hydrogen, $CH_3$;

$R^1, R^2, R^3$ independently of one another:
hydrogen, OH, CN, $C_{1-4}$-alkyl, $C_1$-$C_6$-alkylene-O—$C_1$-$C_6$-alkyl, substituted aryl, benzyl, CO—$C_1$-$C_5$-alkyl, CO-aryl, CO—$C_1$-$C_4$-alkylene-aryl, OCO—$C_1$-$C_6$-alkyl, OCO-aryl or OCO—$C_1$-$C_4$-alkylene-hetaryl;

Q is chosen from the group consisting of Q1, Q2 and Q3;

$R_Q^1$: hydrogen, optionally substituted $C_1$-$C_4$-alkyl, in the aryl moiety optionally substituted benzyl, CO—$C_1$-$C_4$-alkyl, optionally substituted benzoyl, $SO_2$—$C_1$-$C_4$-alkyl or in the aryl moiety optionally substituted $SO_2$-aryl.

It is still more preferred that the guanidine compounds have moieties with the following definitions:

A: OH, F, Cl, $OCF_3$, $OCHF_2$, optionally substituted $C_1$-$C_4$-alkyl, O—$C_1$-$C_4$-alkyl or S—$C_1$-$C_4$-alkyl;

B: hydrogen, OH, F, Cl, $CF_3$, $OCF_3$, $OCHF_2$, optionally substituted $C_1$-$C_4$-alkyl, O—$C_1$-$C_4$-alkyl or S—$C_1$-$C_4$-alkyl;

$R_W^1$: hydrogen, F, Cl, CN, $CF_3$ or O—$CF_3$;

Z: each optionally substituted $C_{1-4}$-alkyl or $C_1$-$C_4$-alkylene-O—$C_1$-$C_4$-alkyl;

$R_Z^1, R_Z^2, R_Z^3, R_Z^4$ each independent of one another hydrogen, F, $CH_3$;

$R^1, R^2, R^3$ independent of one another:
hydrogen, OH, CN, O-methyl, O-phenyl, acetyl, benzoyl, O-acetyl, O-benzoyl;

Q is chosen from the group consisting of

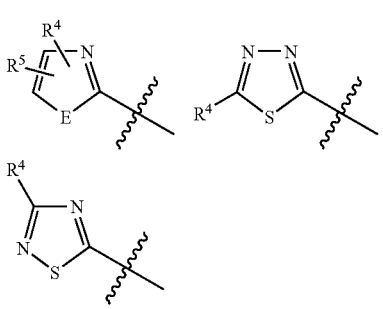

$R_Q^1$: hydrogen, $CH_3$, methanesulfonyl, phenylsulfonyl or tosyl.

In a further preferred embodiment the guanidine compounds have moieties with the following definitions:

A: OH, $OCF_3$, $OCH_3$, O-ethyl, O-propyl or O-i-propyl;

Z: —$CH_2$—, —$CH_2$—O—, —$CH_2$—$CH_2$— or —$CH_2$—$CH_2$—O—;

two of the moieties $R^1$, $R^2$, or $R^3$, are hydrogen and the third moiety is hydrogen, OH, acetyl or benzoyl;

Q:

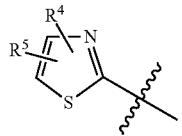

In a further preferred embodiment, $R^4$ and/or $R^5$ each independently of one another, represent a moiety chosen from the groups 1.), 2.), 3.), 4.) or 5.):

1.) hydrogen, F, Cl, CN, $CF_3$, or each optionally substituted $C_1$-$C_6$-alkyl, $C_2$-$C_6$-alkenyl, $C_1$-$C_6$-alkylene-O—$C_1$-$C_6$-alkyl or $C_3$-$C_7$-cycloalkyl;

2.) $R_Q^1, R_Q^2$ and $R_Q^3$ independently of one another
hydrogen, —CN, —$CF_3$, —$CHF_2$, —$OCF_3$, —$OCHF_2$, F, Cl, OH or each optionally substituted phenyl or hetaryl, $C_1$-$C_4$-alkyl, $C_6$-$C_7$-cycloalkyl, O—$R_Q^5$, $NR_Q^7R_Q^8$, CO—$OR_Q^6$, $NR_Q^8$—COO—O—$R_Q^6$, O—$CH_2$—COO—$R_Q^6$, $NR_Q^8$—CO—$R_Q^6$, $SO_2$—$R_Q^6$, $NR_Q^8$—$SO_2$—$R_Q^6$, $NR_Q^8$—COO—O—$R_Q^6$, $SO_2NH_2$, $CONH_2$, $SO_2$—$NR_Q^7R_Q^8$ or CO—$NR_Q^7R_Q^8$;

$R_Q^5$: $C_1$-$C_4$-alkyl, which is optionally substituted with substituents from the group consisting of F, Cl, OH, CN, $CF_3$, $OCF_3$, NH—($C_{1-4}$-alkyl) and N($C_{1-4}$-alkyl)$_2$;

$R_Q^6$ each optionally substituted $C_1$-$C_6$-alkyl, aryl, hetaryl or phenyl;

$R_Q^7$ hydrogen, each optionally substituted $C_1$-$C_4$-alkyl, allyl, aryl, hetaryl, benzyl, phenethyl or $CH_2$-hetaryl;

$R_Q^8$ each optionally substituted $C_1$-$C_4$-alkyl, allyl, aryl, hetaryl, benzyl, phenethyl or $CH_2$-hetaryl;

or $R_Q^7$ and $R_Q^8$ form an optionally substituted 3- or 7-membered saturated or unsaturated ring which can contain up to two identical or different heteroatoms from the group O and N;

3.) benzothiophenyl, benzofuranyl, chinolinyl or isochinolinyl;

4.) both moieties $R^4$ and $R^5$ together form one of the following rings:

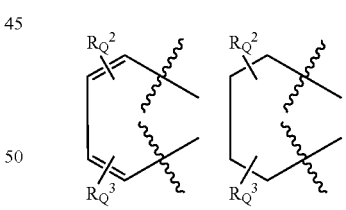

wherein $R_Q^2$ and $R_Q^3$ are as defined under 2.);

5.) Adamantyl.

It is preferred that a moiety from $R^4$ and $R^5$ is chosen from group 1 and that the other from $R^4$ and $R^5$ is chosen from group 1, 2 or 3.

The present invention further relates to the use of these guanidine compounds as medicaments as well as pharmaceutical compositions comprising at least one of these guanidine compounds as well as a pharmaceutically acceptable carrier or dilution agent.

The present invention further relates to the use of these guanidine compounds for the preparation of a medicament for the treatment of diseases, which are modulated by 5-HT5 receptor activity, as is set out in detail below.

The present invention further relates to the use of compounds of the general formula IVa for the preparation of 5HT5 receptor ligands:

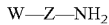   IVa

Here it is preferred that these compounds for the preparation of guanidine compounds, according to the invention, are used.

The present invention further relates to the use of a guanidine compound of the general formula IA

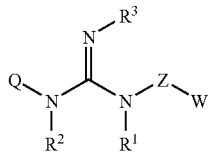   IA corresponding enantiomeric, diastereomeric and/or tautomeric forms thereof, as well as pharmaceutically acceptable salts thereof,
wherein the given moieties have the following definitions:

W:
   a moiety of the general formula W1 or W2

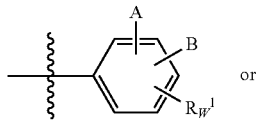   W1

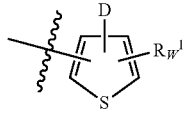   W2

A:
   $NO_2$, $NH_2$, OH, CN, $CF_3$, $OCF_3$, $CHF_2$, $OCHF_2$, COOH, O—$CH_2$—COOH, halogen, SH, or
   each optionally substituted $C_1$-$C_6$-alkyl, $C_2$-$C_6$-Alkenyl, $C_2$-$C_6$-Alkynyl, $C_3$-$C_7$-cycloalkyl, $C_1$-$C_4$-alkylene-$C_3$-$C_7$-cycloalkyl or $C_1$-$C_4$-alkylene-hetero-cycloalkyl, aryl, hetaryl, heterocycloalkyl, $C_1$-$C_4$-alkylene-hetaryl or $C_1$-$C_4$-alkylene-aryl, or
   O—$R_A^1$, CO—$R_A^1$, S—$R_A^1$, SO—$R_A^1$, CO—O—$R_A^1$, $NR_A^4$—COO—O—$R_A^1$, O—$CH_2$—COO—$R_A^1$, $NR_A^2R_A^3$, $CONH_2$, $SO_2NH_2$, $NR_A^4$—CO—$R_A^1$, $SO_2$—$R_A^1$, $NR_A^4$—$SO_2$—$R_A^1$, $SO_2$—$NR_A^2R_A^3$ or CO—$NR_A^2R_A^3$;

$R_A^1$:
   each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl, $C_1$-$C_4$-alkylene-aryl, $C_2$-$C_6$-alkenylene-aryl or $C_1$-$C_6$-alkylene-hetaryl;

$R_A^2$:
   hydrogen, OH, CN, or
   each optionally substituted $C_1$-$C_6$-alkyl, $C_2$-$C_6$-alkenyl, $C_2$-$C_6$-alkynyl, $C_1$-$C_4$-alkylen-$C_3$-$C_7$-cycloalkyl, $C_1$-$C_4$-alkylene-heterocycloalkyl, aryl, hetaryl, heterocycloalkyl, $C_1$-$C_4$-alkylene-aryl, $C_1$-$C_4$-alkylene-hetaryl, $C_1$-$C_6$-alkylene-O—$C_1$-$C_6$-alkyl, CO—$C_1$-$C_6$-alkyl, CO-aryl, CO-hetaryl, CO—$C_1$-$C_4$-alkylene-aryl, CO—$C_1$-$C_4$-alkylene-hetaryl, CO—O—$C_1$-$C_6$-alkyl, CO—O-aryl, CO—O—$C_1$-$C_4$-alkylene-aryl, CO—O-hetaryl, CO—O—$C_1$-$C_4$-alkylene-hetaryl, $SO_2$—$C_1$-$C_6$-alkyl, $SO_2$-aryl, $SO_2$-hetaryl, $SO_2$—$C_1$-$C_4$-alkylene-aryl or $SO_2$—$C_1$-$C_4$-alkylene-hetaryl;

$R_A^3$:
   each optionally substituted $C_1$-$C_6$-alkyl, $C_2$-$C_6$-alkenyl, $C_2$-$C_6$-alkynyl, $C_1$-$C_4$-alkylene-$C_3$-$C_7$-cycloalkyl, $C_1$-$C_4$-alkylene-heterocycloalkyl, aryl, hetaryl, heterocycloalkyl, $C_1$-$C_4$-alkylene-aryl, $C_1$-$C_4$-alkylene-hetaryl, $C_1$-$C_6$-alkylene-O—$C_1$-$C_6$-alkyl, CO—$C_1$-$C_6$-alkyl, CO-aryl, CO-hetaryl, CO—$C_1$-$C_4$-alkylene-aryl, CO—$C_1$-$C_4$-alkylene-hetaryl, CO—O—$C_1$-$C_6$-alkyl, CO—O-aryl, CO—O—$C_1$-$C_4$-alkylene-aryl, CO—O-hetaryl, CO—O—$C_1$-$C_4$-alkylene-hetaryl, $SO_2$—$C_1$-$C_6$-alkyl, $SO_2$-aryl, $SO_2$-hetaryl, $SO_2$—$C_1$-$C_4$-alkylene-aryl or $SO_2$—$C_1$-$C_4$-alkylene-hetaryl;
   or the moieties $R_A^2$ and $R_A^3$ form, together with the nitrogen, a 3 to 7-membered, optionally substituted, saturated or aromatic heterocycle, which can contain one, two or three further different or identical heteroatoms from the group O, N, S; wherein optionally two moieties substituted on this heterocycle can together form an anellated, saturated, unsaturated or aromatic carbocycle or heterocycle, wherein the heterocycle can contain up to three different or identical heteroatoms O, N, S, and wherein the cycle formed can optionally be substituted or a further, optionally substituted cycle can be condensed onto this cycle;

$R_A^4$:
   hydrogen, or
   each optionally substituted $C_1$-$C_6$-alkyl, $C_1$-$C_6$-alkylene-O—$C_1$-$C_6$-alkyl, $C_2$-$C_6$-alkenyl, $C_3$-$C_{12}$-alkynyl, CO—$C_1$-$C_6$-alkyl, CO—O—$C_1$-$C_6$-alkyl, $SO_2$—$C_1$-$C_6$-alkyl, $C_3$-$C_7$-cycloalkyl, aryl, $C_1$-$C_4$-alkylene-aryl, CO—O-arylalkyl, CO—$C_1$-$C_4$-alkylene-aryl, CO-aryl, $SO_2$-aryl, hetaryl, CO-hetaryl or $SO_2$—$C_1$-$C_4$-alkylene-aryl;

B:
   hydrogen or as moiety A is defined,
   or each independently of each other, two of the moieties A, B or $R_W^1$ together form a 3 to 7-membered, optionally substituted, saturated or unsaturated carbocycle or an optionally substituted, saturated or unsaturated or aromatic heterocycle, which can contain one, two or three further different or identical heteroatoms from the group O, N, S; wherein optionally two moeities substituted on this carbo- or heterocycle can together form an anellated, saturated, unsaturated or aromatic carbocycle or heterocycle, wherein the heterocycle can contain up to three different or identical heteroatoms O, N, S and wherein the cycle formed can optionally be substituted or a further, optionally substituted cycle can be condensed onto this cycle;

$R_W^1$:
   hydrogen, OH, halogen, $NO_2$, $NH_2$, CN, $CF_3$, $CHF_2$, $OCF_3$, $OCHF_2$, or each optionally substituted $C_1$-$C_6$-alkyl, $C_3$-$C_7$-cycloalkyl, $C_1$-$C_6$-alkylene-O—$C_1$-$C_6$-alkyl, $C_1$-$C_6$-alkylene-S—$C_1$-$C_6$-alkyl, aryl, hetaryl, O—$C_1$-$C_6$-alkyl, O-aryl, O-benzyl, $C_1$-$C_6$-alkylamino, $C_1$-$C_6$-dialkylamino, pyrrolidinyl, piperidinyl, morpholinyl, CO—$C_1$-$C_6$-alkyl, $SO_2$—$C_1$-$C_6$-alkyl, CO-aryl, $SO_2$-aryl, CO—$C_1$-$C_4$-alkylene-aryl, $SO_2$—$C_1$-$C_4$-alkylene-aryl, SO-aryl, $CONH_2$, CONH—$C_1$-$C_6$-alkyl, $SO_2$NH—$C_1$-$C_6$-alkyl, CON($C_1$-$C_6$-alkyl)$_2$, $SO_2$N($C_1$-$C_6$-alkyl)$_2$, NH—$SO_2$—$C_1$-$C_6$-alkyl or NH—CO—$C_1$-$C_6$-alkyl;

D:
 as moiety A is defined;

Z:
 a moiety of the general formula Z1

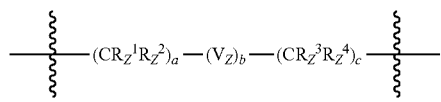

with the indices
 a=0-4
 b=0, 1
 c=0-4
 wherein the sum of a, b and c is no more than 5;

$R_Z^1$, $R_Z^2$, $R_Z^3$, $R_Z^4$ independently of one another:
 hydrogen, halogen, OH, or
 each optionally substituted $C_1$-$C_6$-alkyl, $C_2$-$C_6$-alkenyl, $C_2$-$C_6$-alkynyl, $C_1$-$C_6$-alkylene-$C_3$-$C_7$-cycloalkyl, $C_3$-$C_7$-cycloalkyl, aryl, $C_1$-$C_4$-alkylene-aryl, hetaryl or $C_1$-$C_4$-alkylene-hetaryl, or
 each independently of one another, two moieties $R_Z^1$ and $R_Z^2$ or $R_Z^3$ and $R_Z^4$ together form a 3 to 7-membered, optionally substituted, saturated or unsaturated carbo- or heterocycle, which can contain up to three heteroatoms from the group O, N or S;

$V_Z$:
 —CO—, —CO—$NR_Z^5$—, —$NR_Z^5$—CO—, —O—, —S—, —SO—, —$SO_2$—, —$SO_2$—$NR_Z^5$—, —$NR_Z^5$—$SO_2$—, —CS—, —CS—$NR_Z^5$—, —$NR_Z^5$—CS—, —CS—O—, —O—CS—, —CO—O—, —O—CO—, —O—, ethynylene, —C(=$CR_Z^5$—$R_Z^7$)—, —$CR_Z^6$=$CR_Z^7$—, —$NR_Z^5$—CO—$NR_Z^{5*}$-, —O—CO—$NR_Z^5$—, —$NR_Z^5$—;

$R_Z^5$, $R_Z^{5*}$ independently of one another:
 hydrogen, or
 each optionally substituted $C_1$-$C_6$-alkyl, $C_1$-$C_6$-alkylene-O—$C_1$-$C_6$-alkyl, $C_2$-$C_6$-alkenyl, $C_3$-$C_{12}$-alkynyl, CO—$C_1$-$C_6$-alkyl, CO—O—$C_1$-$C_6$-alkyl, $SO_2$—$C_1$-$C_6$-alkyl, $C_3$-$C_7$-cycloalkyl, aryl, $C_1$-$C_4$-alkylene-aryl, CO—O—$C_1$-$C_4$-alkylene-aryl, CO—$C_1$-$C_4$-alkylene-aryl, CO-aryl, $SO_2$-aryl, hetaryl, CO-hetaryl or $SO_2$—$C_1$-$C_4$-alkylene-aryl;

$R_Z^6$, $R_Z^7$ independently of one another:
 hydrogen, OH,
 each optionally substituted $C_1$-$C_6$-alkyl, $C_1$-$C_4$-alkoxy, $C_2$-$C_6$-alkenyl, $C_2$-$C_6$-alkynyl, $C_1$-$C_6$-alkylene-$C_3$-$C_7$-cycloalkyl, $C_3$-$C_7$-cycloalkyl, aryl, $C_1$-$C_4$-alkylene-aryl, hetaryl or $C_1$-$C_4$-alkylene-hetaryl;

$R^1$, $R^2$, $R^3$ independently of one another:
 hydrogen, OH, CN, or
 each optionally substituted $C_1$-$C_6$-alkyl, O—$C_1$-$C_6$-alkyl, $C_1$-$C_6$-alkylene-O—$C_1$-$C_6$-alkyl, $C_3$-$C_7$-cycloalkyl, O—$C_3$-$C_7$-cycloalkyl, aryl, hetaryl, $C_1$-$C_4$-alkylene-aryl, $C_1$-$C_4$-alkylene-hetaryl, O-aryl, O—$C_1$-$C_4$-alkylene-aryl, O-hetaryl, O—$C_1$-$C_4$-alkylene-hetaryl, CO—$C_1$-$C_6$-alkyl, CO-aryl, CO-hetaryl, CO—$C_1$-$C_4$-alkylene-aryl, CO—$C_1$-$C_4$-alkylene-hetaryl, CO—O—$C_1$-$C_6$-alkyl, CO—O-aryl, CO—O-hetaryl, CO—O—$C_1$-$C_4$-alkylene-aryl, $SO_2$—$C_1$-$C_6$-alkyl, $SO_2$-aryl, $SO_2$-hetaryl, $SO_2$—$C_1$-$C_4$-alkylene-aryl, OCO—$C_1$-$C_6$-alkyl, OCO-aryl, OCO-hetaryl, OCO—$C_1$-$C_4$-alkylene-aryl, OCO—$C_1$-$C_4$-alkylene-hetaryl, $SO_2$—$C_1$-$C_6$-alkyl, $SO_2$-aryl, $SO_2$-hetaryl or $SO_2$—$C_1$-$C_4$-alkylene-aryl, or
 each independently from the third moiety, two moieties of $R^1$, $R^2$ or $R^3$ together form a 5 to 7-membered, optionally substituted, saturated or unsaturated carbocycle, or an optionally substituted, saturated or unsaturated, which can contain two or three further different or identical heteroatoms from the group O, N, S, wherein optionally two moieties substituted on this carbo- or heterocycle can together form an anellated, saturated, unsaturated or aromatic carbocycle or heterocycle, wherein the heterocycle can contain up to three different or identical heteroatoms O, N, S and wherein the cycle formed can optionally be substituted or a further, optionally substituted cycle can be condensed onto this cycle;

Q:
 a doubly substituted 5-membered hetaryl-moiety, chosen from Q1 to Q6

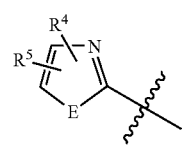

Q1

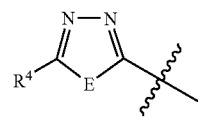

Q2

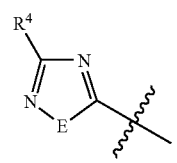

Q3

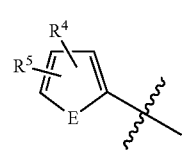

Q4

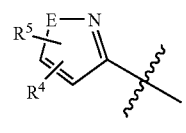

Q5

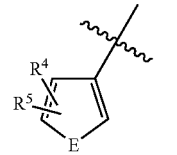

Q6

E: O, N—$R_Q^1$ or S;

$R_Q^1$:
 hydrogen, or
 each optionally substituted $C_1$-$C_4$-alkyl, CO—$C_1$-$C_4$-alkyl, $SO_2$—$C_1$-$C_4$-alkyl, CO—O—$C_1$-$C_4$-alkyl, aryl, $C_1$-$C_4$-alkylene-aryl, CO-aryl, CO-hetaryl, $SO_2$-aryl, $SO_2$-hetaryl, CO—O-aryl, CO—$C_1$-$C_4$-alkylene-aryl, $SO_2$—$C_1$-$C_4$-alkylene-aryl or CO—O—$C_1$-$C_4$-alkylene-aryl;

$R^4$, $R^5$ each independently of one another a moiety chosen from the groups 1.), 2.), 3.), 4.) or 5.):

1.) hydrogen, halogen, CN, $CF_3$, $CHF_2$, or
each optionally substituted $C_1$-$C_{10}$-alkyl, $C_2$-$C_{10}$-alkenyl, $C_2$-$C_{10}$-alkynyl, $C_3$-$C_7$-cycloalkyl, $C_1$-$C_6$-alkylene-$C_3$-$C_7$-cycloalkyl, $C_1$-$C_4$-alkylene-aryl, $C_1$-$C_4$-alkylene-hetaryl, $C_1$-$C_6$-alkylene-O—$C_1$-$C_6$-alkyl, $C_1$-$C_6$-alkylene-β-aryl, COO—$C_1$-$C_4$-alkyl or $C_1$-$C_4$-alkylene-COO—$C_1$-$C_4$-alkyl;

2.) Phenyl or naphthyl, which are each substituted with $R_Q^2$, $R_Q^3$ and $R_Q^4$, wherein
$R_Q^2$, $R_Q^3$ and $R_Q^4$ each independently of one another represent a substituent from the following group:
hydrogen, $NO_2$, $NH_2$, OH, CN, $CF_3$, $CHF_2$, $OCF_3$, $OCHF_2$, COOH, O—$CH_2$—COOH, SH, halogen, or
each optionally substituted aryl, hetaryl, heterocycloalkyl, $C_1$-$C_6$-alkyl, $C_2$-$C_6$-alkenyl, $C_2$-$C_5$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, $C_1$-$C_4$-alkylene-aryl or $C_1$-$C_4$-alkylene-hetaryl, or
O—$R_Q^5$, S—$R_Q^5$, $NR_Q^7R_Q^8$, CO—$OR_Q^6$, $NR_Q^8$—COO—O—$R_Q^6$, O—$CH_2$—COO—$R_Q^6$, $NR_Q^8$—CO—$R_Q^6$, $SO_2$—$R_Q^6$, $NR_Q^8$—$SO_2$—$R_Q^6$, $SO_2NH_2$, $CONH_2$, $SO_2$—$NR_Q^7R_Q^8$ or CO—$NR_Q^7R_Q^8$, or
two of the moieties from $R_Q^2$, $R_Q^3$ or $R_Q^4$ together form a 3 to 7-membered, optionally substituted, saturated, unsaturated carbocycle or an optionally substituted, saturated, unsaturated aromatic heterocycle, which can contain up to three further different or identical heteroatoms O, N, S, and optionally two moieties substituted on this heterocycle can together form an anellated, saturated, unsaturated or aromatic carbocycle or heterocycle, wherein the heterocycle can contain up to three different or identical heteroatoms O, N, S, and the cycle formed can optionally be substituted or a further, optionally substituted cycle can be condensed onto this cycle;

$R_Q^5$ each optionally substituted $C_1$-$C_6$-alkyl, $C_2$-$C_6$-alkenyl, $C_2$-$C_6$-alkynyl, $C_1$-$C_4$-alkylene-$C_3$-$C_7$-cycloalkyl, $C_1$-$C_4$-alkylene-heterocycloalkyl, heterocycloalkyl, aryl or hetaryl;

$R_Q^6$ each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl or $C_1$-$C_6$-alkylene-O—$C_1$-$C_6$-alkyl;

$R_Q^7$ hydrogen, OH, CN, or
each optionally substituted $C_1$-$C_6$-alkyl, $C_2$-$C_6$-alkenyl, $C_2$-$C_6$-alkenyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl, $C_1$-$C_6$-alkylene-O—$C_1$-$C_6$-alkyl, CO—$C_1$-$C_6$-alkyl, $C_1$-$C_4$-alkylene-aryl, $C_1$-$C_4$-alkylene-hetaryl, CO-aryl, CO-hetaryl, CO—$C_1$-$C_4$-alkylene-aryl, CO—$C_1$-$C_4$-alkylene-hetaryl, CO—O—$C_1$-$C_6$-alkyl, CO—O-aryl, CO-β-$C_1$-$C_4$-alkylene-aryl, CO—O-hetaryl, CO—O—$C_1$-$C_4$-alkylene-hetaryl, $SO_2$—$C_1$-$C_6$-alkyl, $SO_2$-aryl, $SO_2$-hetaryl, $SO_2$—$C_1$-$C_4$-alkylene-aryl or $SO_2$—$C_1$-$C_4$-alkylene-hetaryl;

$R_Q^8$ each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl, $C_1$-$C_6$-alkylene-O—$C_1$-$C_6$-alkyl, CO—$C_1$-$C_6$-alkyl, CO-aryl, CO-hetaryl, CO—$C_1$-$C_4$-alkylene-aryl, CO—$C_1$-$C_4$-alkylene-hetaryl, CO—O—$C_1$-$C_6$-alkyl, CO—O-aryl, CO—$C_1$-$C_4$-alkylene-aryl, CO—O-hetaryl, CO—O—$C_1$-$C_4$-alkylene-hetaryl, $SO_2$—$C_1$-$C_6$-alkyl, $SO_2$-aryl, $SO_2$-hetaryl, $SO_2$—$C_1$-$C_4$-alkylene-aryl or $SO_2$—$C_1$-$C_4$-alkylene-hetaryl;

or both moieties $R_Q^7$ and $R_Q^8$ form, together with the nitrogen, a 3 to 7-membered, optionally substituted, saturated or aromatic heterocycle, which can contain one, two or three further different or identical heteroatoms O, N, S; and optionally two moieties substituted on this heterocycle can together form an anellated, saturated, unsaturated or aromatic carbocycle or heterocycle, wherein the heterocycle can contain up to three different or identical heteroatoms O, N, S, and the cycle formed can optionally be substituted or a further, optionally substituted cycle can be condensed onto this cycle;

3.) a 5- or 6-membered hetaryl moiety optionally substituted with 1 or 2 substituents, from the group consisting of
2-furyl, 3-furyl, 2-pyrrolyl, 3-pyrrolyl, 2-thienyl, 3-thienyl, 2-pyridyl, 3-pyridyl, 4-pyridyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl or triazinyl or their anellated derivatives indazolyl, indolyl, benzothiophenyl, benzofuranyl, indolinyl, benzimidazolyl, benzthiazolyl, benzoxazolyl, chinolinyl and isochinolinyl;

4.) both moieties $R^4$ and $R^5$ together form a 4 to 7-membered, optionally substituted, saturated or unsaturated or aromatic carbocycle or a 5- or 6-membered optionally substituted, saturated or unsaturated or aromatic heterocycle which can contain up to three further different or identical heteroatoms O, N, S, and can be substituted with up to two further moieties, wherein optionally two moieties substituted on this carbo- or heterocycle can together form an anellated, saturated, unsaturated or aromatic carbocycle or heterocycle, wherein the heterocycle can contain up to three different or identical heteroatoms O, N, S and wherein the cycle formed can optionally be substituted or a further, optionally substituted cycle can be condensed onto this cycle;

5.) a $C_6$-$C_{10}$-bi- or tricyclic, saturated hydrocarbon moiety;

for the preparation of a medicament for the treatment of diseases which are modulated by a 5-HT5 receptor activity.

In this regard, the treatment of neuropathological, neuropsychiatric and neurodegenerative disorders, symptoms and dysfunctions is preferred, in particular the treatment of migraine and brain damage. Examples of brain damage and/or disorders can be cerebral ischemia, stroke, epilepsy and seizures in general, psychoses, schizophrenia, autism, OCD-syndrome, cognitive diseases, attention disorders, depressions, bipolar and/or unipolar depressions, conditions of anxiety, dementia, senile dementia, Alzheimer dementia, demyelinizing diseases, multiple sclerosis and brain tumours.

Also preferred is the treatment of cerebral vascular disorders, pain, disorders due to pain, addiction, disorders due to drugs, amnesia, alcohol abuse, drug abuse, disorders of the circadian rhythm and Cushing Syndrome.

DETAILED DESCRIPTION OF THE INVENTION

In preferred embodiments, the moieties of the formulae I or IA have the following meanings:

W is defined as given above and preferably represents W1.

A is defined as given above and preferably means
halogen, OH, CN, $CF_3$, $CHF_2$, $OCF_3$, $OCHF_2$, or
each optionally substituted $C_1$-$C_6$-alkyl or $C_2$-$C_6$-alkenyl, —O—$CH_2$—COO—$R_A^1$, O—$R_A^1$, S—$R_A^1$, $NR_A^2R_A^3$, —$NR_A^4$—CO—$R_A^1$, $SO_2NH_2$, $NR_A^4$—$SO_2$—$R_A^1$, $SO_2$—$NR_A^2R_A^3$ or —CO—$NR_A^4$—$R_A^1$.

In one embodiment A is preferably
halogen, OH, CN, $CF_3$, $CHF_2$, $OCF_3$, $OCHF_2$, or
each optionally substituted $C_1$-$C_6$-alkyl or $C_2$-$C_6$-alkenyl, —O—$CH_2$—COO—$R_A^1$, O—$R_A^1$, S—$R_A^1$, $NR_A^2R_A^3$, —$NR_A^4$—CO—$R_A^1$ or —CO—$NR_A^4$—$R_A^1$.

It is especially preferred that A is halogen, OH, $OCF_3$, $OCHF_2$, optionally substituted $C_1$-$C_4$-alkyl, O—$R_A^1$ or S—$R_A^1$. Even more preferred, A is halogen, OH, $OCF_3$, $OCHF_2$, each optionally substituted $C_1$-$C_4$-alkyl, O—$C_1$-$C_4$-alkyl, O-benzyl, O-phenyl or S—$C_1$-$C_4$-alkyl. Of these, A is even more preferably OH, F, Cl, $OCF_3$, $OCHF_2$, $C_1$-$C_4$-alkyl, O—$C_1$-$C_4$-alkyl or S—$C_1$-$C_4$-alkyl. Most preferred, A is OH, $OCF_3$, $OCH_3$, O-ethyl, O-n-propyl or O-i-propyl.

A is preferably located in the 2- or 4-position on the ring, more preferred, in the 2-position.

$R_A^1$ is defined as given above and preferably means each optionally substituted $C_1$-$C_4$-alkyl, $C_3$-$C_7$-cycloalkyl, phenyl or benzyl. More preferred $R_A^1$ is methyl, ethyl, n-propyl or i-propyl. Most preferred $R_A^1$ is methyl or ethyl.

$R_A^2$ is defined as given above and preferably means
hydrogen or
each optionally substituted $C_1$-$C_4$-alkyl, phenyl, benzyl, phenethyl, CO—$C_1$-$C_4$-alkyl, CO-aryl, CO—O—$C_1$-$C_4$-alkyl, $SO_2$—$C_1$-$C_4$-alkyl, $SO_2$-aryl, $SO_2$-hetaryl, or $SO_2$—$C_1$-$C_4$-alkylene-aryl.

Even more preferred, $R_A^2$ is hydrogen, $C_1$-$C_4$-alkyl, phenyl or benzyl.

In one embodiment, $R_A^2$ is preferably hydrogen, methyl, ethyl, n-propyl, i-propyl or phenyl.

$R_A^3$ is defined as given above and preferably means each optionally substituted $C_{1-4}$-alkyl, phenyl, benzyl, phenethyl, CO—$C_1$-$C_4$-alkyl, CO-aryl, CO—O—$C_1$-$C_4$-alkyl, $SO_2$—$C_1$-$C_4$-alkyl, $SO_2$-aryl, $SO_2$-hetaryl, or $SO_2$—$C_1$-$C_4$-alkylene-aryl.

Even more preferred, $R_A^3$ is $C_1$-$C_4$-alkyl, phenyl or benzyl, most preferred methyl, ethyl, n-propyl or i-propyl or phenyl.

As described above, both of the moieties $R_A^2$ and $R_A^3$ can also form, together with the nitrogen, a 3-7-membered heterocycle. In this regard, both of the moieties $R_A^2$ and $R_A^3$ preferably together form an optionally substituted 5- or 6-membered, saturated or unsaturated ring which can contain one or two further or identical different heteroatoms from the group O, N and S.

$R_A^4$ is defined as given above and preferably means hydrogen or an optionally substituted $C_1$-$C_4$-alkyl-moiety. Most preferred, $R_A^4$ is hydrogen, methyl, ethyl, n-propyl or i-propyl.

B is defined as given above and preferably means
hydrogen, halogen, OH, CN, $CF_3$, $CHF_2$, $OCF_3$, $OCHF_2$,
each optionally substituted $C_1$-$C_6$-alkyl or $C_2$-$C_6$-alkenyl, —O—$CH_2$—COO—$R_A^1$, O—$R_A^1$, S—$R_A^1$, $NR_A^2R_A^3$, —$NR_A^4$—CO—$R_A^1$ or —CO—$NR_A^4$—$R_A^1$.

Especially preferred, B is
hydrogen, halogen, OH, $OCF_3$, $OCHF_2$, optionally substituted $C_1$-$C_4$-alkyl, O—$R_A^1$ or S—$R_A^1$.

Even more preferred, B is hydrogen, halogen, OH, $OCF_3$, $OCHF_2$, each optionally substituted $C_1$-$C_4$-alkyl, O—$C_1$-$C_4$-alkyl, O-benzyl, O-phenyl or S—$C_1$-$C_4$-alkyl. Of these, B is even more preferably hydrogen, OH, F, Cl, $OCF_3$, $OCHF_2$, $C_1$-$C_4$-alkyl, O—$C_1$-$C_4$-alkyl or S—$C_1$-$C_4$-alkyl. Most preferred, B is hydrogen, OH, $OCF_3$, $OCH_3$, O-ethyl, O-n-propyl or O-i-propyl.

B is preferably located in the 5- or 6-position on the ring, even more preferably in the 6-position.

$R_W^1$ is defined as given above and preferably means hydrogen, F, Cl, CN, $CF_3$, $CHF_2$, O—$CF_3$, $OCHF_2$, optionally substituted $C_1$-$C_4$-alkyl, $OC_1$-$C_4$-alkyl, aryl, $C_1$-$C_6$-alkylamino or $C_1$-$C_6$-dialkylamino. Even more preferred, $R_W^1$ is hydrogen, F, Cl, CN, $CF_3$ or O—$CF_3$, OMe, most preferred hydrogen.

D is defined as given above and preferably means
halogen, OH, CN, $CF_3$, $CHF_2$, $OCF_3$, $OCHF_2$,
each optionally substituted $C_1$-$C_6$-alkyl or $C_2$-$C_6$-alkenyl, —O—$CH_2$—COO—$R_A^1$, O—$R_A^1$, S—$R_A^1$, $NR_A^2R_A^3$, —$NR_A^4$—CO—$R_A^1$ or —CO—$NR_A^4$—$R_A^1$.

It is especially preferred that D is
halogen, OH, $OCF_3$, $OCHF_2$, optionally substituted $C_1$-$C_4$-alkyl, O—$R_A^1$ or S—$R_A^1$.

Even more preferred, D is halogen, OH, $OCF_3$, $OCHF_2$, each optionally substituted $C_1$-$C_4$-alkyl, O—$C_1$-$C_4$-alkyl, O-benzyl, O-phenyl or S—$C_1$-$C_4$-alkyl.

Of these, D is even more preferably OH, F, Cl, $OCF_3$, $OCHF_2$, $C_1$-$C_4$-alkyl, O—$C_1$-$C_4$-alkyl or S—$C_1$-$C_4$-alkyl. Most preferred, D is OH, $OCF_3$, $OCH_3$, O-ethyl, O-n-propyl or O-i-propyl.

D is preferably located in the 3 or 4-position on the ring, even more preferred, in the 3-position.

In its entirety, W preferably represents a moiety which is composed of the preferred combinations of A, B, $R_A^1$, $R_A^2$, $R_A^3$, $R_A^4$ and $R_W^1$.

Z is defined as given above, wherein the sum of the indices a, b and c is 1, 2, 3, 4 or 5, preferably 1, 2 or 3, even more preferably, 1 or 2. In particular, a is 0, 1, 2, 3 or 4, preferably 1, 2 or 3, even more preferably 1 or 2. Index b is 0 or 1, preferably 0. Index c is 0, 1, 2, 3 or 4, preferably 0, 1 or 2, most preferably 0.

Z is preferably each optionally substituted $C_{1-4}$-alkylene or $C_{1-4}$-alkyleneoxy, more preferred —$CH_2$—, —$CH_2$—O—, —$CH_2$—$CH_2$—, —$CH_2$—$CH_2$—$CH_2$— or —$CH_2$—$CH_2$—O—, more preferred —$CH_2$—, —$CH_2$—O—, —$CH_2$—$CH_2$— or —$CH_2$—$CH_2$—O—, most preferred —$CH_2$—.

$R_Z^1$, $R_Z^2$, $R_Z^3$, $R_Z^4$ are defined as given above and preferably mean independently from one another hydrogen, halogen, OH or optionally substituted $C_1$-$C_6$-alkyl, even more preferably hydrogen, F or $CH_3$. Most preferably, $R_Z^1$, $R_Z^2$, $R_Z^3$ and $R_Z^4$ are simultaneously hydrogen.

$V_Z$ is defined as given above and preferably means —CO—, —CO—$NR_Z^5$—, —$NR_Z^5$—CO—, —O—, —S—, even more preferred —O— or —S—, most preferred —O—.

$R_Z^5$ and $R_Z^{5*}$ are defined as given above and preferably mean independently of one another hydrogen or $CH_3$.

$R_Z^6$ and $R_Z^7$ are defined as given above and preferably mean independently of one another hydrogen or $CH_3$, most preferred hydrogen.

$R^1$, $R^2$, $R^3$ are defined as given above and preferably mean independently of one another hydrogen, OH, CN, $C_1$-$C_4$-alkyl, $C_1$-$C_6$-alkylene-O—$C_1$-$C_6$-alkyl, optionally substituted aryl, benzyl, CO—$C_1$-$C_6$-alkyl, CO-aryl, CO—$C_1$-$C_4$-alkylene-aryl, OCO—$C_1$-$C_6$-alkyl, O—CO-aryl or O—CO—$C_1$-$C_4$-alkylene-hetaryl, CO—O—$C_1$-$C_4$-alkyl, O—CO—$C_1$-$C_4$-alkyl, CO—Obenzyl, O—CO-benzyl, more preferred hydrogen, OH, CN, O-methyl, O-phenyl, acetyl, benzoyl, O-acetyl, O-benzoyl, CO—O—$C_1$-$C_4$-alkyl, O—CO—$C_1$-$C_4$-alkyl, CO-Obenzyl, O—CO-benzyl. Especially preferred, two of the moieties $R^1$, $R^2$, or $R^3$ are hydrogen, and the third moiety is hydrogen, OH, acetyl, benzoyl, CO—O—$C_1$-$C_4$-alkyl, O—CO—$C_1$-$C_4$-alkyl, most preferred, all moieties $R^1$, $R^2$, and $R^3$ are hydrogen.

Q is defined as given above and preferably means a moiety of the formulae Q1, Q2, Q3 or Q5. In one embodiment, Q means a moiety of the formulae Q1, Q2 or Q3. Especially preferred are the moieties of the formulae

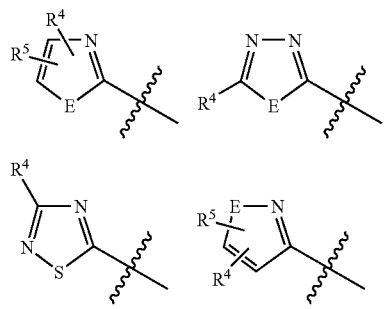

even more preferred are the moieties of the formulae

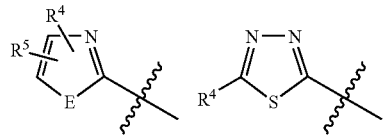

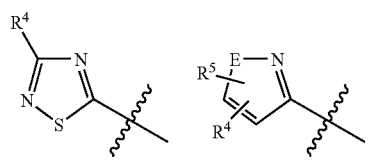

Most preferred, Q is

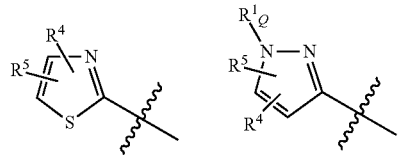

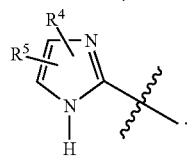

In one embodiment, the moieties of the formulae

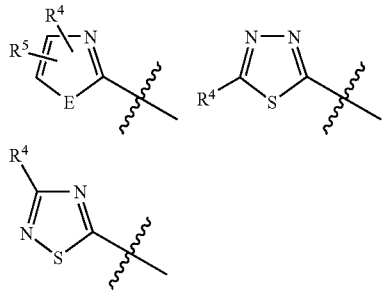

are preferred. In this embodiment, Q is most preferred

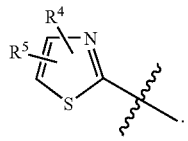

E is defined as given above and preferably means S or O, even more preferred, S.

$R_Q^1$ is defined as given above and preferably means hydrogen, optionally substituted $C_1$-$C_4$-alkyl, in the aryl moiety optionally substituted benzyl, CO—$C_1$-$C_4$-alkyl, optionally substituted benzoyl, $SO_2$—$C_1$-$C_4$-alkyl or in the aryl moiety optionally substituted $SO_2$-aryl. Even more preferred, $R_Q^1$ is hydrogen, $CH_3$, phenyl, benzyl, methanesulfonyl, phenylsulfonyl or tosyl, most preferred, hydrogen.

In a further embodiment, $R_Q^1$ is defined as given above and preferably means hydrogen, optionally substituted $C_1$-$C_4$-alkyl, in the aryl moiety optionally substituted benzyl, CO—$C_1$-$C_4$-alkyl, optionally substituted benzoyl, $SO_2$—$C_1$-$C_4$-alkyl or in the aryl moiety optionally substituted $SO_2$-aryl. Even more preferred, $R_Q^1$ is hydrogen, $CH_3$, methanesulfonyl, phenylsulfonyl or tosyl, most preferred hydrogen.

$R^4$ and $R^5$ are defined as given above and preferably have the following definitions:

For the case 1.) $R^4$ and/or $R^5$ are defined as given above, preferably each independently of one another, one moiety chosen from the group consisting of hydrogen, F, Cl, CN, $CF_3$, $CHF_2$, each optionally substituted $C_1$-$C_6$-alkyl, $C_2$-$C_6$-alkenyl, $C_1$-$C_6$-alkylene-O—$C_1$-$C_6$-alkyl or $C_3$-$C_7$-cycloalkyl. Especially preferred are hydrogen, $C_1$-$C_4$-alkyl, e.g. methyl, ethyl, n-propyl, i-propyl or tert-butyl, cyclopentyl- or cyclohexyl or $CF_3$.

For the case 2.) $R^4$ and/or $R^5$ are defined as given above, preferably phenyl, which is substituted with $R_Q^2$, $R_Q^3$ and $R_Q^4$.

$R_Q^2$, $R_Q^3$ and $R_Q^4$ are defined as given above and preferably mean each independently of one another a substituent from the following group:

hydrogen, —$NO_2$—$NH_2$, —OH, —CN, —$CF_3$, —$CHF_2$, —$OCF_3$, —$OCHF_2$, halogen, each optionally substituted aryl, hetaryl, $C_1$-$C_6$-alkyl, $C_2$-$C_6$-alkenyl, $C_3$-$C_7$-cycloalkyl, $C_1$-$C_4$-alkylene-$C_3$-$C_7$-cycloalkyl, $C_1$-$C_4$-alkylene-heterocycloalkyl, $C_1$-$C_4$-alkylene-aryl or $C_1$-$C_4$-alkylene-hetaryl;

O—$R_Q^5$, $NR_Q^7R_Q^8$, —CO—$OR_Q^6$, —$NR_Q^8$—COO—O—$R_Q^6$, —O—$CH_2$—COO—$R_Q^6$, —$NR_Q^8$—CO—$R_Q^6$, —$SO_2$—$R_Q^6$, —$NR_Q^8$—$SO_2$—$R_Q^6$, —$NR_Q^8$—COO—O—$R_Q^6$, —$SO_2NH_2$, —$CONH_2$, —$SO_2$—$NR_Q^7R_Q^8$ or —CO—

$NR_Q^7R_Q^8$. Especially preferred are hydrogen, $NH_2$, —$CHF_2$, —$CF_3$, —$OCF_3$, O—$R_Q^5$, $C_1$-$C_4$-Alkyl, —$NR_Q^7R_Q^8$ and halogen.

In one embodiment hydrogen, $CF_3$, —$OCF_3$, O—$CH_3$, —$OCHF_2$, OH, $N(CH_3)_2$, Cl and F are preferred. In another embodiment, hydrogen, $CF_3$, —$OCF_3$, O—$CH_3$, Cl and F are preferred.

It is also possible that two of the moieties $R_Q^2$, $R_Q^3$ or $R_Q^4$ together form a 3 to 7-membered, optionally substituted, saturated, unsaturated or aromatic carbocycle or an optionally substituted, saturated, unsaturated, aromatic heterocycle, which can contain up to three further different or identical heteroatoms O, N, S and optionally two moieties substituted on this heterocycle can together form an annelated, saturated, unsaturated or aromatic carbocycle or heterocycle, which can contain up to three different or identical heteroatoms O, N, S and the cycle formed can optionally be substituted or a further, optionally substituted cycle can be condensed onto this cycle. In this embodiment, $R_Q^2$, $R_Q^3$ or $R_Q^4$ preferably together form a 5- or 6-membered, even more preferred 5-membered, heterocycle, which contains a further heteroatom O, N, S, preferably O. The heterocycle is preferably saturated.

In one embodiment, $R_Q^2$, $R_Q^3$ and $R_Q^4$ are preferably each hydrogen, or two of the substituents are hydrogen and the third substituent is a moiety other than hydrogen.

$R_Q^5$ is defined as given above and preferably means each optionally substituted $C_1$-$C_6$-alkyl or $C_2$-$C_6$-alkenyl, even more preferred $C_1$-$C_4$-alkyl, which is optionally substituted with a substituent from the group consisting of F, Cl, —OH, —CN, —$CF_3$, —$CHF_2$, —$OCF_3$, —$OCHF_2$, NH—($C_{1-4}$-alkyl) and $N(C_{1-4}$-alkyl$)_2$, most preferred methyl or ethyl.

In one embodiment, $R_Q^5$ is $C_1$-$C_4$-alkyl-heterocycloalkyl, even more preferred $C_1$-$C_2$-alkyl-heterocycloalkyl, wherein the heterocycloalkyl is preferably a 5- or 6-membered ring with 1 to 3, even more preferred 1 to 2 heteroatoms, chosen from N, O or S, even more preferred, N or O. In one embodiment, $R_Q^5$ is morpholino.

$R_Q^6$ is defined as given above and preferably means each optionally substituted $C_1$-$C_6$-alkyl, $C_2$-$C_6$-alkenyl, $C_3$-$C_7$-cycloalkyl, aryl, hetaryl or $C_1$-$C_6$-alkylene-O—$C_1$-$C_6$-alkyl, even more preferred each optionally substituted $C_1$-$C_6$-alkyl, aryl, hetaryl, more preferred $C_1$-$C_4$-alkyl, $C_3$-$C_7$-cycloalkyl, aryl, or $C_1$-$C_6$-alkylene-O—$C_1$-$C_6$-alkyl, most preferred methyl, ethyl, cyclohexyl or phenyl.

$R_Q^7$ is defined as given above and preferably means
hydrogen, OH, or
each optionally substituted $C_1$-$C_6$-alkyl, $C_2$-$C_6$-alkenyl, $C_3$-$C_7$-cycloalkyl, aryl, hetaryl, $C_1$-$C_4$-alkylene-aryl, $C_1$-$C_4$-alkylene-hetaryl or $C_1$-$C_6$-alkylene-O—$C_1$-$C_6$-alkyl, more preferred hydrogen, each optionally substituted $C_1$-$C_4$-alkyl, allyl, aryl, hetaryl, benzyl, phenethyl or $CH_2$-hetaryl.

Of these, hydrogen, $C_1$-$C_4$-alkyl, phenyl, or benzyl, is even more preferred, and most preferred is hydrogen, methyl, ethyl, or phenyl.

$R_Q^8$ is defined as given above and preferably means hydrogen, each optionally substituted $C_1$-$C_6$-alkyl, $C_2$-$C_6$-alkenyl, $C_3$-$C_7$-cycloalkyl, aryl, hetaryl, $C_1$-$C_4$-alkylene-aryl, $C_1$-$C_4$-alkylene-hetaryl or $C_1$-$C_6$-alkylene-O—$C_1$-$C_6$-alkyl, CO—$C_1$-$C_4$-alkyl, $SO_2$—$C_1$-$C_4$-alkyl.

Even more preferred are hydrogen, each optionally substituted $C_1$-$C_4$-alkyl, aryl, hetaryl, benzyl, phenethyl or $CH_2$-hetaryl. Of these, even more preferred are hydrogen, $C_1$-$C_4$-alkyl, phenyl, or benzyl, and most preferred is hydrogen, methyl, ethyl, or phenyl.

It is likewise preferred that both of the moieties $R_Q^7$ and $R_Q^8$ form, together with the nitrogen, an optionally substituted 3- or 7-membered, saturated or unsaturated ring, which can contain one N or two N or one O and one N. Even more preferred, both of the moieties $R_Q^7$ and $R_Q^8$ form, together with the nitrogen, a 5- or 6-membered, optionally substituted, saturated heterocycle, which can contain a further heteroatom O, N or S, preferably O or N. Preferred are a 5-membered saturated heterocycle with one N and a 6-membered heterocycle with 2 N or 1 N and 1 O.

For the case 3.), $R^4$ and/or $R^5$ are preferably, each independent of one another, chosen from a group consisting of 2-pyrrolyl, 3-pyrrolyl, benzothiophenyl, benzofuranyl, chinolinyl, isochinolinyl each optionally substituted with 1 or 2 substituents; or 2-thienyl or 3-thienyl each optionally substituted with 1 or 2 substituents, wherein the substituents are chosen from the group consisting of halogen, in particular Cl, —$NO_2$, —$NH_2$, —OH, —CN, —$CF_3$, —$OCF_3$, —$CHF_2$, O—$CHF_2$, $C_1$-$C_6$-alkyl, in particular methyl or ethyl, O—$C_1$-$C_6$-alkyl, NH—($C_1$-$C_6$-alkyl) and $N(C_1$-$C_6$-alkyl$)_2$, NHCO—$C_1$-$C_4$-alkyl, NHSO$_2$—$C_1$-$C_4$-alkyl and $SO_2$—$C_1$-$C_4$-alkyl.

Especially preferred are benzothiophenyl, benzofuranyl, chinolinyl, isochinolinyl, 2-thienyl, or 3-thienyl, wherein both of the latter are preferably substituted with halogen, in particular $C_1$, $C_1$-$C_6$-alkyl, in particular methyl or ethyl.

In one embodiment, $R^4$ and/or $R^5$ are preferably each independently of one another 2-pyridyl, 3-pyridyl, 4-pyridyl, 2-pyrimidyl, 4-pyrimidyl, 5-pyrimidyl, 6-pyrimidyl, 2-thienyl, 3-thienyl, benzothiophenyl, benzofuranyl, benzimidazolyl, chinolinyl or isochinolinyl, even more preferred 2-pyridyl, 3-pyridyl, 4-pyridyl, 2-thienyl, 3-thienyl, benzothiophenyl, benzofuranyl, chinolinyl, or isochinolinyl, which can optionally be substituted with 1 or 2 moieties. The moieties are preferably chosen from the group consisting of halogen, in particular Cl or F, —$NO_2$, —$NH_2$, —OH, —CN, —$CF_3$, —$OCF_3$, —$CHF_2$, O—$CHF_2$, $C_1$-$C_6$-alkyl, in particular methyl or ethyl, O—$C_1$-$C_6$-alkyl, NH—($C_1$-$C_6$-alkyl) and $N(C_1$-$C_5$-alkyl$)_2$, NHCO—$C_1$-$C_4$-alkyl, NHSO$_2$—$C_1$-$C_4$-alkyl and $SO_2$—$C_1$-$C_4$-alkyl, most preferred halogen, in particular Cl or F, $C_1$-$C_6$-alkyl, in particular methyl or ethyl.

In this regard, 2-pyridyl, 3-pyridyl, 4-pyridyl or 2-pyrimidyl, in particular 2-pyridyl, 3-pyridyl or 4-pyridyl are especially preferred.

For the case 4.) both of the moieties $R^4$ and $R^5$ preferably together form one of the following rings:

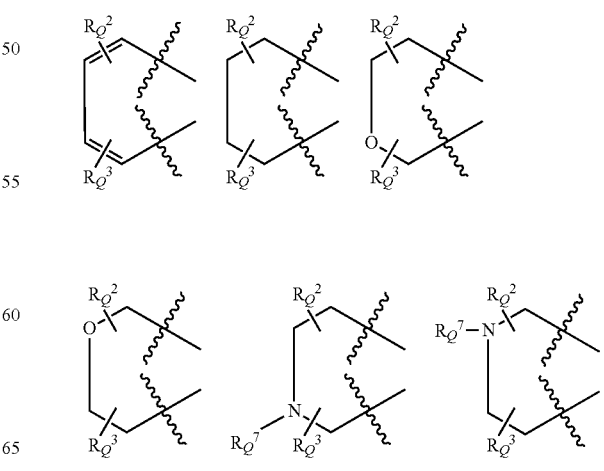

In one embodiment, both of the moieties $R^4$ and $R^5$ together preferably form one of the following rings:

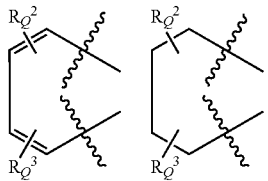

wherein $R_Q^2$, $R_Q^3$ and $R_Q^7$ are defined as under 2), including the preferred embodiments.

Most preferred, both substituents, $R_Q^2$ and $R_Q^3$ are hydrogen, or one substituent is hydrogen and the other is a substituent other than hydrogen. In this regard, the other substituent is preferably methyl or O—$C_1$-$C_3$-alkyl. It is also preferred that both substituents are methyl or that one substituent is methyl and the other is halogen.

In one embodiment, $R_Q^2$ and $R_Q^3$ together form a phenyl ring.

When both moieties $R^4$ and $R^5$ together form one of the nitrogen-containing rings given above, then $R_Q^7$ is as defined under 2), preferably hydrogen, C(O)—$C_1$-$C_4$-alkyl, $SO_2$-aryl or $C_1$-$C_4$-alkylene-aryl, even more preferred hydrogen, C(O)—$CH_3$, $SO_2$-phenyl or benzyl. Both substituents $R_Q^2$ and $R_Q^3$ on the nitrogen-containing ring are preferably hydrogen. For the case 5.), $R^4$ and/or $R^5$ are preferably Adamantyl.

Preferably, one of both of the moieties $R^4$ and $R^5$ is chosen from the group 1.), including the preferred embodiments thereof, and the other moiety is chosen from the group 1.), 2.) or 3.), including the respective preferred embodiments thereof. In this regard, the first moiety of $R^4$ and $R^5$ is preferably methyl or hydrogen.

For the case 6.), $R^4$, $R^5$ are preferably $C_1$-$C_4$-alkyl-$NH_2$, $C_1$-$C_4$-alkyl-$NR_Q^7R_Q^8$, $C_1$-$C_4$-alkyl-CO—$NR_Q^7R_Q^8$, CO—$NR_Q^7R_Q^8$ or $NR_Q^7R_Q^8$.

For the case $C_1$-$C_4$-alkyl-$NR_Q^7R_Q^8$ or $C_1$-$C_4$-alkyl-CO—$NR_Q^7R_Q^8$, $R_Q^7$ and $R_Q^8$ are defined as under 2), including the preferred embodiments. Especially preferred, $R_Q^7$ is hydrogen and $R_Q^8$ is C(O)O—$C_1$-$C_4$-alkyl, C(O)-aryl, or $SO_2$—$C_1$-$C_6$-alkyl. Alternatively, both $R_Q^7$ and $R_Q^8$ can be $C_1$-$C_4$-alkyl. By these definitions, $C_1$-$C_4$-alkyl preferably means a methylene or ethylene moiety.

For the case CO—$NR_Q^7R_Q^8$, $R_Q^7$ and $R_Q^8$ are defined as under 2), including the preferred embodiments. Especially preferred, $R_Q^7$ is hydrogen and $R_Q^8$ is $C_1$-$C_4$-alkyl, $C_2$-$C_6$-alkenyl, or $C_1$-$C_4$-alkylene-aryl, even more preferred, isopropyl, propenyl or benzyl.

Especially preferred are the moieties $CH_2NH_2$, $CH_2$—NH—C(O)O-tert-butyl, $CH_2$—NH—C(O)O-methyl, $CH_2$—NH—C(O)-phenyl, $CH_2$—NH—$SO_2$-n-butyl, $CH_2$—N(Me)$_2$, C(O)—NH—CH(CH$_3$)$_2$, C(O)—NH—$CH_2CHCH_2$, C(O)—NH—$CH_2$-phenyl.

For the case 7.), $R^4$, $R^5$ are preferably each optionally substituted azetidine-3-yl, pyrrolidine-2-yl, pyrrolidine-3-yl, piperidine-2-yl, piperidine-3-yl, piperidine-4-yl, tetrahydro-2H-pyran-4-yl, tetrahydrofuran-3-yl, azepan-4-yl, azepan-3-yl, azepan-2-yl, 1,4-diazepan-5-yl, 1,2,3,6-tetrahydropyridine-4-yl, 2,5-dihydro-1H-pyrrol-3-yl, especially preferred:

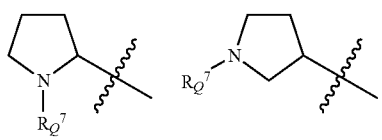

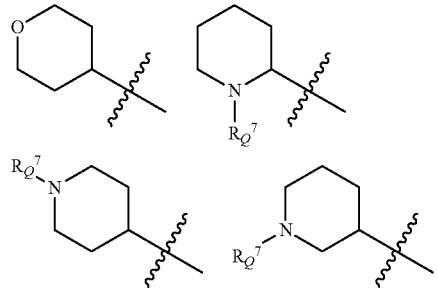

Even more preferred are

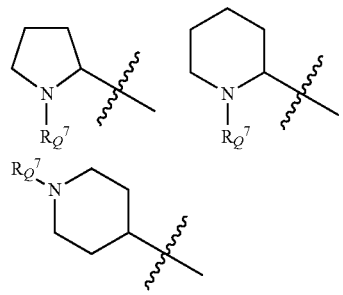

In this case, $R_Q^7$ is defined as under 2), including the preferred embodiments. Especially preferred, $R_Q^7$ is hydrogen, $C_1$-$C_4$-alkyl, C(O)—$C_1$-$C_4$-alkyl, $C_1$-$C_4$-alkylene-aryl, $SO_2$-aryl or $SO_2$—$C_1$-$C_4$-alkyl. Most preferred, $R_Q^7$ is hydrogen, methyl, isopropyl, C(O)-Me, $SO_2$-phenyl, $SO_2$-Me or benzyl.

In a preferred embodiment, one of both of the moieties $R^4$ and $R^5$ is chosen from the group 1), including the preferred embodiments of group 1, and the other moiety of $R^4$ and $R^5$ is preferably methyl or hydrogen.

In a further preferred embodiment, one of both of the moieties $R^4$ and $R^5$ is chosen from the group 2), including the preferred embodiments of group 2, and the other moiety of $R^4$ and $R^5$ is preferably methyl or hydrogen.

In one preferred embodiment, one of both of the moieties $R^4$ and $R^5$ is chosen from the group 3), including the preferred embodiments of the group 3, and the other moiety of $R^4$ and $R^5$ is preferably methyl or hydrogen.

In a further preferred embodiment, one of both of the moieties $R^4$ and $R^5$ is chosen from the group 4), including the preferred embodiments of the group 4, and the other moiety of $R^4$ and $R^5$ is preferably methyl or hydrogen.

In a further preferred embodiment, one of both of the moieties $R^4$ and $R^5$ is chosen from the group 6), including the preferred embodiments of the group 6, and the other moiety of $R^4$ and $R^5$ is preferably methyl or hydrogen.

In a further preferred embodiment, one of both of the moieties $R^4$ and $R^5$ is chosen from the group 7), including the preferred embodiments of the group 7, and the other moiety of $R^4$ and $R^5$ is preferably methyl or hydrogen.

In its entirety, Q preferably represents a moiety composed of the preferred combinations of E, $R_Q^1$, $R^4$, $R^5$, $R_Q^2$, $R_Q^3$, $R_Q^4$, $R_Q^5$, $R_Q^6$, $R_Q^7$ and $R_Q^8$.

The embodiments described above, of each moiety, including the preferred embodiments, are freely combinable with the respective embodiments of the other moieties.

In the present invention, the terms used have the meanings as described in the following:

Alkyl is a straight chain or branched, saturated hydrocarbon chain with the given number of carbon atoms, preferably 1 to 6, even more preferably 1 to 4 carbon atoms, such as methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, n-hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl, preferably methyl, ethyl, propyl, n-butyl or i-butyl.

Alkylene is an alkyl group, defined as given above, in which one hydrogen atom is replaced by a bond. Particularly noteworthy are methylene, eth-1,2-ylene, prop-1,2-ylene, prop-1,3-ylene, but-1,2-ylene, but-1,3-ylene, but-2,3-ylene, but-1,4-ylene, 2-methylprop-1,3-ylene, pent-1,2-ylene, pent-1,3-ylene, pent-1,4-ylene, pent-1,5-ylene, pent-2,3-ylene, pent-2,4-ylene, 1-methylbut-1,4-ylene, 2-methylbut-1,4-ylene, 2-methylbut-1,3-ylene, 2-ethylprop-1,3-ylene, hex-3,4-ylene, 3-methylpent-2,4-ylene, hept-3,5-ylene, 2-ethylpent-1,3-ylene, 3-ethylhept-3,5-ylene, etc., preferably methylene, eth-1,2-ylene and prop-1,2-ylene.

Cycloalkyl is a saturated, hydrocarbon ring with 3 to 7, preferably 3 to 6 carbon atoms, such as cyclopropyl, cyclobutyl, cyclopentyl, cyclohexyl or cycloheptyl.

Alkylene-O-alkyl is a straight chain or branched, saturated alkylether chain, wherein not only the alkylene moiety, but also the alkyl moiety, independently from one another, contain 1 to 6, even more preferred 1 to 4, most preferred 1 or 2, carbon atoms, wherein both moieties are as defined as above. Which contains up to a total of 2 to 12 carbon atoms and an oxygen atom: preferred examples of alkylene-O-alkyl include methoxymethylene, ethoxymethylene, t-butoxymethylene, methoxyethylene or ethoxyethylene.

Thioalkyl is a straight chain or a branched alkylenesulfanyl chain containing 1 to 6 carbon atoms and one sulfur atom. The alkylene moiety preferably contains 1 to 4, even more preferred, 1 or 2 carbon atoms, wherein alkylene is defined as given above. Examples of thioalkyl include thiomethyl or thio-tert-butyl.

Alkenyl is a branched or unbranched hydrocarbon chain containing at least one double bond with 2 to 6, preferably 2 to 4 carbon atoms. Alkenyl preferably contains one or two double bonds, most preferred one double bond. Examples of the alkenyl groups are those as given for alkyl above, wherein these groups contain one or two double bonds, such as, for example, vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-entenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl or 3-methyl-2-pentenyl.

Alkynyl is a branched or unbranched hydrocarbon chain, containing at least one triple bond with 2 to 6, preferably 2 to 4 carbon atoms. Alkynyl preferably contains one or two triple bonds, most preferred one triple bond. Examples of the alkynyl groups are those as given for alkyl above, wherein these groups contain one or two triple bonds, such as, for example, ethynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably ethynyl, 2-propynyl, 2-butynyl, 1-methyl-2-propynyl or 1-methyl-2-butynyl.

Heterocycloalkyl is a saturated alkyl ring or an alkyl ring on which a further saturated alkyl ring is anellated, with preferably 3 to 10 ring atoms in total, even more preferred 3 to 6 ring atoms, most preferred 5 or 6 ring atoms, wherein this heterocycloalkyl contains at least one heteroatom, chosen from the group O, N or S, and contains 1 to 6, preferably 1 to 5 carbon atoms. Heterocycloalkyl preferably contains 1 or 2 heteroatoms, which are preferably from N and/or O. Examples of a heterocycloalkylgroup contain, for example, N-pyrrolidinyl, N-piperidinyl, N-hexahydroazepinyl, N-morpholinyl or N-piperazinyl, wherein in heterocycles containing amino groups such as, for example, N-piperazinyl, these amino groups can be replaced by common moieties such as, for example, methyl, benzyl, boc (tert.-butoxycarbonyl), benzyloxycarbonyl, tosyl (p-toluolsulfonyl), —SO$_2$—C$_1$-C$_4$-alkyl, —SO$_2$-phenyl or —SO$_2$-benzyl.

Aryl is an aromatic mono-, bi- or polycyclic moiety with preferably 6 to 20 carbon atoms, even more preferred 6 to 10 carbon atoms, and is preferably chosen from phenyl, biphenyl, naphthyl, tetrahydronaphthyl, fluorenyl, indenyl and phenanthrenyl, even more preferred from phenyl and naphthyl, such as 1-naphthyl or 2-naphthyl. Most preferred is phenyl.

Alkylenearyl is an aryl bound via C$_1$-C$_5$—, even more preferred C$_1$-C$_4$-alkylene, and in which the aryl moiety is optionally substituted, wherein alkylene and aryl are defined as given above. Alkylenearyl is especially in the aryl moiety the optionally substituted benzyl or phenethyl.

Aryloxy or —O-aryl is an aryl bound via oxygen, the aryl being defined as given above, in particular —O-phenyl.

Hetaryl is an aromatic ring containing at least one heteroatom, preferably 1 or 2 heteroatoms, chosen from the group O, N, or S and preferably 1 to 6, even more preferred 1 to 5 carbon atoms. The aromatic ring is preferably 5- or 6-membered. Hetaryl additionally includes the derivatives thereof anellated with aryl, namely an aromatic moiety with preferably 6 to 20 carbon atoms, even more preferred 6 to 10 carbon atoms, most preferred phenyl, which is anellated with this aromatic ring, containing at least one heteroatom. Hetaryl can also be chosen from an aromatic moiety with preferably 6 to 20, even more preferred 6 to 10 carbon atoms, most preferred phenyl, with a heterocycloalkylgroup, which is anellated thereto. In this regard, the heterocycloalkylgroup is as defined above. Hetaryl is preferably chosen from 2-furyl, 3-furyl, 2-pyrrolyl, 3-pyrrolyl, 2-thienyl, 3-thienyl, 2-pyridyl, 3-pyridyl, 4-pyridyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl, triazinyl, indolinyl, benzothienyl, naphthothienyl, benzofuranyl, chromenyl, indolyl, isoindolyl, indazolyl, chinolyl, isochinolyl, phthalazinyl, chinoxalinyl, benzimidazolyl and benzoxazolyl, 2,3-dihydro-1,4-benzodioxinyl, 1,3-benzodioxolyl-, 2,1,3-benzothiadiazolyl.

Alkylenehetaryl is a hetaryl optionally substituted in the hetaryl moiety and bound via $C_1$-$C_6$—, even more preferred $C_1$-$C_4$-alkylene, wherein alkylene and hetaryl are defined as given here. Alkylenehetaryl is preferably optionally substituted —$CH_2$-2-pyridyl, —$CH_2$-3-pyridyl, —$CH_2$-4-pyridyl, —$CH_2$-2-thienyl, —$CH_2$-3-thienyl, —$CH_2$-2-thiazolyl, —$CH_2$-4-thiazolyl, $CH_2$-5-thiazolyl, —$CH_2$—$CH_2$-2-pyridyl, —$CH_2$—$CH_2$-3-pyridyl, —$CH_2$—$CH_2$-4-pyridyl, —$CH_2$—$CH_2$-2-thienyl, —$CH_2$—$CH_2$-3-thienyl, —$CH_2$—$CH_2$-2-thiazolyl, —$CH_2$—$CH_2$-4-thiazolyl or —$CH_2$—$CH_2$-5-thiazolyl.

A bi- or tricyclyc, saturated hydrocarbon moiety is a bicycloalkyl- or tricycloalkylmoiety and has 5 to 18 carbon atoms. In a bicycloalkyl moiety, the ring system preferably contains 5 to 12, even more preferably 6 to 10 carbon atoms. In a tricycloalkylmoiety the ring system preferably contains 6 to 16, even more preferably 6 to 12 carbon atoms. Examples of a bicycloalkyl moiety include indanyl, camphyl and norbornyl. Examples of a tricycloalkylmoiety include adamantyl.

Halogen is a halogen atom chosen from fluorine, chlorine, bromine or iodine, preferably fluorine, chlorine or bromine, even more preferably fluorine or chlorine.

Alkyl substituted with halogen refers to an alkyl moiety defined as given above, which is partially or completely substituted by fluorine, chlorine, bromine and/or iodine, for example $CH_2F$, $CHF_2$, $CH_2Cl$, 2-fluoroethyl, 2-chloroethyl, 2,2,2-trifluoroethyl.

If mentioned, the moieties and groups can preferably be singly or multiply, even more preferred singly, doubly or triply, most preferred singly or doubly substituted. The term "each optionally substituted" serves to make clear that not only the moiety directly following, but all the indicated moieties in a respective group, can be substituted.

Examples of the substituents include: halogen, CN, $CF_3$, $CHF_2$, $OCF_3$, $OCHF_2$, $NO_2$, $NH_2$, OH, COOH, each branched or unbranched, optionally substituted $C_1$-$C_6$-alkyl, $C_3$-$C_7$-cycloalkyl, $C_1$-$C_6$-alkylene-O—$C_1$-$C_6$-alkyl or $C_1$-$C_6$-thioalkyl, O—$C_1$-$C_4$-alkyl, N($C_1$-$C_4$-alkyl)$_2$, NH($C_1$-$C_4$-alkyl), aryl, —O-aryl, $C_1$-$C_4$-alkylene-O-aryl, NHCO—$C_1$-$C_4$-alkyl, NH—$SO_2$—$C_1$-$C_4$-alkyl, $SO_2$—$C_1$-$C_4$-alkyl, in the aryl moiety optionally substituted NHCO-aryl, $NHSO_2$-aryl, $CONH_2$, $SO_2NH_2$, $SO_2$-aryl, SO—$C_1$-$C_4$-alkyl, SO-aryl, N-pyrrolidinyl, N-piperidinyl, and N-morpholinyl. Preferred substituents are F, Cl, $CF_3$, $OCF_3$, $NH_2$, $NO_2$, OH, COOH, methoxy, acetyl, NH-acetyl and $SO_2NH_2$.

Optical Isomers—Diastereomers—Geometric Isomers—Tautomers

The guanidine compounds of the formula I or IA or their salts, can have at least one asymmetric centre and can exist as racemates and racemic mixtures, single enantiomers, diastereomeric mixtures and single diastereomeres. The present invention includes all of these stereoisomeric forms of the guanidine compounds of formula I or IA.

The guanidine compounds of formula I or IA can be separated into their single stereoisomers by conventional methods, e.g. by fractional crystallization from a suitable solvent, e.g. methanol or ethyl acetate or from a mixture thereof or by chiral chromatography using an optically active stationary phase. The absolute stereochemistry can be determined by x-ray crystallography of the crystalline products or crystalline intermediates which, if necessary, can be derivatized with a reaction component which contains an asymmetric center of a known absolute configuration.

Alternatively, any stereoisomer of a guanidine of the formula I or IA can be obtained by stereospecific synthesis using optically pure starting materials or reaction components with known absolute configuration or by asymmetric synthesis methods.

The use of an enantiomerically- or diastereomerically pure compound is preferred.

Particularly the guanidine compounds of the formula I or IA described here can also exist as different tautomers of the guanidine group wherein, as is clear to a person of ordinary skill in the art, the kind of tautomerism depends on the nature of the moieties R1, R2 and R3. Other tautomers, such as keto-enol tautomers, can also exist. All single possible tautomers, as well as mixtures thereof, are included in the guanidine compounds of formula I or IA.

Salts

The term "pharmaceutically acceptable salts" refers to salts prepared from pharmaceutically acceptable, physiologically tolerated bases or acids, including inorganic or organic bases and inorgangic or organic acids.

Salts derived from inorganic bases include aluminium, ammonium, calcium, copper, iron(II), iron(III), lithium, magnesium, manganese, potassium, sodium, zinc and the like. Especially preferred are the ammonium, calcium, lithium, magnesium, potassium and sodium salts. Salts which are derived from pharmaceutically acceptable organic non-toxic bases include salts of primary, secondary and tertiary amines, substituted amines, including naturally existing substituted amines, cyclic amines and basic ion exchange resins, such as arginine, betaine, caffeine, choline, N,N'-dibenzylethylenediamine, diethylamine, 2-diethylaminomethanol, 2-dimethylaminoethanol, ethanolamine, ethylendiamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the guanidine of the present invention is basic, salts can be prepared from pharmaceutically acceptable physiologically tolerated acids, including inorganic and organic acids. Such acids include inter alia acetic acid, phenylsulfonic acid, benzoic acid, campfer sulfonic acid, citric acid, ethane sulfonic acid, formic acid, fumaric acid, gluconic acid, glutamic acid, hydrobromic acid, hydrochloric acid, lactic acid, malic acid, maleic acid, mandelic acid, methane sulfonic acid, malonic acid, nitric acid, pantothenic acid, phosphoric acid, propionic acid, succinic acid, sulfuric acid, tartaric acid, p-toluene sulfonic acid, trifluoracetic acid and the like. Especially preferred are citric acid, fumaric acid, hydrobromic acid, hydrochloric acid, maleic acid, phosphoric acid, sulfuric acid and tartaric acid.

When reference is made to the guanidine compounds of formula I or IA, this is to mean that the pharmaceutically acceptable salts thereof are also included.

USE, FIELDS OF APPLICATION AND EFFECTS

The subject matter of the invention is also the use of guanidine compounds of the formula I or IA for the treatment of:

Depressions and/or bipolar disorders such as, for example, dythymic disorders, seasonally related disorders and/or psychotic disorders Anxiety and/or stress-related disorders such as, for example, general stress disorders, panic disorders, compulsive disorders, posttraumatic disorders, acute stress disorders and/or social phobias Memory disorders and/or Alzheimer disease Schizophrenia, psychoses, psychotic disorders and/or psychotic-related disorders Cerebrovascular disorders Pain and/or pain-related disorders, addiction and drug-related disorders, including medication-related disorders Amnesia Alcohol- and/or drug abuse, including medication abuse disorders of the circadian rhythm and/or Cushing Syndrome.

The term "disorder" in the sense according to the invention, refers to anomalies that are generally seen as disease states and which manifest themselves in the form of certain signs, symptoms and/or dysfunctions. The treatment can be directed to single disorders, in other words, anomalies or disease states, but multiple anomalies, which can possibly be causally connected to one another, can also occur together as patterns, in other words, syndromes, which can be treated according to the invention. This state can be temporary, progressive or permanent.

Compounds of the present invention can be used for the treatment or prevention of different diseases, in which 5-HT5 receptors participate in the emergence and/or progression, i.e. diseases that are modulated by a 5-HT5 receptor activity, such as mental disorders. According to the "American Psychatric Assiciation DSM-IV, Diagnostic and Statistical Manual of Mental Disorders, 4th ed., 1994", examples of such mental disorders are: attention disorders and socially disturbing behavior, learning disorders, delirium, dementia and amnesial and other cognitive disorders; disorders in connection with different substances, such as, for example, disorders in connection with alcohol consumption and alcohol induced disorders, withdrawal symptoms; schizophrenia and other psychotic disorders such as, for example schizophreniform disorder, schizoaffective disorder and delusional disorder; substance-induced psychoses; paranoid disorders, disorders induced by neuroleptics; affective disorders such as, for example, depressive disorders (major depression, dysthymic disorder, seasonal-related disorder, unspecified depressive disorder), bipolar disorders (bipolar I disorder, bipolar II disorder, cyclothymic disorder, unspecified bipolar disorder, affective disorder induced by substances (amphetamine or amphetamine-like substances), unspecified affective disorder); disorders in connection with stress, such as, for example, acute stress disorder; anxiety disorders, such as, for example, panic disorders without agoraphobia, panic disorder with agoraphobia, agoraphobia without panic disorder in the pre-history, specific phobia, social phobia, compulsive disorder, post-traumatic stress disorder, acute stress disorder, generalized anxiety disorder, substance-induced anxiety disorder; somatoform disorders such as, for example, somatization disorder, unspecified somatoform disorder, conversion disorder, pain disorder, eating disorders, sleeping disorders such as, for example, primary sleeping disorders (dyssomnia, parasomnia), sleeping disorders in connection with another mental disorder.

The subject matter of the invention is also, in particular, the use of guanidine compounds I and IA for the treatment of neuropathological, neuropsychiatric and neurodegenerative disorders.

By neuropathological disorders are, are understood disorders which are accompanied by neurological deficits, i.e. a condition characterized by symptoms of neurological loss.

According to the invention, the treatment of neurodegenerative and/or neuropsychiatric disorders is preferred. These disorders occur particularly in neuropathological disease patterns, which normally cause brain damage, for example, cerebral ischemia, stroke, epilepsy and seizures in general, chronic schizophrenia, other psychotic diseases, depression, states of anxiety, bipolar disorders, dementia, in particular Alzheimer dementia, demyelinizing diseases, in particular multiple sclerosis, brain tumours and general inflammatory processes. A further neuropathological disorder is migraine as well as the signs, symptoms and dysfunctions associated therewith.

According to a further aspect of the present invention, neuropathological disorders are treated which are attended by a glial reaction. The use, according to the invention, relates in particular to the modulation of a glial reaction. An advantageous effect of the binding partners is apparent in the preventitive or acute treatment of neurological deficits observed in patients suffering from psychiatric diseases, such as epilepsy, psychosis, e.g. psychoses of the acute exogenous reaction type or accompanying psychoses, e.g. psychoses of organic or exogenous cause, e.g. following trauma, primarily brain lesions and diffuse brain damage, by metabolic disorders, infections and endocrinopathies; endogenous psychoses, such as schizophrenia, as well as schizo-like and delusional disorders; affective disorders, such as depression, mania or manic depressive states; as well as hybrid forms of the psychoses set out above; senile dementia and senile dementia of the Alzheimer type, as well as in the treatment or prevention of demyelinization processes.

The guanidine compounds according to the invention are especially effective in the treatment of ischemic damage, e.g. due to brain and spinal cord trauma, as well as vessel occlusion or heart failure. Noteworthy here is primarily apoplexia (synonym: apoplexia cerebri, cerebral or apoplectic insult, stroke). According to the invention, the following are treatable: transitory-ischemic attacks, reversible ischemic neurological deficits, prolonged reversible ischemic neurological deficits, partial reversible ischemic neurological symptoms and signs and also persistent complete brain infarcts. According to the invention, the treatment of acute forms is especially advantageous.

The forms of neuropathological disorders preferentially treated according to the invention, are due to one or more of the following listed changes in nerve tissue: degeneration or death of neurons, in particular of the ganglia cells, e.g. tigrolysis, blurring of the nuclear membrane, cell shrinking, cytoplasm vacuolisation and incrustation, parenchyma necrosis of the brain, edema of the brain, changes of neurons due to lack of oxygen, atrophy, morphological changes such as demyelinization, in particular myelinic degeneration, perivascular infiltrates, gliotic (German: "gliöse") proliferation and/or glia scars; degeneration of the substantia nigra.

The indication to be treated according to the invention is often characterized by a progressive development, i.e. the conditions described above change over the course of time, the severity normally increases and, possibly, conditions can merge into one another or further conditions can join existing conditions. By the treatment according to the invention of neuropathological, neuropsychiatric or neurodegenerative disorders or the conditions causing these, it is possible to treat a series of further signs, symptoms, and/or dysfunctions which are connected with these disorders, i.e. especially which accompany the disease states described above. These include, e.g., shock lung, brain nerve loss, e.g., retrobulbar neuritis, eye muscle paralysis, scanning speech, spastic paralyses, symptoms of the cerebellum, disorders of sensibility, bladder and rectum, euphoria, dementia, hypokinesis and akinesis, poverty of movement, shuffling gait, bent posture of rump and limbs, pro-, retro- and lateropulsion, tremor, lacking mimic, monotone speech, depressions, apathy, labile or rigid affectivity, impeded spontaneity and decisiveness, slowed thinking, reduced associative ability; muscle atrophy.

A treatment in the sense according to the invention includes not only the treatment of acute or chronic signs, symptoms and/or dysfunctions, but also a preventitive treatment (prophylaxis), in particular as a relapse or phase prophylaxis. The treatment can be symptomatically oriented, for example as a suppression of symptoms. It can take place for a short time, be intermediately oriented, or can also be a long-term treatment, for example within the context of a maintenance therapy.

The term "binding partner for 5-HT5 receptors" describes substances which bind to 5-HT5 receptors and therefore may also be termed 5-HT5 receptor ligands.

By binding, is understood every molecular interaction between the binding partner and the receptor, in particular under physiological conditions. These are normally classical interactions, to which electrostatic attraction, hydrogen-bonding, hydrophobic bonds, van-der-Waals forces or coordinative bindings of the sort seen with metal complexes belong. In addition to the reversible molecular interactions named above, irreversible interactions between binding partner and receptor such as e.g. covalent bindings, may also be considered.

Guanidine compounds according to the invention can competitively inhibit the binding of comparative binding partners, such as 5-HT (5-hydroxytryptamine) or 5-CT (5-carboxamidotryptamine), to 5-HT5 receptors. The term competitive inhibition is understood such that the guanidine compounds according to the invention, compete with a comparative binding partner, in the present case e.g. 5-HT or 5-CT, for binding to the receptor.

According to a further embodiment, guanidine compounds according to the invention non-competitively inhibit the binding of comparative binding partners such as 5-HT (5-hydroxytryptamine) or 5-CT (5-carboxamidotryptamine), to 5-HT5 receptors. Non-competitive inhibition is understood such that guanidine compounds according to the invention modulate, in particular reduce the binding affinity of the binding of a comparative binding partner, in the present case e.g. 5-HT or 5-CT, to the receptor.

At least for the case of competitive inhibition, in other words in the case of reversible binding, the principle applies that the displacement of one binding partner by another increases with decreasing binding affinity of the one or increasing binding affinity of the other, with regard to the receptor. Guanidine compounds, according to the invention therefore expeditiously have a high binding affinity for 5-HT5 receptors. Such a binding affinity allows, on the one hand, an effective displacement of naturally occurring binding partners for 5-HT5 receptors, such as, for example, serotonin (5-hydroxytryptamine, 5-HT) itself, wherein the required concentration of guanidine compound according to the invention for a certain amount of this binding partner to bind to 5-HT5 receptors decreases with increasing binding affinity. With regard to the medical application, those guanidine compounds are therefore preferred whose binding affinity is so large that these compounds can be administered in justifiable amounts within the framework of an effective medical treatment.

One possibility to express the binding affinity is offered by the competition experiments mentioned above, with which one determines in-vitro the concentration of guanidine compound according to the invention which displaces another comparative binding partner from the receptor binding site by 50% (IC50-values). In this way one can also evaluate the competitive inhibition of the binding of 5-CT to 5-HT5 receptors, such that preferred guanidine compounds according to the invention have half-maximal inhibition constants IC50 of less than $10^{-5}$ M, preferably less than $10^{-6}$ M and in particular, less than $10^{-7}$ M. The binding affinity of guanidine compounds according to the invention can also be expressed via the inhibition constant Ki, which is generally also determined with in-vitro competition experiments. For the binding to 5-HT5 receptors guanidine compounds according to the invention preferably exhibit Ki-values of less than $10^{-6}$ M, preferably less than $10^{-7}$ M and particularly preferred less than $10^{-8}$ M.

Useful binding partners can bind to 5-HT5 with a lower, a substantially identical, or a higher affinity than to a certain receptor different from 5-HT5. As such, binding partners for 5-HT5 receptors in the context of the use according to the invention include in particular those whose binding affinity to 5-HT5 receptors is so high as compared to the affinity for 5-HT-receptors, that they are suitable in an advantageous manner for the use according to the invention. This does not necessarily require a comparatively more selective binding to 5-HT5 receptors, although selective binding partners for the 5-HT5 receptors are a special embodiment of the present invention.

For example, one can use binding partners of high affinity not only to 5-HT5, but also to other 5-HT receptors. In this context, high affinity means Ki-values normally in the range of $1 \cdot 10^{-10}$ M to $1 \cdot 10^{-6}$ M. According to a special embodiment, guanidine compounds in the high affinity range for 5-HT receptors have a binding profile which is characterized by a binding affinity to 5-HT5 which, in comparison to other binding affinities of this range, is substantially identical or only slightly less. Factors of 10 or less can be advantageous.

Guanidine compounds according to the invention have binding affinities for 5-HT5 receptors which are larger than for one or more 5-HT receptors different than 5-HT5, thus, in particular, the receptors classified in the 5-HT receptor classes 5-HT1, 5-HT2, 5-HT3, 5-HT4, 5-HT6 and 5-HT7 given above. If the binding affinity of a binding partner for 5-HT5 receptors is larger than that for a 5-HT receptor different than 5-HT5, one speaks of a selective binding of these binding partners to 5-HT5 receptors, relative to the 5-HT receptor different from 5-HT5. Special binding partners are those whose binding affinity for 5-HT5 receptors is larger than for at least one 5-HT receptor. Guanidine compounds whose binding affinity for 5-HT5 receptors is larger than for all of the 5-HT receptors different from 5-HT5, represent a further special class of guanidine compounds according to the invention.

The term "selectivity" is understood as the characteristic of a binding partner to preferably bind to 5-HT5 receptors. It is decisive for the selectivity described above that the binding affinities for, on the one hand, 5-HT5 receptors and, on the other hand, for one or more 5-HT receptors different from 5-HT5, are sufficiently different. Preferable are differences in affinity according to which binding affinity proportions of at least 2, more preferred of at least 5, especially preferred of at least 10, preferably of at least 20, especially preferred of at least 50 and in particular of at least 100 exist.

According to a further embodiment, guanidine compounds according to the invention bind, with reference to one or more 5-HT receptors different from 5-HT5, selectively to 5-HT5 receptors with the advantageous binding affinities described above.

According to a further embodiment, guanidine compounds according to the invention bind, with reference to all 5-HT receptors different from 5-HT5, selectively to 5-HT5 receptors with the advantageous binding affinities described above.

Guanidine compounds which bind to 5-HT5 receptors with the affinities and selectivities described above, and which are expressed in glia cells and in particular by astrocytes are especially preferred. According to the invention, the human receptor variant is a preferred target for guanidine compounds according to the invention.

The binding of guanidine compounds according to the invention to 5-HT5 receptors is coupled to an effector function. Binding partners can be agonistic or antagonistic as well as partially agonistic and/or partially antagonistic in function. According to the invention, compounds which completely or partially imitate the activity of 5-HT to 5-HT5 receptors, are termed agonists. According to the invention, guanidine compounds which can block the agonistic activity of 5-HT to 5-HT5 receptors are termed antagonists.

According to a special embodiment of the present invention, guanidine compounds are employed whose binding, at least to 5-HT5 receptors of h5-HT5-transfected CHO or HEK 293 or SHSY-5Y cells effects a change of the agonist-induced stimulation of the binding of GTP to membrane-bound G-proteins, a change in intracellular calcium levels, a change in the agonist-induced induction of phospholipase C activity and/or a change in the cAMP-production. Concerning the change in intracellular calcium levels, the use of guanidine compounds which effect an increase in intracellular calcium levels represents a special embodiment of the invention. This embodiment also includes guanidine compounds which are efficacious in known animal models for neurodegenerative and neuropsychiatric processes.

Preferred are guanidine compounds which, with reference to their effector function in the sense described above, are selective for 5-HT5 receptors.

Forms of Administration and Formulation

Due to their pharmacological characteristics, the guanidine compounds according to the invention are useful as active agents for therapeutic purposes. In this regard, the guanidine compounds according to the invention are preferably put into a suitable form for administration prior to administration.

Further subject matter of the present invention is therefore compositions, in particular pharmaceutical compositions which contain at least one guanidine compound according to the invention and a pharmaceutically acceptable carrier or dilution agent.

Carriers or adjuvants which are pharmaceutically acceptable are those which are known for use as such in the field of pharmacy and neighboring fields, in particular, those listed in relevant medicine books (for example, DAB (Deutsches Arzneimittelbuch), Ph. Eur. (Pharmacopoeia Europaea), BP (Baccalaureus Pharmaciae), NF (National Formulary), USP (United States Pharmacopoeia), as well as other carriers whose properties do not rule out a physiological application.

Suitable carriers and adjuvants can be the following: wetting agents; emulsifying and suspending agents; preservative agents; antioxidants; anti-irritation agents; chelate-forming agents; coating adjuvants; emulsion stabilizers; film-forming agents; gel-forming agents; scent-masking agents, taste correction agents; resins; hydrocolloids; solvents; solution mediators; neutralizing agents; permeation accelerators; pigments; quaternary ammonium compounds; fat replenishing agents and excess fat agents; ointment, cream or oil bases; silicon derivatives; spreading agents; stabilizers; sterilizing agents; suppository bases; tablet adjuvants such as binders, fillers, lubricants, degradation agents or coatings; propellants; desiccants; clouding agents; thickeners; waxes; softeners; white petrolatum oils. The form to be taken in this regard depends on the knowledge of the skilled person as, for example, illustrated in Fiedler, H. P., Lexikon der Hilfsstoffe für Pharmazie, Kosmetik and angrenzende Gebiete, $4^{th}$ Edition, Aulendorf: ECV-Editio-Kantor-Verlag, 1996.

Examples of suitable carriers and dilution agents include lactose, dextrose, sucrose, sorbitol, mannitol, starches, acacia gum, calcium phosphate, alginate, tragacanth, gelatin, calcium silicate, microcrystalline cellulose, polyvinylpyrrolidone, cellulose, water syrup, methylcellulose, methyl- and propylhydroxybenzoates, talcum, magnesium stearate, and mineral oil.

The guanidine compounds according to the invention can be formulated so as to ensure an immediate or a delayed release of the active agent to the patient.

Examples of suitable pharmaceutical compositions are solid medication forms, such as meal, powder, granulate, tablets, in particular film tablets, pastilles, sachets, cachets, dragees, capsules, such as hard and soft gelatin capsules, suppositories or vaginal medication forms, semisolid medication forms such as ointments, creams, hydrogels, pastes or patches as well as liquid medication forms such as solutions emulsions, in particular oil-in-water emulsions, suspensions, for example, lotions, preparations for injection and infusion, eye and ear drops. Implanted delivery devices can also be used for the administration of the guanidine compounds according to the invention. Moreover, liposomes or microspheres can also be used.

The compositions according to the invention can, for example, be administered via a common route.

In the preparation of compounds according to the invention the active agents are normally mixed or diluted with a suitable adjuvant, in this case also termed excipient. Excipients can be solid, semisolid or liquid materials, which serve as the vehicle, carrier or medium for the active agent. The admixing of further adjuvants normally occurs in a common manner. Steps to confer a shape, optionally in connection with mixing processes, can be performed, for example, granulation, compression and the like.

The use according to the invention of the active agents according to the invention includes in the context of the treatment a method. In this regard, an efficacious amount of at least one guanidine compound of the Formula I or IA is administered to the individual to be treated, preferably a mammal, in particular a human and also livestock or a pet, normally formulated corresponding to pharmaceutical practice.

The invention also relates to the preparation of agents for the treatment of an individual, preferably a mammal, in particular a human, livestock or a pet.

The guanidine compound of Formula I or IA or a corresponding pharmaceutical composition can be administered orally, rectally, topically, parenterally, including subcutaneously, intravenously, and intramuscularly, ocularly, pulmonarily, or nasally. An oral administration is preferred.

Effective dosing of the active agent may depend on the type of guanidine compound, the type of administration, the sickness to be treated and the severity of the sickness to be treated.

Such an effective dosing of the active agent can be determined by one of ordinary skill in the art in the field.

The dosing depends on the age, condition and weight of the patient as well as the type of application. Normally the daily dose of active agent will be between about 0.5 and 100 mg/kg body weight for oral administration and between about 0.1 and 10 mg/kg body weight for parenteral administration.

Preparation of the Guanidine Compounds

The guanidine compounds according to the invention can be prepared analogously to methods known in the literature, which are known to one of ordinary skill in the art. The synthesis of guanidine is generally described in J. Org. Chem. 1997, 9, 1053; Tetrahedron 1999, 55 (10), 713; Tetrahedron Letters 1999, 40, 53; J. Org. Chem. 2000, 65, 8080 and the literature citations given therein. The synthesis of the guanidine compounds according to the invention can proceed according to Schemes 1 or 2 under normal reaction conditions as, for example, described in Journal of Medicinal Chemistry 1997, 40, pg. 2462-2465, Journal of Medicinal Chemistry 1999, 42, pg. 2920-2926, Bioorganic & Medicinal Chemistry Letters 2001, 11, S. 523-528, Journal of Medicinal Chemistry 2000, 43, pg. 3315-3321, Journal of Organic Chemistry 1991, 56, pg. 2139-2143 or Bioorganic and Medicinal Chemistry 2003, 11, 1319-1341.

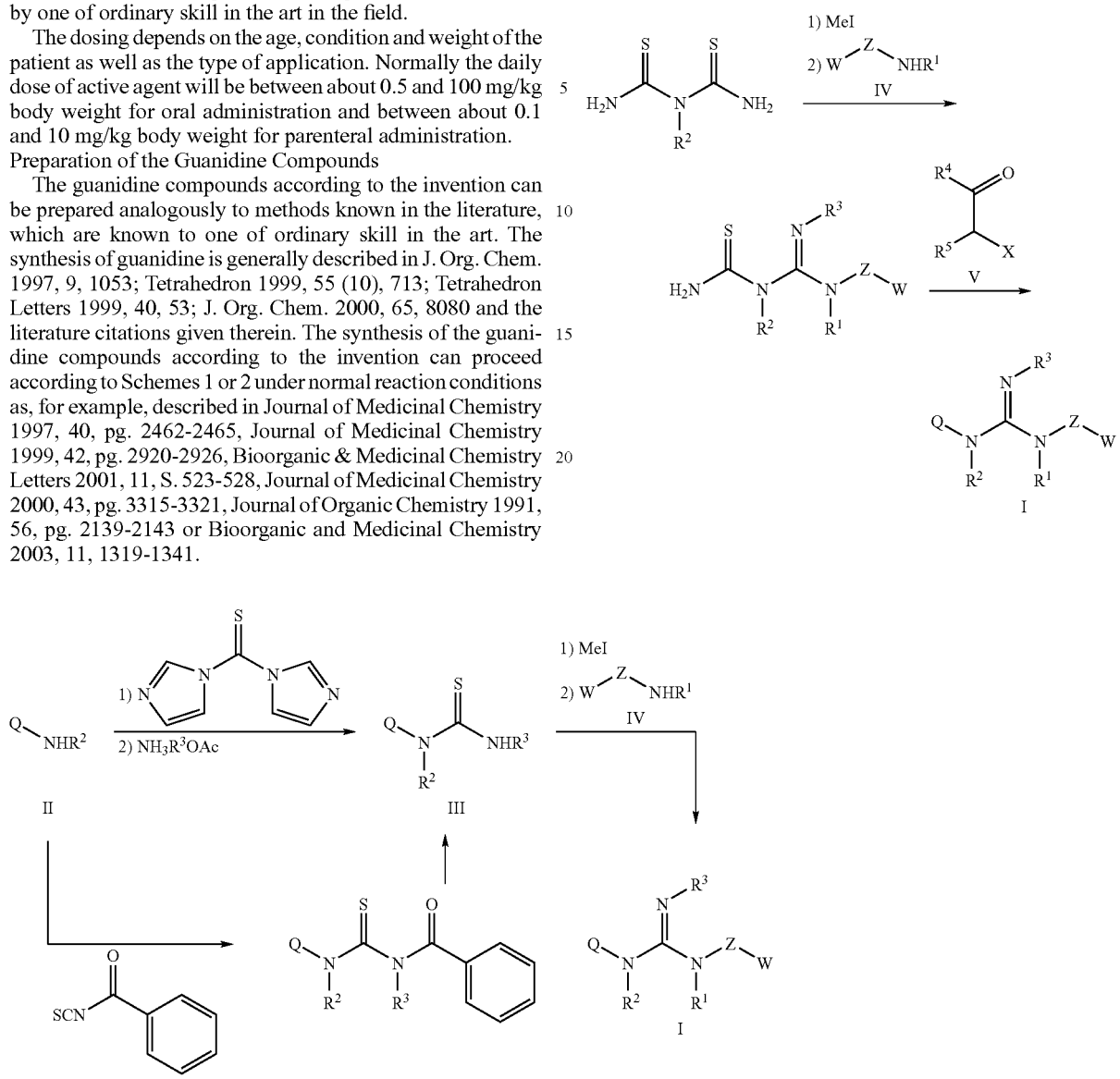

Hetaryl amines II are commercially available or producible according to methods known in the literature (for example, Houben-Weyl, Methoden der organischen Chemie, Volume E8b and E8c, Stuttgart, 1994; M. B. Smith, J. March, March's Advanced Organic Chemistry, New York, 2001). The amines IV used in the synthetic path shown in Scheme 1 are also commercially available or can be prepared according to known protocols (e.g., Houben-Weyl, Methoden der organischen Chemie, 4th Edition, Volume XI/1, Stuttgart, 1957).

For the case that the moiety Q is a substituted thiazole moiety, the guanidine compounds of the general Formula I according to the invention can be constructed in one of the last steps according to Scheme 2. For this, one uses α-haloketone V, which is commercially available or can be prepared according to the literature (e.g., Houben-Weyl, Methoden der organischen Chemie, 4th Edition, Volume VII/2c/, Stuttgart, 1977).

The use of the intermediate IVA for the preparation of the guanidines according to the invention proceeds according to methods known to one of ordinary skill in the art, as for example described in the literature cited above.

The guanidine compounds according to the invention as well as the intermediates possibly obtained can be isolated in the conventional way as well as, if necessary, purified, for example, by recrystallization from common organic solvents, preferably a short chain alcohol such as ethanol, or by chromatographic techniques.

Depending on the starting materials, the guanidine compounds according to the invention of the formula are obtained in free form or already as acid addition salts. The compounds in free form as well as salts of these compounds resulting according to the method can be transformed into desired acid addition salts or into the free form in a known manner.

The following examples illustrate the invention without restricting it. It should be noted that the notation and the formulaic representation of salts with protonated nitrogen reflects only one of many included possibilities with regard to the distribution of charge. This also applies for tautomeric forms.

PREPARATION EXAMPLES

Example 1

N-(2-methoxybenzyl)-N'-1,3-thiazole-2-ylguanidine

1.1. N-1,3-thiazole-2-yl-1H-imidazole-1-carbothioamide 35 g (349.5 mmol) of 2-aminothiazole and 62.3 g (349.5 mmol) thiocarbonyldiimidazole were stirred in 1300 ml acetonitrile for a total of four days at room temperature. Filtration of the precipitate formed and drying yielded 65.5 g of light yellow solid.

1.2. N-1,3-thiazole-2-yl-thiourea

A mixture of 65 g (309.1 mmol) N-1,3-thiazole-2-yl-1H-imidazole-1-carbothioamide and 260 g of ammonium acetate were heated to 80° C. in 400 ml ethanol for 1.5 hours; after completion of reaction the solvent was distilled off and water was added to the obtained residue. After extraction with $CH_2Cl_2$ and drying of the organic phase with $Na_2SO_4$, 59.6 g of the target product were obtained.

1.3. N-(2-methoxybenzyl)-N'-1,3-thiazole-2-ylguanidine 400 mg (2.51 mmol) N-1,3-thiazole-2-yl-thiourea were suspended in 20 ml of methanol and 392 mg (2.76 mmol) methyl iodide were added. The reaction mixture was stirred for 4 hours at reflux. Following removal of the solvent by vacuum distillation, the residue obtained was dissolved in 20 ml ethanol, 1.72 g (12.6 mmol) 2-methoxybenzylamine were added and the mixture was stirred for 20 hours at reflux. The solvent was removed on the rotovap. The residue was separated by preparative HPLC (RP-18 column, eluent water/acetonitrile/0.1% acetic acid) and 380 mg N-(2-methoxybenzyl)-N'-1,3-thiazole-2-ylguanidine were obtained.
ESI-MS [M+H$^+$]=263.15

Example 2

N-(2,6-dimethoxybenzyl)-N'-(4-phenyl-1,3-thiazole-2-yl)guanidine

2.1 N-{[(4-phenyl-1,3-thiazole-2-yl)amino]carbonothioyl}benzamide 3.10 g 2-amino-4-phenylthiazole (176 mmol) and 3.00 g benzoylisothiocyanate were heated in 50 ml acetone for 2 hours at reflux, during which a yellow solid was formed. The reaction mixture was subsequently stirred for 30 minutes at 5° C., the solid was suction-isolated and washed multiple times with n-pentane. After drying, 4.20 g of the target structure was obtained as an amorphous yellow solid.
ESI-MS [M+H$^+$]=340.05

2.2 N-(4-phenyl-1,3-thiazole-2-yl)thiourea 4.20 g N-{[(4-phenyl-1,3-thiazole-2-yl)amino]carbonothioyl}benzamide (339 mmol) were suspended in 40 ml methanol, were dissolved in aqueous sodium hydroxide (550 mg NaOH dissolved in 3 ml $H_2O$) and were heated for 3 hours at reflux. The reaction mixture was evaporation-concentrated, the residue obtained was stirred with water and the precipitated solid was suction-isolated. After drying, 2.90 g of a light yellow solid were obtained.
ESI-MS [M+H$^+$]=236.05

2.3 Methyl N'-(4-phenyl-1,3-thiazole-2-yl)imidothiocarbamate hydroiodide 2.24 g methyl iodide were added to 2.54 g N-(4-phenyl-1,3-thiazole-2-yl)thiourea (235 mmol) in 50 ml methanol and stirred for 3 hours at reflux. The reaction mixture was subsequently concentrated, the residue obtained was mixed together with n-pentane and dried. 3.90 g of product were obtained as a yellow solid, which was further reacted without further purification.
ESI-MS [M+H$^+$]=250.15

2.4 N-(2,6-dimethoxybenzyl)-N'-(4-phenyl-1,3-thiazole-2-yl)guanidine 3.00 g methyl N'-(4-phenyl-1,3-thiazole-2-yl)imidothiocarbamate hydroiodide (377 mmol) and 3.60 g 2,6-dimethoxybenzylamine (167 mmol) were dissolved in 30 ml n-propanol and heated for 2 hours at 95° C. in the microwave (radiation: 300 watt). The mixture was subsequently concentrated, the residue was dissolved in $CH_2Cl_2$, was washed with $H_2O$, 5% $NaHCO_3$— and saturated NaCl solution, was dried over $MgSO_4$, was filtered and was evaporation-concentrated. Following chromatography on silica gel (eluent: $CH_2Cl_2$/methanol 96:4) the solid obtained was recrystallized from methanol and 1.25 g of a white amorphous solid was obtained.
ESI-MS [M+H$^+$]=369.15
$^1$H-NMR (400 MHz, $CDCl_3$), δ (ppm): 3.90 (s, 6H), 4.45 (d, 2H), 6.58 (d, 2H), 6.78 (s, 1H), 7.2-7.3 (m, 5H), 7.78 (m, 2H), 7.85 (m, 2H).

Example 3

N-(2,6-dimethoxybenzyl)-N'-(4-ethyl-1,3-thiazole-2-yl)-guanidine

3.1 N-[[(2,6-dimethoxybenzyl)amino](imino)methyl]thiourea 2.00 g (14.8 mmol) dithiobiuret were placed in 25 ml methanol and 2.10 g (14.8 mmol) methyliodide were added at room temperature. The mixture was heated for 3 hours at reflux, then the solution was concentrated, was diluted with 25 ml of ethanol and 2.47 g (14.8 mmol) 2,6-dimethoxybenzylamine were added. The mixture was subsequently stirred again for 2 hours at reflux and subsequently for 30 minutes at 5° C. Filtration of the precipitate formed yielded 970 mg N-[[(2,6-dimethoxybenzyl)amino](imino)methyl]thiourea.
ESI-MS [M+H$^+$]=268.3

3.2 N-(2,6-dimethoxy-benzyl)-N'-(4-ethyl-thiazole-2-yl)-guanidine 200 mg (0.75 mmol) N-[[(2,6-dimethoxybenzyl)amino](imino)methyl]thiourea, 130 mg (0.77 mmol) 1-bromo-2-butanone and 104 mg (0.80 mmol) diisopropylethylamine were suspended in 10 ml dioxane and were stirred for 2 hours at 100° C. Following concentration of the reaction mixture, the mixture was diluted with dichloromethane, was washed with aqueous sodium chloride solution and the organic phase was dried with magnesium sulfate. After removing the drying agent and solvent, an oily residue was obtained, which was then purified on silica gel with dichloromethane/methanol. 100 mg N-(2,6-dimethoxy-benzyl)-N-(4-ethyl-thiazole-2-yl)-guanidine were obtained as a white solid by mixing with n-pentane.

ESI-MS [M+H$^+$]=269.05

The Preparation of the End Products of Formula I or IA

The compounds 4, 5, 6, 7, 8, 9, 10, 11, 12, 13, 14, 15, 16 17, 18, 20, 22, 23, 24, 26, 27, 28, 30, 92 and 93 were prepared by reaction of suitable starting materials of the Formulae II and IV analogously to Examples 1 and 2, while the compounds 19, 21, 25, 31-104 were prepared by reaction of suitable starting materials of the Formulae IV and V analogously to Example 3:

Example 4

N-(2,5-dimethylbenzyl)-N'-1,3-thiazole-2-ylguanidine hydrochloride

ESI-MS [M+H$^+$]=261.25

Example 5

N-(2,6-dimethoxybenzyl)-N'-1,3-thiazole-2-ylguanidine

ESI-MS [M+H$^+$]=293.25

Example 6

N-(2-chloro-6-methoxybenzyl)-N'-1,3-thiazole-2-ylguanidine hydrochloride

ESI-MS [M+H$^+$]=297.05

Example 7

N-(2-chlorobenzyl)-N'-1,3-thiazole-2-ylguanidine hydrochloride

ESI-MS [M+H$^+$]=267.05

Example 8

N-(2-ethoxybenzyl)-N'-1,3-thiazole-2-ylguanidine hydrochloride

ESI-MS [M+H$^+$]=277.05

Example 9

N-(2-fluoro-6-methoxybenzyl)-N'-1,3-thiazole-2-ylguanidine

ESI-MS [M+H$^+$]=281.05

Example 10

N-(2-hydroxybenzyl)-N'-1,3-thiazole-2-ylguanidine acetate

ESI-MS [M+H$^+$]=249.1

Example 11

N-(2-methoxybenzyl)-N'-1,3-thiazole-2-ylguanidine hydrochloride

ESI-MS [M+H$^+$]=277.05

Example 12

N-(2-methylbenzyl)-N'-1,3-thiazole-2-ylguanidine

ESI-MS [M+H$^+$]=247.05

Example 13

N-(3-chlorobenzyl)-N'-1,3-thiazole-2-ylguanidine hydrochloride

ESI-MS [M+H$^+$]=267.0

Example 14

N-(3-methoxybenzyl)-N'-1,3-thiazole-2-ylguanidine hydrochloride

ESI-MS [M+H$^+$]=263.1

Example 15

N-(4-methoxybenzyl)-N'-1,3-thiazole-2-ylguanidine

ESI-MS [M+H$^+$]=263.05

Example 16

N-[2-(2-methoxyphenyl)ethyl]-N'-1,3-thiazole-2-ylguanidine hydrochloride

ESI-MS [M+H$^+$]=277.1

Example 17

N-[2-(benzyloxy)benzyl]-N'-1,3-thiazole-2-ylguanidine

ESI-MS [M+H$^+$]=339.05

Example 18

N-1,3-thiazole-2-yl-N'-[2-(trifluoromethyl)benzyl]guanidine

ESI-MS [M+H$^+$]=301.0

Example 19

N-{-4-[3,5-bis(trifluoromethyl)phenyl]-1,3-thiazole-2-yl}-N'-(2,6-dimethoxybenzyl)guanidine hydrobromide

ESI-MS [M+H$^+$]=505.15

Example 20

N-[Imino(1,3-thiazole-2-ylamino)methyl]-2-methoxybenzamide

ESI-MS [M+H$^+$]=277.05

Example 21

N-[4-(2,5-dichlorophenyl)-1,3-thiazole-2-yl]-N'-(2,6-dimethoxybenzyl)guanidine hydrobromide

ESI-MS [M+H$^+$]=437.15/439.15

Example 22

N-[3-(3-{[imino(1,3-thiazole-2-ylamino)methyl]amino}propoxy)phenyl]acetamide

ESI-MS [M+H$^+$]=334.1

Example 23

N-[3-(3-acetylphenoxy)propyl]-N'-1,3-thiazole-2-ylguanidine (2E)-But-2-endioate
ESI-MS [M+H$^+$]=319.1

Example 24

N-(2-methoxybenzyl)-N'-methyl-N''-1,3-thiazole-2-ylguanidine (2E)-But-2-endioate

ESI-MS [M+H$^+$]=277.0

Example 25

N-[4-(2,3-dihydro-1,4-benzodioxin-6-yl)-1,3-thiazole-2-yl]-N'-(2,6-dimethoxybenzyl)guanidine hydrobromide

ESI-MS [M+H$^+$]=427.15

Example 26

N-ethyl-N'-(2-methoxybenzyl)-N''-1,3-thiazole-2-ylguanidine (2E)-But-2-endioate

ESI-MS [M+H$^+$]=291.0

Example 27

N-1,3-benzothiazole-2-yl-N'-(2,6-dimethoxybenzyl)guanidine (2E)-But-2-endioate
ESI-MS [M+H$^+$]=343.1

Example 28

N-1,3-benzothiazole-2-yl-N'-(2-methoxybenzyl)guanidine (2E)-But-2-endioate

ESI-MS [M+H$^+$]=313.0

Example 29

N-[2-(2-chlorophenoxy)ethyl]-N'-1,3-thiazole-2-ylguanidine (2E)-But-2-endioate

ESI-MS [M+H$^+$]=297.0

Example 30

N-(2-methoxy-benzyl)-N'-thiophene-3-yl-guanidine acetate

ESI-MS [M+H$^+$]=262.25

Example 31

N-(2-methoxybenzyl)-N'-(4-phenyl-1,3-thiazole-2-yl)guanidine

ESI-MS [M+H$^+$]=339.05

Example 32

N-(2,6-dimethoxybenzyl)-N'-(4-methyl-1,3-thiazole-2-yl)guanidine

ESI-MS [M+H$^+$]=307.25

Example 33

N-(2-methoxybenzyl)-N'-[4-(2-naphthyl)-1,3-thiazole-2-yl]guanidine

ESI-MS [M+H$^+$]=389.05

Example 34

N-(2,6-dimethoxybenzyl)-N'-[4-(2-naphthyl)-1,3-thiazole-2-yl]guanidine

ESI-MS [M+H$^+$]=419.15

Example 35

N-[4-(4-chlorophenyl)-1,3-thiazole-2-yl]-N'-(2-methoxybenzyl)guanidine

ESI-MS [M+H$^+$]=373.05

Example 36

N-(4-tert-butyl-1,3-thiazole-2-yl)-N'-(2,6-dimethoxybenzyl)guanidine

ESI-MS [M+H$^+$]=349.15

Example 37

N-(4-tert-butyl-1,3-thiazole-2-yl)-N'-(2-methoxybenzyl)guanidine (2E)-But-2-endioate

ESI-MS [M+H$^+$]=319.15

Example 38

N-[4-(4-chlorophenyl)-1,3-thiazole-2-yl]-N'-(2,6-dimethoxybenzyl)guanidine

ESI-MS [M+H$^+$]=403.25

Example 39

N-(2-methoxybenzyl)-N'-(4-methyl-1,3-thiazole-2-yl)guanidine (2E)-But-2-endioate

ESI-MS [M+H$^+$]=277.05

Example 40

N-(4,5-dimethyl-1,3-thiazole-2-yl)-N'-(2-methoxybenzyl)guanidine

ESI-MS [M+H$^+$]=291.15

Example 41

N-(2-methoxybenzyl)-N'-(4-pyridine-2-yl-1,3-thiazole-2-yl)guanidine

ESI-MS [M+H$^+$]=340.15

Example 42

N-(2,6-dimethoxybenzyl)-N'-(4-pyridine-2-yl-1,3-thiazole-2-yl)guanidine (2E)-But-2-endioate

ESI-MS [M+H$^+$]=370.15

Example 43

N-[4-(2-chlorophenyl)-1,3-thiazole-2-yl]-N'-(2-methoxybenzyl)guanidine (2E)-But-2-endioate

ESI-MS [M+H$^+$]=373.05

Example 44

N-[4-(2-chlorophenyl)-1,3-thiazole-2-yl]-N'-(2,6-dimethoxybenzyl)guanidine

ESI-MS [M+H$^+$]=403.05

Example 45

N-(2,6-dimethoxybenzyl)-N'-(4-pyridine-4-yl-1,3-thiazole-2-yl)guanidine

ESI-MS [M+H$^+$]=370.0

Example 46

N-(2-methoxybenzyl)-N'-(4-pyridine-4-yl-1,3-thiazole-2-yl)guanidine $^1$H-NMR (400 MHz, CDCl$_3$), δ (ppm): 3.85 (s, 3H), 4.40 (d, 2H), 6.95 (m, 1H), 7.15 (m, 1H), 7.25-7.80 (m, 6H), 8.55 (m, 2H).

Example 47 methyl-[2-({imino[(2-methoxybenzyl)amino]methyl}amino)-1,3-thiazole-4-yl]acetate

ESI-MS [M+H$^+$]=440.25

Example 48

N-(2-methoxybenzyl)-N'-(4-pyridine-3-yl-1,3-thiazole-2-yl)guanidine

ESI-MS [M+H$^+$]=340.15

Example 49 methyl-(2-{[[(2,6-dimethoxybenzyl)amino](imino)methyl]amino}-1,3-thiazole-4-yl)acetate

ESI-MS [M+H$^+$]=365.15

Example 50

N-(2,6-dimethoxybenzyl)-N'-(4-pyridine-3-yl-1,3-thiazole-2-yl)guanidine acetate

ESI-MS [M+H$^+$]=370.25

Example 51

2-(2-{[[(2,6-dimethoxybenzyl)amino](imino)methyl]amino}-1,3-thiazole-4-yl)-N'-(2-methoxybenzyl)acetamide(2E)-But-2-endioate

ESI-MS [M+H$^+$]=440.25

Example 52

N-(2-methoxybenzyl)-N'-[4-(trifluoromethyl)-1,3-thiazole-2-yl]guanidine (2E)-But-2-endioate

ESI-MS [M+H$^+$]=331.05

Example 53

N-(2,6-dimethoxybenzyl)-N'-[4-(trifluoromethyl)-1,3-thiazole-2-yl]guanidine

ESI-MS [M+H$^+$]=361.05

Example 54

N-(2-methoxybenzyl)-N'-(5-methyl-1,3-thiazole-2-yl)guanidine (2E)-But-2-endioate

ESI-MS [M+H$^+$]=277.25

Example 55

N-(2,6-dimethoxybenzyl)-N'-(5-methyl-1,3-thiazole-2-yl)guanidine

ESI-MS [M+H$^+$]=307.25

Example 56

N-(2,6-dimethoxybenzyl)-N'-[4-(4-fluorophenyl)-1,3-thiazole-2-yl]guanidine

ESI-MS [M+H$^+$]=387.15

Example 57

N-(2,6-dimethoxybenzyl)-N'-[4-(4-methylphenyl)-1,3-thiazole-2-yl]guanidine

ESI-MS [M+H$^+$]=383.15

Example 58

N-(2,6-dimethoxybenzyl)-N'-[4-(4-methoxyphenyl)-1,3-thiazole-2-yl]guanidine

ESI-MS [M+H$^+$]=399.15

Example 59

N-(2-fluoro-6-methoxybenzyl)-N'-(4-phenyl-1,3-thiazole-2-yl)guanidine

ESI-MS [M+H$^+$]=357.05

Example 60

N-[4-(4-cyanophenyl)-1,3-thiazole-2-yl]-N'-(2,6-dimethoxybenzyl)guanidine
ESI-MS [M+H$^+$]=394.05

Example 61

N-(2,6-dimethoxybenzyl)-N'-[4-(3-methoxyphenyl)-1,3-thiazole-2-yl]guanidine

ESI-MS [M+H$^+$]=399.15

Example 62

N-{4-[4-(diethylamino)phenyl]-1,3-thiazole-2-yl}-N'-(2,6-dimethoxybenzyl)guanidine

ESI-MS [M+H$^+$]=440.2

Example 63

N-(2,6-dimethoxybenzyl)-N'-[4-(4-pyrrolidine-1-ylphenyl)-1,3-thiazole-2-yl]guanidine hydrobromide

ESI-MS [M+H$^+$]=438.3

Example 64

N-(2,6-dimethoxybenzyl)-N'-{4-[4-(trifluoromethoxy)phenyl]-1,3-thiazole-2-yl}guanidine hydrobromide

ESI-MS [M+H$^+$]=453.05

Example 65

N-(2,6-dimethoxybenzyl)-N'-[4-(4-morpholine-4-ylphenyl)-1,3-thiazole-2-yl]guanidine hydrobromide

ESI-MS [M+H$^+$]=454.15

Example 66

N-(2,6-dimethoxybenzyl)-N'-(5-phenyl-1,3-thiazole-2-yl)guanidine hydrobromide

ESI-MS [M+H$^+$]=369.15

Example 67

N-[4-(1-benzofuran-2-yl)-1,3-thiazole-2-yl]-N'-(2,6-dimethoxybenzyl)guanidine hydrobromide
ESI-MS [M+H$^+$]=409.05

Example 68

N-[4-(3,5-difluorophenyl)-1,3-thiazole-2-yl]-N'-(2,6-dimethoxybenzyl)guanidine hydrobromide $^1$H-NMR (400 MHz, CDCl$_3$), δ (ppm)=3.83 (s, 6H), 4.53 (d, 2H), 6.78 (d, 2H), 7.24 (m, 1H), 7.38-7.45 (m, 3H), 7.99 (s, 1H), 8.34 (s wide, 2H), 9.50 (s wide, 1H), 11.90 (s wide, 1H).

Example 69

N-[4-(1,3-benzodioxol-5-yl)-1,3-thiazole-2-yl]-N'-(2,6-dimethoxybenzyl)guanidine hydrobromide

ESI-MS [M+H$^+$]=413.05

Example 70

N-(2,6-dimethoxybenzyl)-N'-[4-(2-fluorophenyl)-1,3-thiazole-2-yl]guanidine hydrobromide

ESI-MS [M+H$^+$]=387.15

Example 71

N-[4-(2-{[[(2,6-dimethoxybenzyl)amino](imino)methyl]amino}-1,3-thiazole-4-yl)phenyl]methanesulfonamide hydrobromide

ESI-MS [M+H$^+$]=462.15

Example 72

N-(2,6-dimethoxybenzyl)-N'-[4-(3-thienyl)-1,3-thiazole-2-yl]guanidine acetate

ESI-MS [M+H$^+$]=375.05

Example 73

N-(2,6-dimethoxybenzyl)-N'-[4-(3-fluorophenyl)-1,3-thiazole-2-yl]guanidine hydrobromide

ESI-MS [M+H$^+$]=387.15

Example 74

N-(4-biphenyl-4-yl-1,3-thiazole-2-yl)-N'-(2,6-dimethoxybenzyl)guanidine hydrobromide

ESI-MS [M+H$^+$]=445.15

Example 75

N-(2,6-dimethoxybenzyl)-N'-[4-(2-methoxyphenyl)-1,3-thiazole-2-yl]guanidine hydrobromide

ESI-MS [M+H$^+$]=399.15

Example 76

N-(2,6-dimethoxybenzyl)-N'-[4-(diphenylmethyl)-1,3-thiazole-2-yl]guanidine hydrobromide

ESI-MS [M+H$^+$]=459.25

Example 77

N-[4-(5-chloro-2-thienyl)-1,3-thiazole-2-yl]-N'-(2,6-dimethoxybenzyl)guanidine hydrobromide

ESI-MS [M+H$^+$]=409.05

Example 78

N-[4-(1-benzothiene-2-yl)-1,3-thiazole-2-yl]-N'-(2,6-dimethoxybenzyl)guanidine hydrobromide

ESI-MS [M+H$^+$]=425.05

Example 79

N-[4-(2-{[[(2,6-dimethoxybenzyl)amino](imino)methyl]amino}-1,3-thiazole-4-yl)phenyl]acetamide acetate

ESI-MS [M+H$^+$]=462.15

Example 80

N-(2,6-dimethoxybenzyl)-N'-8H-indeno[1,2-d][1,3]thiazole-2-ylguanidine hydrobromide

ESI-MS [M+H$^+$]=381.15

Example 81

N-(2,6-dimethoxybenzyl)-N'-(5-methyl-4-phenyl-1,3-thiazole-2-yl)guanidine hydrobromide

ESI-MS [M+H$^+$]=375.05

Example 82

N-(2,6-dimethoxybenzyl)-N'-{4-[4-(methylsulfonyl)phenyl]-1,3-thiazole-2-yl}guanidine hydrobromide

ESI-MS [M+H$^+$]=447.05

Example 83

N-(2,6-dimethoxybenzyl)-N'-[4-(3-phenylisoxazole-5-yl)-1,3-thiazole-2-yl]guanidine hydrobromide

ESI-MS [M+H$^+$]=436.15

Example 84

N-(2,6-dimethoxybenzyl)-N'-{4-[2-(trifluoromethyl)phenyl]-1,3-thiazole-2-yl}guanidine hydrobromide

ESI-MS [M+H$^+$]=437.15

Example 85

N-[4-(1-adamantyl)-1,3-thiazole-2-yl]-N'-(2,6-dimethoxybenzyl)guanidine hydrobromide

ESI-MS [M+H$^+$]=427.15

Example 86

N-(2-fluoro-6-methoxybenzyl)-N'-(4-methyl-1,3-thiazole-2-yl)guanidine

ESI-MS [M+H$^+$]=295.05

Example 87

N-[4-(3,4-difluorophenyl)-1,3-thiazole-2-yl]-N'-(2,6-dimethoxybenzyl)guanidine hydrobromide

ESI-MS [M+H$^+$]=405.15

Example 88

N-[4-(1,3-benzothiazole-2-yl)-1,3-thiazole-2-yl]-N'-(2,6-dimethoxybenzyl)guanidine hydrobromide

ESI-MS [M+H$^+$]=426.05

Example 89

N-[4-(3-chlorophenyl)-1,3-thiazole-2-yl]-N'-(2,6-dimethoxybenzyl)guanidine hydrobromide

ESI-MS [M+H$^+$]=403.05

Example 90

N-(2,6-dimethoxybenzyl)-N'-[4-(2-thienyl)-1,3-thiazole-2-yl]guanidine hydrobromide

ESI-MS [M+H$^+$]=375.05

Example 91

N-[4-(2,4-difluorophenyl)-1,3-thiazole-2-yl]-N'-(2,6-dimethoxybenzyl)guanidine hydrobromide

ESI-MS [M+H$^+$]=405.15

Example 92

N-(2-methoxybenzyl)-N'-(1-methyl-1H-benzimidazole-2-yl)guanidine

ESI-MS [M+H$^+$]=310.15

Example 93

N-1H-benzimidazole-2-yl-N'-(2-methoxybenzyl) guanidine acetate

ESI-MS [M+H$^+$]=296.15

Example 94

N-(2,6-dimethoxybenzyl)-N'-(4,5,6,7-tetrahydro-1,3-benzothiazole-2-yl)guanidine acetate

ESI-MS [M+H$^+$]=347.15

Example 95

N-(2,6-dimethoxybenzyl)-N'-[4-(4-isopropylphenyl)-1,3-thiazole-2-yl]guanidine

ESI-MS [M+H$^+$]=411.15

Example 96

N-[4-(1-benzothiene-3-yl)-1,3-thiazole-2-yl]-N'-(2,6-dimethoxybenzyl)guanidine hydrobromide

ESI-MS [M+H$^+$]=425.05

Example 97

N-(4-cyclohexyl-1,3-thiazole-2-yl)-N'-(2,6-dimethoxybenzyl)guanidine

ESI-MS [M+H$^+$]=375.15/376.15

Example 98

N-[4-(2-fluorophenyl)-1,3-thiazole-2-yl]-N'-(2-methoxybenzyl)guanidine

ESI-MS [M+H+]=357.05

Example 99

N-[4-(3-fluorophenyl)-1,3-thiazole-2-yl]-N'-(2-methoxybenzyl)guanidine

ESI-MS [M+H+]=357.05

Example 100

N-(2-methoxybenzyl)-N'-{4-[4-(trifluoromethoxy)phenyl]-1,3-thiazole-2-yl}guanidine

ESI-MS [M+H+]=423.05

Example 101

N-[4-(1,3-benzodioxol-5-yl)-1,3-thiazole-2-yl]-N'-(2-methoxybenzyl)guanidine

ESI-MS [M+H+]=383.05

Example 102

2-{[[(2,6-dimethoxybenzyl)amino](imino)methyl]amino}-N,N,4-trimethyl-1,3-thiazole-5-carboxamide

ESI-MS [M+H+]=378.15

Example 103

N-(2-methoxybenzyl)-N'-{4-[2-(trifluoromethyl)phenyl]-1,3-thiazole-2-yl}guanidine

ESI-MS [M+H+]=407.05

Example 104

N-{4-[2-({imino[(2-methoxybenzyl)amino]methyl}amino)-1,3-thiazole-4-yl]phenyl}methanesulfonamide

ESI-MS [M+H+]=432.05

Example 105

N-(2,6-dimethoxybenzyl)-N'-(3-phenyl-1,2,4-thiadiazole-5-yl)guanidine×0.5 (2E)-But-2-endioate; ESI-MS [M+H$^+$]=370.1

N-(2,6-dimethoxybenzyl)-N'-(3-phenyl-1,2,4-thiadiazole-5-yl)guanidine was prepared analogously to Example 1 with the following variations: the alkylation of N-(3-phenyl-1,2,4-thiadiazole-5-yl)thiourea with methyl iodide was performed in the presence of 1.5 equivalents triethylamine and the reaction of methyl N'-(3-phenyl-1,2,4-thiadiazole-5-yl)imidothiocarbamate proceeded with 2,6-dimethoxybenzyl amine at 140° C. in the microwave (120 watt). Following chromatographic purification, the product was converted to (2E)-but-2-endioate.

$^1$H-NMR (500 MHz, d$^6$-DMSO), δ (ppm): 3.83 (s, 6H), 4.42 (d, 2H), 6.63 (s, 1H), 6.74 (d, 2H), 7.24 (sbr, 2H), 7.34 (t, 1H), 7.44 (m, 3H), 7.96 (sbr, 2H).

$^{13}$C-NMR (100.6 MHz, d$^6$-DMSO), δ (ppm): 33.80 (t), 55.92 (q), 104.15 (2×d), 112.67 (s), 127.13, (d), 128.53 (2×d), 129.73 (d), 133.14 (s), 134.00 (2×d), 156.13 (s), 158.07 (s), 166.02 (2×s).

Example 106

N'-(2-methoxybenzyl)-N'-(3-phenyl-1,2,4-thiadiazole-5-yl)guanidine (2E)-But-2-endioate; ESI-MS [M+H$^+$]=340.1
The synthesis proceeded analogously to Example 105

Example 107

N-(2,6-dimethoxybenzyl)-N'-{4-[4-(trifluoromethyl)phenyl]-1,3-thiazole-2-yl}guanidine Preparation took place analogously to Example 3 by reaction of 140 mg (0.52 mmol) N-[[(2,6-dimethoxybenzyl)amino](imino)methyl]thiourea with 140 mg (0.52 mmol) 4-(trifluoromethyl)phenacyl bromide. The educts were suspended in 3 ml dioxane, were added to 0.3 ml acetic acid and were heated for 40 minutes in the microwave (radiation 300 Watt). The mixture was subsequently concentrated and the crude product obtained was purified by chromatography on silica gel (dichloromethane/methanol 1-4%). Stirring of the yellow foam obtained with methyl tert.-butyl ether yielded 120 mg of a white amorphous solid.

ESI-MS [M+H$^+$]=437.05.

The following were prepared analogously to Example 107:

Example 108

N-(2,6-dimethoxybenzyl)-N'-{4-[3-(trifluoromethyl)phenyl]-1,3-thiazole-2-yl}guanidine

ESI-MS [M+H$^+$]=437.05

Example 109

N-{4-[4-(difluoromethoxy)phenyl]-1,3-thiazole-2-yl}-N'-(2,6-dimethoxybenzyl)guanidine hydrobromide

ESI-MS [M+H$^+$]=435.05

Example 110

N-(2,6-dimethoxybenzyl)-N'-{4-[4-(dimethylamino)phenyl]-1,3-thiazole-2-yl}guanidine hydrobromide

ESI-MS [M+H+]=412.15

Example 111

N-(2,6-dimethoxybenzyl)-N'-[4-(4-fluoro-2-methoxyphenyl)-1,3-thiazole-2-yl]guanidine

ESI-MS [M+H+]=417.15

Example 112

N-(2,6-dimethoxybenzyl)-N'-[4-(5-fluoro-2-methoxyphenyl)-1,3-thiazole-2-yl]guanidine hydrobromide

ESI-MS [M+H+]=417.15

Example 113

N-(2,6-dimethoxybenzyl)-N'-[4-(2,6-dimethoxyphenyl)-1,3-thiazole-2-yl]guanidine

ESI-MS [M+H+]=429.15

Example 114

N-(2,6-dimethoxybenzyl)-N'-[4-(4-fluoro-1-naphthyl)-1,3-thiazole-2-yl]guanidine

ESI-MS [M+H+]=437.25

Example 115

N-[4-(2,3-dihydro-1-benzofuran-5-yl)-1,3-thiazole-2-yl]-N'-(2,6-dimethoxybenzyl)guanidine

ESI-MS [M+H+]=411.15

Example 116

N-[4-(2-chloro-4-fluorophenyl)-1,3-thiazole-2-yl]-N'-(2,6-dimethoxybenzyl)guanidine

ESI-MS [M+H+]=421.05

Example 117

N-(2,6-dimethoxybenzyl)-N'-[4-(2-furyl)-1,3-thiazole-2-yl]guanidine hydrobromide

ESI-MS [M+H+]=359.15

Example 118

N-(2,6-dimethoxybenzyl)-N'-[4-(4-fluorophenyl)-5-methyl-1,3-thiazole-2-yl]guanidine

ESI-MS [M+H+]=401.15

Example 119

N-[4-(2,6-dichlorophenyl)-1,3-thiazole-2-yl]-N'-(2,6-dimethoxybenzyl)guanidine

ESI-MS [M+H+]=439.05

Example 120 tert-butyl 2-(2-{[[(2,6-dimethoxybenzyl)amino](imino)methyl]amino}-1,3-thiazole-4-yl)pyrrolidine-1-carboxylate

ESI-MS [M+H+]=462.25

Example 121

N-(2,6-dimethoxybenzyl)-N'-[4-(4-methyl-2-thienyl)-1,3-thiazole-2-yl]guanidine

ESI-MS [M+H+]=289.05

Example 122

N-(2,6-dimethoxybenzyl)-N'-(4-pyrimidine-2-yl-1,3-thiazole-2-yl)guanidine hydrobromide

ESI-MS [M+H+]=370.85

Example 123

N-[4-(5-chloropyridine-2-yl)-1,3-thiazole-2-yl]-N'-(2,6-dimethoxybenzyl)guanidine acetate ESI-MS [M+H+]=404.25

Example 124

N-[4-(4-chloro-2-thienyl)-1,3-thiazole-2-yl]-N'-(2,6-dimethoxybenzyl)guanidine

ESI-MS [M+H+]=409.05

Example 125 tert-butyl[(2-{[[(2,6-dimethoxybenzyl)amino](imino)methyl]amino}-1,3-thiazole-4-yl)methyl]carbamate

ESI-MS [M+H+]=422.15

Example 126

N-[4-(3,5-dichloropyridine-2-yl)-1,3-thiazole-2-yl]-N'-(2,6-dimethoxybenzyl)guanidine

ESI-MS [M+H+]=440.05

Example 127

N-(4,5-dihydronaphtho[1,2-d][1,3]thiazole-2-yl)-N'-(2,6-dimethoxybenzyl)guanidine

ESI-MS [M+H+]=395.15

Example 128

N-(2,6-dimethoxybenzyl)-N'-[5-(4-fluorophenyl)-1,3-thiazole-2-yl]guanidine

ESI-MS [M+H+]=387.15

The following were prepared analogously to Example 2:

Example 129

N-(5-fluoro-2-methoxybenzyl)-N'-(4-phenyl-1,3-thiazole-2-yl)guanidine

ESI-MS [M+H+]=357.05

Example 130

N-(5-fluoro-2-methoxybenzyl)-N'-(4-methyl-1,3-thiazole-2-yl)guanidine fumarate ESI-MS [M+H+]=295.05

Example 131

N-(2,6-dimethoxybenzyl)-N'-(4-isopropyl-1,3-thiazole-2-yl)guanidine

ESI-MS [M+H+]=335.15

Example 132

N-(2-chloro-6-methoxybenzyl)-N'-(4-phenyl-1,3-thiazole-2-yl)guanidine

132.1 2-chloro-6-methoxy-benzylbromide

To 13.0 g (84.92 mmol) 3-chloro-2-methylanisole in 80 ml $CCl_4$ at reflux were added 0.4 g dibenzoyl peroxide and then, subsequently and portion-wise, a mixture of 15.2 g N-bromosuccinimide and 0.4 g dibenzoyl peroxide. After completion of reaction the mixture was evaporation-concentrated, the residue was dissolved in dichloromethane, was sequentially washed with water and saturated NaCl solution, was dried over $MgSO_4$, was filtered and again evaporation-concentrated. 20.8 yellow oil.

132.2 2-chloro-6-methoxy-benzylamine hydrochloride 13 g di-tert butyliminodicarboxylate dissolved in 40 ml DMF were added drop-wise to a suspension of 24 g NaH (60% dispersion in mineral oil; de-oiled with n-pentane) in 20 ml DMF at 5° C. After 1 hour 15 g 2-chloro-6-methoxy-benzylbromide (crude product 131.1), dissolved in DMF were added, a further 100 ml of DMF were added to the mixture and the mixture was stirred overnight at room temperature. For the workup, excess NaH was destroyed by addition of 20 ml DMF-water 1:1, the mixture was subsequently evaporation-concentrated until dry and the residue obtained was dissolved in dichloromethane, was sequentially washed with 0.1 n HCl and saturated NaCl solution, was dried over $MgSO_4$, was filtered and was evaporation-concentrated once again. Mixing of the thusly obtained oily residue with cyclohexane yielded 11.9 g of a beige solid, which were reacted further without being further purified.

For the Boc removal, 60 ml of 4 n HCL in dioxane was added to 11.6 g of solid in 60 ml dichloromethane and was heated for 2 hours at 70° C. Evaporation concentration of the reaction mixture and treatment of the obtained oil with n-pentane yielded 6.0 g of 2-chloro-6-methoxy-benzylamine hydrochloride as an amorphous solid, ESI-MS [M+H+]=172.05. For the further reactions the hydrochloride was transformed into the free base.

132.3 N-(2-chloro-6-methoxybenzyl)-N'-(4-phenyl-1,3-thiazole-2-yl)guanidine Reaction of 0.35 g methyl-N'-(4-phenyl-1,3-thiazole-2-yl)imidothiocarbamate hydroiodide (0.93 mmol) and 0.5 g 2-chloro-6-methoxy-benzylamine (2.91 mmol) analogously to Example 2, 2.4, yielded 220 mg N-(2-chloro-6-methoxy-benzyl)-N'-(4-phenyl-1,3-thiazole-2-yl)guanidine; ESI-MS [M+H+]=373.05

The following were prepared analogously to Example 132:

Example 133

N-(2-chloro-6-methoxybenzyl)-N'-(4-pyridine-2-yl-1,3-thiazole-2-yl)guanidine

ESI-MS [M+H+]=374.05

Example 134

N-(2-chloro-6-methoxybenzyl)-N'-[4-(5-chloropyridine-2-yl)-1,3-thiazole-2-yl]guanidine

ESI-MS [M+H+]=410.05

Example 135

N-(2-chloro-6-methoxybenzyl)-N'-(4-pyrimidine-2-yl-1,3-thiazole-2-yl)guanidine

ESI-MS [M+H+]=375.05

Example 136

N-(2-chloro-6-methoxybenzyl)-N'-[4-(4-fluorophenyl)-1,3-thiazole-2-yl]guanidine

ESI-MS [M+H+]=391.05

Example 137

N-[4-(5-chloropyridine-2-yl)-1,3-thiazole-2-yl]-N'-(2-methoxy-6-methylbenzyl)guanidine

137.1 2-methoxy-6-methylbenzylamine hydrochloride

The preparation proceeded analogously to Example 2; 2.4, starting from 7.1 g (41.61 mmol) 2-methoxy-6-methylbenzylchloride. Removal of Boc yielded 1.2 g 2-methoxy-6-methylbenzylamine hydrochloride as a white solid; the hydrochloride was transformed into the free base for the further reactions.

$^1$H-NMR (400 MHz, DMSO-d6), δ (ppm)=2.38 (s, 3H), 3.29 (s, 3H), 3.98 (s, 2H), 6.86 (d, 1H), 6.92 (d, 1H), 7.29 (t, 1H), 7.45 (s wide, 3H).

137.2 N-[4-(5-chloropyridine-2-yl)-1,3-thiazole-2-yl]-N'-(2-methoxy-6-methylbenzyl)guanidine The reaction proceeded analogously to Example 2, 2.4, starting from 260 mg (0.63 mmol) methyl-N'-[(4-(5-chloropyridine-2-yl)-1,3-thiazole-2-yl]imidothiocarbamate hydroiodide with 260 mg (1.39 mmol) 2-methoxy-6-methylbenzylamine hydrochloride; after purification 64 mg of the target product were obtained as a white solid.

$^1$H-NMR (400 MHz, DMSO-d6), δ (ppm)=2.48 (s, 3H), 3.85 (s, 3H), 4.75 (d, 2H), 6.89 (d, 1H), 6.99 (d, 1H), 7.29 (m, 1H), 7.40 (m, 1H), 7.73 (s, 1H), 7.91 (dd, 1H), 8.61 (d, 1H), 9.81 (s wide, 1H), 11.68 (s wide, 1H).

The following were prepared in an analogous manner:

Example 138

N-[4-(4-fluorophenyl)-1,3-thiazole-2-yl]-N'-(2-methoxy-6-methylbenzyl)guanidine

ESI-MS [M+H+]=371.15

Example 139

N-(2-methoxy-6-methylbenzyl)-N'-(4-pyrimidine-2-yl-1,3-thiazole-2-yl)guanidine

ESI-MS [M+H+]=355.05

Example 140

N-(2-methoxy-6-methylbenzyl)-N'-(4-pyridine-2-yl-1,3-thiazole-2-yl)guanidine

ESI-MS [M+H+]=354.15

Example 141

N-(2-fluoro-6-methoxybenzyl)-N'-[4-(4-fluorophenyl)-1,3-thiazole-2-yl]guanidine

ESI-MS [M+H+]=375.15

Example 142

N-(2,6-dimethoxybenzyl)-N'-[4-(4-fluoro-2-hydroxyphenyl)-1,3-thiazole-2-yl]guanidine

142.1 2-bromo-1-(4-fluoro-2-hydroxyphenyl)ethanone

To 450 mg (2.92 mmol) 2-fluorohydroxyacetophenone in 5 ml diethoxyethane were added 2.5 g CuBr$_2$ and were heated for 1 hour at 120° C. in the microwave. Filtration of the mixture over Celite and evaporation concentration yielded 870 mg of red oil, which was directly used further.

142.2 N-(2,6-dimethoxybenzyl)-N'-[4-(4-fluoro-2-hydroxyphenyl)-1,3-thiazole-2-yl]guanidine Reaction analogously to Example 107 yielded the target product; 188 mg; ESI-MS [M+H+]=403.25.

Example 143

N-(2,6-dimethoxybenzyl)-N'-[4-(4-fluorobenzyl)-1,3-thiazole-2-yl]guanidine

Production analogously to Example 3, 3.2; the isolated crude product was purified by chromatography on RP-silica gel (Chromabond column, acetonitrile/water+0.1% glacial acetic acid; 0-100%). After lyophilization 1 mg of the target product was obtained as a white solid; ESI-MS [M+H+]=401.15.

Example 144

N-(2,6-dimethoxybenzyl)-N'-[4-(5-fluoropyridine-2-yl)-1,3-thiazole-2-yl]guanidine

144.1 1-(5-fluoropyridine-2-yl)ethanone 1 g (5.68 mmol) 2-bromo-5-fluoropyridine, 160 mg dichlorobis(triphenylphosphine) palladium and 170 mg CuI were suspended in baked flasks under protective gas in 30 ml acetonitrile, 6.09 g (16.87 mmol) (1-ethoxyvinyl)-tributylstannane were added, the mixture was heated 8 hours at reflux, 200 ml 1.5 n HCl were subsequently added and reflux was continued for an additional hour. For workup the mixture was neutralized with saturated NaHCO$_3$ solution, was extracted 3× with ethyl acetate, the combined organic phases were washed with saturated NaCl solution and were dried with MgSO$_4$. After filtration 30 ml saturated KF solution were added, the mixture was filtered over Celite and evaporation-concentrated. Purification by chromatography on silica gel (dichloromethane/methanol 0-3%) yielded 120 mg 1-(5-fluoropyridine-2-yl)ethanone as an oil, which was directly reacted further.

$^1$H-NMR (400 MHz, DMSO-d6), δ (ppm)=2.65 (s, 3H), 7.92 (m, 1H), 8.18 (dd, 1H), 8.74 (d, 1H).

144.2 2-bromo-1-(5-fluoropyridine-2-yl)ethanone 100 mg 1-(5-fluoropyridine-2-yl)ethanone, 500 mg polymer-bound tribromide (1 mmol Br$_3^-$/g, Aldrich) and 0.05 ml glacial acetic acid in 5 ml THF were shaken for approximately 24 hours at room temperature. Filtration and evaporation concentration yielded 150 mg of the desired bromide as a yellow oil, which was reacted further without further purification.

144.3 N-(2,6-dimethoxybenzyl)-N'-[4-(5-fluoropyridine-2-yl)-1,3-thiazole-2-yl]guanidine The transformation proceeded analogously to Example 107; 83 mg of the target product were isolated; ESI-MS [M+H+]=388.15.

Example 145

N-[4-(3,5-difluoropyridine-2-yl)-1,3-thiazole-2-yl]-N'-(2,6-dimethoxybenzyl)guanidine 145.1 1-(3,5-difluoropyridine-2-yl)ethanone Methylmagnesium bromide (10 ml of a 3N solution in diethylether) were added drop-wise with stirring to a solution of 15 g (10.71 mmol) 2-cyano-3,5-difluoropyridine in 100 ml THF at 0° C. and the mixture was subsequently stirred at room temperature until reaction was complete. For workup the mixture was acidified with 10% $H_2SO_4$ to pH 4, was subsequently made basic with 25% $NH_4OH$, was extracted 2× with dichloromethane, and the combined organic phases were dried with $MgSO_4$. Purification by chromatography on silica gel (dichloromethane/methanol 0-5%) yielded 500 mg of a light colored oil, which crystallized upon being left to stand.

$^1$H-NMR (400 MHz, DMSO-d6), δ (ppm)=2.62 (sm 3H), 8.11 (m, 1H), 8.86 (d, 1H).

145.2 2-bromo-1-(3,5-difluoropyridine-2-yl)ethanone

The bromination was performed analogously to Example 144.2, and the bromide obtained were reacted directly further.

145.3 N-[4-(3,5-difluoropyridine-2-yl)-1,3-thiazole-2-yl]-N'-(2,6-dimethoxybenzyl)guanidine The transformation proceeded analogously to Example 107; 90 mg of the target product was isolated as a light colored solid; ESI-MS [M+H+]=406.05.

Example 146

N-[(2-methoxy-1-naphthyl)methyl]-N'-(4-phenyl-1,3-thiazole-2-yl)guanidine

The preparation proceeded analogously to Example 2; ESI-MS [M+H+]=389.15.

Example 147

N-(2,6-dimethoxybenzyl)-N'-(4-pyrrolidine-2-yl-1,3-thiazole-2-yl)guanidine hydrochloride To 490 mg (1.06 mmol) tert-butyl 2-(2-{[[(2,6-dimethoxybenzyl)amino](imino)methyl]amino}-1,3-thiazole-4-yl)pyrrolidine-1-carboxylate from Example 120 in 20 ml dioxane were added 5 ml 4N HCl in dioxane at room temperature and the mixture was stirred for 3 hours. Chromatography on RP-silica gel of the crude product obtained following concentration (Chromabond column, acetonitrile/water+0.1% glacial acetic acid; 0-100%) yielded 240 mg of the target product as a light colored solid; ESI-MS [M+H+]=362.15.

Example 148

N-[4-(1-acetylpyrrolidine-2-yl)-1,3-thiazole-2-yl]N'-(2,6-dimethoxybenzyl)guanidine A mixture of 100 mg (0.25 mmol) N-(2,6-dimethoxybenzyl)-N'-(4-pyrrolidine-2-yl-1,3-thiazole-2-yl)guanidine hydrochloride, Example 147, 0.021 ml acetyl chloride and 0.04 ml pyridine in 10 ml THF were stirred for 1 hour at 5° C. and then 4 hours at room temperature. Chromatography of the crude product on RP-silica gel (Chromabond column, acetonitrile/water+0.1% glacial acetic acid; 0-100%) yielded 33 mg of the desired product; ESI-MS [M+H+]=404.15.

Example 149

N-(2,6-dimethoxybenzyl)-N'-[4-(1-methylpyrrolidine-2-yl)-1,3-thiazole-2-yl]guanidine To 72 mg (0.2 mmol) N-(2,6-dimethoxybenzyl)-N'-(4-pyrrolidine-2-yl-1,3-thiazole-2-yl)guanidine hydrochloride, Example 147, and 20 mg formaline (37% aqueous solution) were added 51 mg of sodium triacetoxyborohydride at 10° C., the mixture was then stirred for 30 minutes at 10° C. and 2 hours at room temperature. For workup, the mixture was evaporation-concentrated, the residue was dissolved in dichloromethane, was washed with water, was dried and was concentrated once again. Following chromatography of the crude product on RP-silica gel (Chromabond column, acetonitrile/water+0.1% glacial acetic acid; 0-100%), 22 mg of a white solid were obtained, ESI-MS [M+H+]=376.15.

Example 150

N-(2,6-dimethoxybenzyl)-N'-{4-[1-(phenylsulfonyl)pyrrolidine-2-yl]-1,3-thiazole-2-yl}guanidine Reaction of 170 mg (0.38 mmol) N-(2,6-dimethoxybenzyl)-N'-(4-pyrrolidine-2-yl-1,3-thiazole-2-yl)guanidine hydrochloride, Example 147, with 68.85 mg phenylsulfonic acid chloride and 0.12 ml triethylamine in 15 ml acetonitrile and purification of the crude product by chromatography on silica gel (dichloromethane/methanol 0-5%) yielded 70 mg of the desired product as a white solid; ESI-MS [M+H+]=502.45

Example 151

N-[4-(1-benzylpyrrolidine-2-yl)-1,3-thiazole-2-yl]-N'-(2,6-dimethoxybenzyl)guanidine 177 mg N-(2,6-dimethoxybenzyl)-N'-(4-pyrrolidine-2-yl-1,3-thiazole-2-yl)guanidine, Example 147 free base, 100 mg of benzyl bromide and 870 mg polymer-bound triazabicyclodecene (1.3 mmol/g, Argonaut) were shaken in 20 ml acetonitrile overnight at room temperature. Chromatography on silica gel (dichloromethane/methanol 0-5%) of the residue obtained following evaporation concentration yielded 112 mg of a white solid; ESI-MS [M+H+]=452.15.

Example 152

N-(2-chloro-6-methoxybenzyl)-N'-[4-(3,5-difluoropyridine-2-yl)-1,3-thiazole-2-yl]guanidine Reaction of 130 mg (0.31 mmol) methyl-N'{[4-(3,5-difluoropyridine-2-yl)-1,3-thiazole-2-yl]imidothiocarbamate hydroiodide, preparation analogously to Example 2.3, with 120 mg 2-chloro-6-methoxybenzylamine analogously to Example 2.4 and stirring of the crude product obtained in methyl-tert butylether yielded 33 mg of the target product.

$^1$H-NMR (400 MHz, DMSO-d6), δ (ppm)=3.87 (s, 3H), 4.52 (d, 2H), 7.09 (m, 3H), 7.36 (m, 3H), 8.95 (m, 1H), 8.52 (s, 1H).

Example 153

N-(2,6-dimethoxybenzyl)-N'-{4-[4-fluoro-2-(2-morpholine-4-ylethoxy)phenyl]-1,3-thiazole-2-yl}guanidine 153.1 1-[4-fluoro-2-(2-morpholine-4-ylethoxy)phenyl]ethanone 0.5 g (3.24 mmol) 4-fluoro-2-hydroxyacetophenone, 720 mg (3.87 mmol) N-(2-chloroethyl)morpholine hydrochloride, 900 mg $K_2CO_3$ and a catalytic amount of NaI in 20 ml acetone were heated for 20 hours at reflux. The mixture was concentrated, was dissolved in dichloromethane, was washed with water and saturated NaCl solution, was dried and was concentrated once again. Chromatography of the crude product on silica gel (dichloromethane/methanol 0-4%) yielded 730 mg of a clear, colorless oil; ESI-MS [M+H+]=268.15.

153.2 150 mg (0.56 mmol) 1-[4-fluoro-2-(2-morpholine-4-ylethoxy)phenyl]ethanone were brominated analogously to Example 144.2; the oil obtained after evaporation concentration was reacted directly further.

153.3 N-(2,6-dimethoxybenzyl)-N'-{4-[4-fluoro-2-(2-morpholine-4-ylethoxy)phenyl]-1,3-thiazole-2-yl}guanidine Reaction analogously to Example 3 yielded the desired product as a white solid; 66 mg; ESI-MS [M+H+]=516.15.

Example 154

N-[4-(aminomethyl)-1,3-thiazole-2-yl]-N'-(2,6-dimethoxybenzyl)guanidine hydrochloride Removal of the Boc group starting from 675 mg (1.6 mmol) tert-butyl[(2-{[[(2,6-dimethoxybenzyl)amino](imino)methyl]amino}-1,3-thiazole-4-yl)methyl]carbamate analogously to Example 147 yielded 570 mg of solid; ESI-MS [M+H+]=422.15.

Example 155

N-[(2-{[[(2,6-dimethoxybenzyl)amino](imino)methyl]amino}-1,3-thiazole-4-yl)methyl]benzamide Reaction of 50 mg (0.16 mmol) N-[4-(aminomethyl)-1,3-thiazole-2-yl]-N'-(2,6-dimethoxybenzyl)guanidine hydrochloride, with 24.2 mg benzoylchloride in 5 ml THF with addition of 230 mg polymer-bound NMM (1.7 mmol/g; Argonaut) and chromatography of the crude product on silica gel dichloromethane/methanol 0-2%) yielded 20 mg; ESI-MS [M+H+]=426.15.

Example 156

N-(2,6-dimethoxybenzyl)-N'-[4-(1-isopropylpyrrolidine-2-yl)-1,3-thiazole-2-yl]guanidine Reductive amination of 100 mg (0.28 mmol) N-[4-(aminomethyl)-1,3-thiazole-2-yl]-N'-(2,6-dimethoxybenzyl) guanidine hydrochloride, Example 154 free base, with 0.04 ml acetone and 120 mg sodium triacetoxyborohydride in 10 ml acetonitrile analogously to Example 149 yielded the target product as a white solid; 52 mg; ESI-MS [M+H+]=404.15.

Example 157

N-[(2-{[[(2,6-dimethoxybenzyl)amino](imino)methyl]amino}-1,3-thiazole-4-yl)methyl]butane-1-sulfonamide Reaction of 100 mg (0.33 mmol) N-[4-(aminomethyl)-1,3-thiazole-2-yl]-N'-(2,6-dimethoxybenzyl)guanidine hydrochloride, Example 154 free base, with 60.4 mg butane sulfonic acid chloride in 5 ml THF with addition of 480 mg polymer-bound NMM (1.7 mmol/g; Argonaut) and chromatography of the crude product on silica gel dichloromethane/methanol 0-2%) yielded 46 mg; ESI-MS [M+H+]=442.05.

Example 158

N-(2,6-Dimethoxybenzyl)-N'-{4-[(dimethylamino)methyl]-1,3-thiazole-2-yl}guanidine acetate Reductive amination of N-[4-(aminomethyl)-1,3-thiazole-2-yl]-N'-(2,6-dimethoxybenzyl)guanidine hydrochloride, Example 154 free base, analogously to Example 149 in 5 ml DMF using polymer-bound MP-triacetoxyborohydride (2 mmol/g, Argonaut) yielded 24 mg of target product; ESI-MS [M+H+]=350.15.

Example 159

Methyl[(2-{[[(2,6-dimethoxybenzyl)amino](imino)methyl]amino}-1,3-thiazole-4-yl)methyl]carbamate To 360 mg (1.12 mmol) N-[4-(aminomethyl)-1,3-thiazole-2-yl]-N'-(2,6-dimethoxybenzyl)guanidine hydrochloride, Example 154 free base, in 13.5 ml THF were added 0.2 ml NMM, and 0.1 ml chloroformic acid methyl ester in 1.5 ml THF were added drop-wise with stirring. Following completion of the reaction, the mixture was concentrated, was diluted with dichloromethane, was washed with saturated NaCl solution, was dried and was concentrated. Chromatography of the crude product on silica gel (dichloromethane/methanol 0-1%) yielded 140 mg; ESI-MS [M+H+]=380.05.

Example 160 methyl-2-{[[(2,6-dimethoxybenzyl)amino](imino)methyl]amino}-4-(4-fluorophenyl)-1,3-thiazole-5-carboxylate Bromination of 800 mg (4.08 mmol) methyl-4-fluorobenzoylacetate analogously to Example 144.2 and further reaction with thiazole analogously to Example 3 yielded 27 mg.

¹H-NMR (400 MHz, DMSO-d6), δ (ppm)=3.68 (s, 3H), 3.78 (s, 6H), 4.34 (m wide, 2H), 6.69 (d, 2H), 7.20 (m, 2H), 7.32 (m, 1H), superimposed 6.95-7.40 (m, 2H), 7.63 (m wide, 2H).

Example 161

Tert-butyl 4-(2-{[[(2,6-dimethoxybenzyl)amino](imino)methyl]amino}-1,3-thiazole-4-yl)piperidine-1-carboxylate

ESI-MS [M+H+]=476.15

Example 162

N-(2,6-dimethoxybenzyl)-N'-(4-piperidine-4-yl-1,3-thiazole-2-yl)guanidine hydrochloride Removal of the Boc group starting from 490 mg (1.0 mmol) tert-butyl 4-(2-{[[(2,6-dimethoxybenzyl)amino](imino)methyl]amino}-1,3-thiazole-4-yl)piperidine-1-carboxylate analogously to Example 147 yielded 380 mg of a solid; ESI-MS [M+H+]=376.1

Example 163

N-(2,6-dimethoxybenzyl)-N'-{4-[1-(methylsulfonyl)piperidine-4-yl]-1,3-thiazole-2-yl}guanidine

ESI-MS [M+H+]=454.05

Example 164

N-[4-(3-chloropyridine-2-yl)-1,3-thiazole-2-yl]-N'-(2,6-dimethoxybenzyl)guanidine

164.1 1-(3-chloropyridine-2-yl)ethanone

Grignard reaction starting from 0.5 g (0.61 mmol) 2-cyano-3-chloropyridine analogously to Example 145.1 yielded 360 mg of the desired product as a light yellow oil.
¹H-NMR (400 MHz, DMSO-d6), δ (ppm)=2.65 (s, 3H), 7.66 (m, 1H), 8.08 (m, 1H), 8.64 (m, 1H).

164.2 N-[4-(3-chloropyridine-2-yl)-1,3-thiazole-2-yl]-N'-(2,6-dimethoxybenzyl)guanidine Bromination analogously to Example 144.2 and further reaction of the corresponding 2-bromo-1-(3-chloropyridine-2-yl)ethanone analogously to Example 3 yielded 110 mg of target product as a light colored solid; ESI-MS [M+H+]=404.25

Example 165

N-(2,6-dimethoxybenzyl)-N'-[4-(8-fluorochinoline-4-yl)-1,3-thiazole-2-yl]guanidine

165.1 8-fluorochinoline-4-yl trifluoromethane sulfonate 4.9 g trifluoromethane sulfonic acid anhydride dissolved in 5 ml dichloromethane were added drop-wise to 1.9 g (11.65 mmol) 8-fluoro-4-hydroxychinoline and 4.7 ml triethylamine in 15 ml dichloromethane and the mixture was stirred for approximately 20 minutes at 5° C. For workup the mixture was diluted with 30 ml of water, was extracted with dichloromethane and the organic phase was washed with saturated NaCl solution. Purification by chromatography on silica gel (dichloromethane) of the crude product obtained after drying with MgSO4 yielded 2.3 g of the triflate as a light colored oil; ESI-MS [M+H+]=295.5.

165.2 1-(8-fluorochinoline-4-yl)ethanone 1.3 g (4.4 mmol) 8-fluorochinoline-4-yl trifluoromethane sulfonate, 153 mg tetrakistriphenylphosphine palladium and 600 mg LiCl were suspended in a baked flask under protective gas in 30 ml dioxane, 1.6 g (4.43 mmol) (1-ethoxyvinyl)-tributylstannane was added, the mixture was heated for 2 hours at reflux. The mixture was diluted with dichloromethane, was washed with water, was dried (MgSO₄) and was concentrated. The residue thus obtained was dissolved in 30 ml THF and, following addition 2 ml 5N HCL, was stirred for 3 hours at room temperature. For workup, the mixture was adjusted with saturated NaHCO₃ solution to pH 11, was extracted with dichloromethane, the combined organic phases were washed with saturated NaCl solution and were dried with MgSO₄. Purification by chromatography on silica gel (dichloromethane) yielded 700 mg; ESI-MS [M+H+]=190.05.

165.3 2-bromo-1-(8-fluorochinoline-4-yl)ethanone

A total of 0.13 ml Br₂ were added portion-wise to 480 mg (2.54 mmol) 1-(8-fluorochinoline-4-yl)ethanone in 2 ml 48% HBr in water at 90° C. and were stirred for 30 minutes at 90° C. Following completion of the reaction, the water was diluted, was neutralized by addition of solid NaHCO₃ and was extracted with dichloromethane. Washing of the combined organic phases with saturated NaCl solution, drying and evaporation concentration yielded 600 mg of the desired bromide, which was directly reacted further.

165.4 N-(2,6-dimethoxybenzyl)-N'-[4-(8-fluorochinoline-4-yl)-1,3-thiazole-2-yl]guanidine Reaction of 150 mg (0.56 mmol) 2-bromo-1-(8-fluorochinoline-4-yl)ethanone analogously to Example 3 yielded 110 mg of the target product as a white-yellow solid; ESI-MS [M+H+]=438.05.

Example 166

1-[2-({imino[(2-methoxybenzyl)amino]methyl}amino)-1,3-thiazole-4(5H)-ylidene]piperidinium chloride Reaction of 100 mg (0.38 mmol) N-(2-chloro-1-piperidine-1-ylethylidene)-4-methylphenyl sulfonamide (preparation according to: Abdelaal, S.; Bauer, L. J. Het. Chem. 1988, 25 (6), 1849-1856) with 120 mg (0.38 mmol) N-[[(2-methoxybenzyl)amino](imino)-methyl]thiourea analogously to Example 3 yielded 12 mg of the desired product; ESI-MS [M+H+]=346.15. According to NMR, the compound exists as tautomeric mixture of 1-[2-({imino[(2-methoxybenzyl)amino]methyl}amino)-1,3-thiazole-4(5H)-ylidene]piperidine and N-(2-methoxybenzyl)-N'-(4-piperidine-1-yl-1,3-thiazole-2-yl)guanidine.
¹³C-NMR (100.61 MHz, DMSO-d6), δ (ppm): 23.61, 25.75, 36.23, 40.91, 49.94, 109.95, 120.28, 125.50, 128.30, 128.80, 157.09, 176.7667, 185.96.

Example 167

4-[2-{[[(2,6-dimethoxybenzyl)amino](imino)methyl]amino}-1,3-thiazole-4(5H)-yliden]morpholine-4-ium chloride

167.1 N-(2-chloro-1-morpholine-4-ylethylidene)-4-methylphenyl sulfonamide

To 1 g (5.02 mmol) 2-chloro-1-morpholine-4-ylethaniminium chloride and 0.7 ml triethylamine in 25 ml acetonitrile were added 0.96 g p-toluene sulfonic acid chloride at 10° C. and the mixture was stirred for 2 hours at 5-10° C. For workup, the mixture was diluted with dichlormethane, was washed with water and saturated NaCl-solution, was dried with MgSO$_4$, was filtered and was evaporation-concentrated. Chromatography on silica gel (dichlormethane/methanol 0-3%) yielded 400 mg of the target products; ESI-MS [M+H+]=317.05.

167.2 4-[2-{[[(2,6-dimethoxybenzyl)amino](imino)methyl]amino}-1,3-thiazole-4(5H)-yliden]morpholine-4-ium chloride The mixture of 200 mg (0.75 mmol) N-[[(2,6-dimethoxybenzyl)amino](imino)-methyl]thiourea and 240 mg (0.75 mmol) N-(2-chloro-1-morpholine-4-ylethylidene)-4-methylphenyl sulfonamide in 20 ml 2-butanone were heated for 24 hours at reflux. Normal workup yielded 170 mg of a light-colored solid; ESI-MS [M+H+]=378.25. According to NMR, the compound exists as a tautomeric mixture of 4-[2-{[[(2,6-dimethoxybenzyl)amino](imino)methyl]amino}-1,3-thiazole-4(5H)-yliden]morpholine and N-(2,6-dimethoxybenzyl)-N'-(4-morpholine-4-yl-1,3-thiazole-2-yl)guanidine.

$^{13}$C-NMR (100.61 MHz, DMSO-d6), δ (ppm): 34.76, 36.36, 47.81, 55.95, 65.15, 104.1, 110.66, 130.19, 158.11, 160.00, 177.51, 180.89.

Example 168

N-(2-methoxybenzyl)-N'-(6-methyl-1,3-benzothiazole-2-yl)guanidine fumarate 102 mg (0.62 mmol) 6-methyl-1,3-benzothiazole-2-amine and 200 mg (1.24 mmol) 1,1-di-1H-imidazole-1-ylmethaneimine (Wu, Y.-Q.; Hamilton, S. K.; Wilkinson, D. E.; Hamilton, G. S. *J. Org. Chem.* 2002, 67, 7553) were provided in THF (1 ml) and were heated while stirring in a microwave at 300 W radiation for 40 minutes to 130° C. Following addition of 2-methoxybenzylamine (85 mg, 0.62 mmol) the reaction mixture was heated to 130° C. for 60 minutes (300 W, heating by cooling). The THF was distilled off under vacuum on a rotary evaporator, the residue was chromatographically purified (silica gel, dichlormethane, methanol). The solid thus obtained was washed with dichlormethane and tert-butylmethylether; 20 mg, ESI-MS [M+H$^+$]=327.1

The following were prepared analogously to Example 168:

Example 169

N-(2,6-dimethoxybenzyl)-N'-(6-methyl-1,3-benzothiazole-2-yl)guanidine fumarate

ESI-MS [M+H+]=357.1.

Example 170

N-(6-ethoxy-1,3-benzothiazole-2-yl)-N'-(2-methoxybenzyl)guanidine fumarate

ESI-MS [M+H+]=357.1.

Example 171

N-(5-chlor-6-methyl-1,3-benzothiazole-2-yl)-N'-(2,6-dimethoxybenzyl)guanidine difumarate

ESI-MS [M+H+]=391.0.

Example 172

N-(2,6-dimethoxybenzyl)-N'-(5,6-dimethyl-1,3-benzothiazole-2-yl)guanidine fumarate

ESI-MS [M+H+]=371.1.

The compounds 181 and 185 were prepared by reaction of suitable starting materials of the formulae II and IV analogously to Example 2:

Example 181

N-(2,6-dimethoxybenzyl)-N'-(5-methyl-4H-1,2,4-triazole-3-yl)guanidine

The preparation of N-(2,6-dimethoxybenzyl)-N'-(5-methyl-4H-1,2,4-triazole-3-yl)guanidine was performed analogously to Example 2, with the following variations:

The saponification of N-{[(5-methyl-4H-1,2,4-triazole-3-yl)amino]carbonothioyl}-benzamide in methanolic sodium hydroxide solution, could be performed even at room temperature. The N-(5-methyl-4H-1,2,4-triazole-3-yl)thiourea formed was alkylated with methyl iodide at room temperature and the resulting methyl N-(5-methyl-4H-1,2,4-triazole-3-yl)imidothiocarbamate was liberated by extraction of the organic phase with 1 N NaOH. Finally, the methyl N-(5-methyl-4H-1,2,4-triazole-3-yl)imidothiocarbamate was brought to reaction with 2,6-dimethoxybenzylamine in ethanol at 130° C. in the microwave (100 Watt) and the N-(2,6-dimethoxybenzyl)-N'-(5-methyl-4H-1,2,4-triazole-3-yl) guanidine was isolated following chromatographic purification on preparative HPLC (Merck: Chromolith RP-18E, 100-25; eluent water/acetonitrile/0.1 molar acetic acid).

ESI-MS [M+H$^+$]=291.15

Example 185

N-(2-methoxybenzyl)-N'-(5-methyl-4H-1,2,4-triazole-3-yl)guanidine acetate

The preparation was performed analogously to Example 183. Here the intermediately formed N-[imino(methylthio)methyl]-5-methyl-4H-1,2,4-triazole-3-aminium iodide was reacted directly with 2-methoxybenzylamine in ethanol and a 1.5-fold excess of diisopropylethylamine to yield the target product.

ESI-MS [M+H$^+$]=261.15

The compound 192 was prepared analogously to Example 107 by reacting suitable starting materials of the formulae IV and V:

Example 192

Ethyl 2-{[[(2,6-dimethoxybenzyl)amino](imino)methyl]amino}-1,3-thiazole-4-carboxylate acetate The purification of the product proceeded by preparative HPLC (Merck: Chromolith RP-18E, 100-25; eluent water/acetonitrile/0.1 molar acetic acid).
ESI-MS [M+H$^+$]=365.05

The compounds 193, 195 and 196 according to the invention, were prepared according to the general method, for example described in *Organikum*, VEB Deutscher Verlag der Wissenschaften, Leipzig, Berlin, Heidelberg, 21. Edition, 2001, 483 or *Synth. Commun.* 1982, 12, 989-993 by aminolysis of 192:

Example 196

2-{[[(2,6-dimethoxybenzyl)amino](imino)methyl]amino}-N'-isopropyl-1,3-thiazole-4-carboxamide 0.157 g (0.35 mmol) ethyl 2-{[[(2,6-dimethoxybenzyl)amino](imino)methyl]amino}-1,3-thiazole-4-carboxylate bromide were combined with 1.50 ml (17.28 mmol) diisopropylamine and were heated in the microwave at 50 to 70° C. (150 Watt) for 2 hours. In this example, complete reaction was achieved only after further heating in the microwave at 70° C. (150 Watt) by "heating by cooling" after 4.5 hours. The reaction mixture was diluted with 20 ml dichlormethane and was washed with water (3×30 ml). After drying over MgSO$_4$, filtration and removal of the organic solvent under vacuum, the mixture was purified on preparative HPLC (Merck: Chromolith RP-18E, 100-25; eluent water/acetonitrile/0.1 molar acetic acid). 26 mg of 2-{[[(2,6-dimethoxybenzyl)amino](imino)methyl]amino}-N'-isopropyl-1,3-thiazole-4-carboxamide were isolated.
ESI-MS [M+H$^+$]=378.15
The following were prepared analogously to Example 196:

Example 193

N-allyl-2-{[[(2,6-dimethoxybenzyl)amino](imino)methyl]amino}-1,3-thiazole-4-carboxamide

ESI-MS [M+H$^+$]=376.15

Example 194

N-benzyl-2-{[[(2,6-dimethoxybenzyl)amino](imino)methyl]amino}-1,3-thiazole-4-carboxamide

ESI-MS [M+H$^+$]=426.15

The compound 175 was prepared by reaction of suitable starting materials of the formulae II and IV as follows:

Example 175

N-(2-methoxybenzyl)-N'-(5-phenyl-1,3,4-thiadiazol-2-yl)guanidine acetate 175.1. N-(5-phenyl-1,3,4-thiadiazol-2-yl)-1H-imidazole-1-carbothioamide 1.80 g (6.56 mmol) 5-phenyl-[1,3,4]thiadiazole-2-yl-ammonium sulfate were provided in 10 ml DMF, 4.99 ml (29.7 mmol) diisopropylethylamine were added and the mixture was stirred at room temperature until the suspension dissolved. Subsequently, 1.3 g (7.29 mmol) N,N'-thiocarbonyldiimidazole was added drop-wise in 10 ml acetonitrile and was stirred for 12 hours at room temperature. The solution was removed under vacuum, water was added to the residue and the solid formed was separated by filtration. After drying of the solid, 2.10 g N-(5-phenyl-1,3,4-thiadiazole-2-yl)-1H-imidazole-1-carbothioamide was isolated as a crude mixture, which was used without further separation.
$^1$H-NMR ([400 MHz, DMSO-d6): δ (ppm) 7.33 (pt, 1H), 7.33-7.54 (m, 3H), 7.66 (m, 1H, J=1.1 Hz), 7.96 (dd, 2H, J=8.1 Hz, J=1.4 Hz), 8.16 (pt, 1H, J=1.3 Hz), 9.18 (s, 1H).

175.2 N-(5-phenyl-1,3,4-thiadiazole-2-yl)-thiourea 1.0 g of the crude mixture with N-(5-phenyl-1,3,4-thiadiazole-2-yl)-1H-imidazole-1-carbothioamide was combined with 0.536 g (6.96 mmol) ammonium acetate in 4 ml ethanol. The reaction mixture was heated in the microwave (at 100 Watt) for 30 minutes at 90° C. After completion of the reaction, the solvent was distilled off under vacuum, and water was added to the residue formed. After extraction with CH$_2$Cl$_2$ and drying of the organic phase with magnesium sulfate, the product crystallized out of the organic solvent and, after filtration, was washed with diethylether. 0.52 g of the N-(5-phenyl-1,3,4-thiadiazole-2-yl)-thiourea was obtained.
ESI-MS [M+H$^+$]=237.05

175.3 Methyl N-(5-phenyl-1,3,4-thiadiazole-2-yl)imidothiocarbamate 0.52 g (2.22 mmol) N-(5-phenyl-1,3,4-thiadiazole-2-yl)-thiourea were dissolved in 4 ml of methanol and 0.515 g (3.63 mmol) methyl iodide were added. The reaction mixture was stirred at 50° C. for 2 hours and for a further 12 hours at room temperature. For the liberation of the intermediately formed iodide salt, 0.427 g (3.30 mmol) diisopropylethylamine were added to the mixture and were stirred for 2 hours at room temperature. The solvent was removed under vacuum and the residue was dissolved in dichloromethane. The liberation of the iodide salt can also alternatively proceed by extraction with 2 N sodium hydroxide solution. After extraction with water, (3×50 ml) the organic phase was dried over MgSO$_4$ and, following a removal of the solvent under vacuum, the 0.37 g of crude product were isolated, which were used in the following reaction without further purification.
ESI-MS [M+H$^+$]=251.10

175.4 N-(2-methoxybenzyl)-N'-(5-phenyl-1,3,4-thiadiazol-2-yl)guanidine acetate 0.185 g (0.74 mmol) methyl N-(5-phenyl-1,3,4-thiadiazole-2-yl)imidothiocarbamate were dissolved together with 0.132 g (0.96 mmol) 2-methoxybenzylamine in 3 ml ethanol and were heated in the microwave (at 100 Watt) for 30 minutes at 90° C. In the cases in which the reaction did not go to completion, 2 ml of toluene were added and the mixture was again heated in the microwave (at 100 Watt) for 30 minutes at 100° C. After complete reaction, the solvent was removed under vacuum. The residue was separated by preparative HPLC (Merck: Chromolith RP-18E, 100-25; eluent water/acetonitrile/0.1 molar acetic acid) and 32 mg of the pure N-(2-methoxybenzyl)-N'-(5-phenyl-1,3,4-thiadiazol-2-yl)guanidine acetate were isolated.
ESI-MS [M+H$^+$]=340.15

The compounds 176-178, and 183 were prepared by reaction of suitable starting materials of the formulae II and IV analogously to Example 175:

Example 176

N-(2,6-dimethoxybenzyl)-N'-(5-phenyl-1,3,4-thiadiazole-2-yl)guanidine

ESI-MS [M+H$^+$]=370.15

Example 177

N-(2,6-dimethoxybenzyl)-N'-1H-imidazole-2-ylguanidine acetate

ESI-MS [M+H$^+$]=276.15

Example 178

N-(2-methoxybenzyl)-N'-(5-methyl-1,3,4-thiadiazole-2-yl)guanidine

ESI-MS [M+H$^+$]=278.05

Example 183

N-1H-imidazole-2-yl-N'-(2-methoxybenzyl)guanidine acetate
ESI-MS [M+H$^+$]=246.05

The compounds 179 and 180 were prepared by reaction of suitable starting materials of the formulae II and IV analogously to Example 175, wherein the corresponding commercially available thiourea derivatives were treated with 1 N sodium hydroxide solution, as in 175.3, after the reaction with methyl iodide, to liberate the iodide salt. The addition of toluene, as in 175.4, was not necessary here:

Example 179

N-1H-indazole-3-yl-N'-(2-methoxybenzyl)guanidine acetate

ESI-MS [M+H$^+$]=296.15

Example 180

N-(2,6-dimethoxybenzyl)-N'-1H-indazole-3-ylguanidine acetate

ESI-MS [M+H$^+$]=326.15

Example 182

N-1H-benzimidazole-2-yl-N'-(2,6-dimethoxybenzyl)guanidine diacetate

182.1 N-1H-benzimidazole-2-ylthiourea 0.535 g (3.0 mmol) N,N'-thiocarbonyldiimidazole was dissolved in 5 ml acetonitrile, and to this yellow solution was added drop-wise 0.40 g (3.0 mmol) 2-aminobenzimidazole, suspended in 5 ml acetonitrile, at room temperature. After 30 minutes, a precipitate formed, and the mixture was stirred another 12 hours. After 0.474 g (6.0 mmol) ammonium acetate in substance (German: "in Substanz") was added to this mixture, the mixture was heated in the microwave (at 100 Watt) 30 minutes long at 90° C. The solvent was removed under vacuum, water was added to the residue and an extraction with dichloromethane (3×30 ml) followed. The combined organic phase was washed once again with water and, after drying over MgSO$_4$, the solvent was removed under vacuum. The product was purified by means of preparative HPLC (Merck: Chromolith RP-18E, 100-25; eluent wasser/acetonitrile/0.1 molar acetic acid). In this single pot procedure, 0.27 g of the N-1H-benzimidazole-2-ylthiourea was directly recovered without isolation of the intermediate.

ESI-MS [M+H$^+$]=193.05

182.2 (1H-benzimidazole-2-ylamino)(methylthio)methaneiminium iodide

To 0.27 g (1.40 mmol) N-1H-benzimidazole-2-ylthiourea were added 0.115 ml (1.83 mmol) methyl iodide dissolved in 4 ml of methanol. It was heated for 30 minutes at reflux. After completion of the reaction, the solvent was removed under vacuum and 0.47 g 1H-benzimidazole-2-ylamino)(methylthio)methane iminium iodide was used without further purification for the following reaction.

ESI-MS [M+H$^+$]=207.05

182.3 N-1H-benzimidazole-2-yl-N'-(2,6-dimethoxybenzyl)guanidine diacetate 0.470 g (1.4 mmol) 1H-benzimidazole-2-ylamino)(methylthio)methane iminium iodide were dissolved in 4 ml ethanol and, after addition of 0.24 ml (1.41 mmol) diisopropylethylamine and 0.282 g (1.69 mmol) 2,6-dimethoxybenzylamine, was heated together for 3 hours under reflux. Alternatively, the reaction can take place correspondingly in a microwave (at 100-200 Watt) for 30 minutes at 90-100° C. After complete reaction, the solvent was removed under vacuum. The residue was dissolved in water and the product in the organic phase was extracted with dichloromethane. The organic phase was washed 1 N NaOH (2×50 ml) to completely remove iodide from the product. After drying over MgSO$_4$ and filtration, the organic solvent was removed under vacuum. A voluminous precipitate formed after the residue was dissolved 4 ml acetonitrile/water (1:1) and 0.5 ml glacial acetic acid. The solid was filtered off and 30 mg of the desired product was obtained.

ESI-MS [M+H$^+$]=326.25

The compounds 184 and 189 were prepared by reaction of suitable starting materials of the formulae II and IV analogously to Example 182:

Example 184

N-(2-methoxybenzyl)-N'-4H-1,2,4-triazole-3-ylguanidine acetate

ESI-MS [M+H$^+$]=247.05

Example 189

N-(2,6-Dimethoxybenzyl)-N'-4H-1,2,4-triazole-3-ylguanidine acetate

ESI-MS [M+H$^+$]=277.10

Example 187

N-(2,6-dimethoxybenzyl)-N'-(4-phenyl-1H-imidazole-2-yl)guanidine acetate

187.1 N-(4-phenyl-1H-imidazole-2-yl)thiourea 2.10 g (11.78 mmol) N,N'-thiocarbonyldiimidazole and 2.44 g (5.64 mmol) bis(4-phenyl-1H-imidazole-2-aminium) sulphate were combined and 50 ml of acetonitrile were added. The reaction mixture was warmed to 50° C. for 6 hours. After complete reaction, 2.26 g (29.29 mmol) ammonium acetate were added and the mixture was heated for one hour to 80° C. The batch was freed of solvent under vacuum. Water was added to the residue and this was extracted (3×150 ml) with dichloromethane. The combined organic phase was dried over MgSO$_4$, was filtered and was evaporation-concentrated; 1.78 g ESI-MS [M+H$^+$]=219.05

187.2 Methyl IV-(4-phenyl-1H-imidazole-2-yl)imidothiocarbamate

The preparation proceeded analogously to 182.2. 1.89 g of product were isolated.
ESI-MS [M+H$^+$]=233.95

187.3 N-(2,6-dimethoxybenzyl)-N'-(4-phenyl-1H-imidazole-2-yl)guanidine acetate The preparation proceeded analogously to 182.3. Following purification, 180 mg of clean product were isolated.
ESI-MS [M+H$^+$]=352.15

The compounds 186 and 188 were prepared by reacting suitable starting materials of the formulae II and IV analogously to Example 187:

Example 186

N-[4-(4-fluorophenyl)-1H-imidazole-2-yl]-N'-(2-methoxybenzyl)guanidine

ESI-MS [M+H$^+$]=340.15

Example 188

N-(2-methoxybenzyl)-N'-(4-phenyl-1H-imidazole-2-yl)guanidine acetate

ESI-MS [M+H$^+$]=322.15

The compounds 191 and 195 were prepared by reaction of suitable starting materials of the formulae II and IV, as follows:

Example 191

N-(2,6-dimethoxybenzyl)-N'-[4-(4-fluorophenyl)-1H-imidazole-2-yl]guanidine acetate

191.1 N-[4-(4-fluorphenyl)-1H-imidazole-2-yl]acetamide 3.00 g (13.82 mmol) 2-bromo-4'-fluoroacetophenone, 2.80 g (27.64 mmol) acetylguanidine and 15 ml acetonitrile were combined and were together brought to reaction in the microwave (at 100 Watt) for 60 minutes at 40° C. by "heating by cooling". After cooling, the solid formed was filtered off of the solvent. In addition, a total amount of 1.02 g N-[4-(4-fluorphenyl)-1H-imidazole-2-yl]acetamide were isolated by fractional crystallization with ethanol of the remainder of the mother liquor.
ESI-MS [M+H$^+$]=220.05

191.2 4-(4-fluorphenyl)-1H-imidazole-2-aminium chloride 1.0 g (4.56 mmol) N-[4-(4-fluorphenyl)-1H-imidazole-2-yl]acetamide were suspended in 30 ml 2 N HCl and 30 ml ethanol and were stirred at 80° C. for 2 hours. After removal of the solvent under vacuum, 0.97 g 4-(4-fluorphenyl)-1H-imidazole-2-aminium chloride were obtained, which was used in the following reaction without further purification.
ESI-MS [M+H$^+$]=214.05

1919.3 N-[4-(4-fluorphenyl)-1H-imidazole-2-yl]thiourea

The preparation proceeded analogously to 187.1. After purification, 0.74 g of clean product were isolated.
ESI-MS [M+H$^+$]=237.05

191.4 Methyl N-[4-(4-fluorphenyl)-1H-imidazole-2-yl]imidothiocarbamate

The preparation proceeded analogously to 175.3, wherein the 4-(4-fluorphenyl)-N-[imino(methylthio)methyl]-1H-imidazole-2-aminium iodide obtained as an intermediate, was treated with 2 N sodium hydroxide solution. Following purification, 0.75 g of clean product was isolated.
ESI-MS [M+H$^+$]=251.05

191.5 N-(2,6-dimethoxybenzyl)-N'-[4-(4-fluorphenyl)-1H-imidazole-2-yl]guanidine acetate The preparation proceeded analogously to 175.4. The reaction of 0.40 g (1.60 mmol) methyl N-[4-(4-fluorphenyl)-1H-imidazole-2-yl]imidothiocarbamate with 0.53 g (3.20 mmol) 2,6-dimethoxybenzylamine in ethanolic solution was carried out in the microwave for 3 minutes at 150° C. (200 Watt). Following purification, 35 mg of clean product were isolated.
ESI-MS [M+H$^+$]=370.15

Example 195

N-(2-chlor-6-methoxybenzyl)-N'-[4-(4-fluorphenyl)-1H-imidazole-2-yl]guanidine acetate

ESI-MS [M+H$^+$]=374.10/376.10

Example 190

N-(2,6-dimethoxybenzyl)-N'-(4-methyl-1,3-oxazole-2-yl)guanidine acetate

190.1 N-cyano-N'-(2,6-dimethoxybenzyl)guanidine 15 ml 2N hydrochloric acid were added to 5.0 g (29.9 mmol) 2,6-dimethoxybenzylamine and the aqueous phase was subsequently removed under vacuum. The residue was then dissolved in 50 ml 1-butanol and 2.66 g (29.9 mmol) of sodium dicyanamide were added. The reaction mixture was heated for 5.5 hours at reflux and stirred for 12 hours at room temperature. The precipitate formed was filtered off, was washed with diethylether; 6.81 g.
ESI-MS [M+H$^+$]=235.15

190.2 N-(2,6-dimethoxybenzyl)-N'-(4-methyl-1,3-oxazole-2-yl)guanidine acetate 0.20 g (0.85 mmol) N-cyano-N'-(2,6-dimethoxybenzyl) guanidine were suspended in 20 ml methanol/water (1:1). Subsequently, 63.3 mg (0.85 mmol) hydroxyacetone were added and the mixture was heated to 40° C. The pH-value was adjusted at high temperature with 1 N HCl to 2.5-3 pH. In total, the reaction mixture was heated for 34 hours at 40° C. under constant pH-control until no further educts could be detected by mass spectrometry. The methanol was distilled off under vacuum and a white solid remained which was purified by HPLC (Merck: Chromolith RP-18E, 100-25; eluent water/acetonitrile/0.1 molar acetic acid); 64 mg.
ESI-MS [M+H$^+$]=291.15

The compounds 173, 174 and 197-199 were prepared by reaction of suitable starting materials of the formulae IV and VII analogously to Example 190:

Example 173

N-(4,5-dimethyl-1,3-oxazole-2-yl)-N'-(2-methoxybenzyl)guanidine

ESI-MS [M+H$^+$]=275.15

Example 174

N-(2,6-dimethoxybenzyl)-N'-(4,5-dimethyl-1,3-oxazole-2-yl)guanidine acetate

ESI-MS [M+H$^+$]=305.15

Example 197

N-(2-methoxybenzyl)-N'-(4-phenyl-1,3-oxazole-2-yl)guanidine

The cyclization of 0.60 g (2.94 mmol) N-cyano-N'-(2-methoxybenzyl)guanidine with 0.44 g (2.94 mmol) 2-hydroxyacetophenone was performed in 20 ml acetonitrile and water (1:1). The pH value of the mixture was adjusted with 1 N hydrochloric acid to pH 1.5 and the mixture was then heated in the microwave at 45° C. (100 Watt) for 4.5 hours. After workup and purification, analogously to 190.2, 0.10 g of pure product was obtained.
ESI-MS [M+H$^+$]=323.15

Example 198

N-[4-(4-fluorophenyl)-1,3-oxazole-2-yl]-N'-(2-methoxybenzyl)guanidine

The preparation of N-[4-(4-fluorophenyl)-1,3-oxazole-2-yl]-N'-(2-methoxybenzyl)guanidine proceeded analogously to Example 197.
ESI-MS [M+H$^+$]=341.05

Example 199

N-(2,6-dimethoxybenzyl)-N'-(4-phenyl-1,3-oxazole-2-yl)guanidine

The preparation of N-(2,6-dimethoxybenzyl)-N'-(4-phenyl-1,3-oxazole-2-yl)guanidines proceeded analogously to Example 197.
ESI-MS [M+H$^+$]=353.35

Example 200

N-(5-tert-butyl-1H-pyrazole-3-yl)-N'-(2-methoxybenzyl)-guanidine 200.1 (5-tert-butyl-1H-pyrazole-3-yl)-thiourea 1.5 g (11.3 mmol) 3-amino-5-tert-butylpyrazole dissolved in acetonitrile, was added drop-wise and slowly to a solution of 2.0 g (11.3 mmol) thiocarbonyldiimidazole in 25 ml acetonitrile, at 0° C. The batch was stirred for 20 minutes at 0° C., ammonium acetate (1.6 g, 21.5 mmol) was then added, and the mixture was heated in the microwave for 30 minutes at 90° C. (radiation power 200 Watt/without cooling). The solid formed was suction-isolated, the solution was concentrated and the oily residue (4.3 g) was crudely purified on silica gel (0.9 g yellowish solid)

200.2 1-(5-tert-butyl-1H-pyrazole-3-yl)-2-methyl-isothiourea hydroiodide 270 mg (1.4 mmol) (5-tert-butyl-1H-pyrazole-3-yl)-thiourea were dissolved in 2 ml methanol, methyl iodide (202 mg, 1.4 mmol) was added and the mixture was stirred overnight at room temperature. The reaction mixture was concentrated, dichloremethane was added to the residue and the mixture was stirred at room temperature. The solid was suction-isolated and dried (0.43 g).

200.3 N-(5-tert-butyl-1H-pyrazole-3-yl)-N'-(2-methoxy-benzyl)-guanidine 120 mg (0.35 mmol) 1-(5-tert-butyl-1H-pyrazole-3-yl)-2-methyl-isothiourea hydroiodide and 150 mg (1.1 mmol) 2-methoxybenzylamine were dissolved in 1 ml 1-propanol and were stirred in the microwave at 100° C. for 30 minutes (radiation power 200 Watt/without cooling).

The reaction solution was concentrated and the colorless oil (0.29 g) was purified by chromatography on silica gel (Chromabond RP18; water/acetonitrile+0.1% acetic acid 0-80%), wherein 83 mg of light yellow foam were obtained. Stirring with diethylether yielded 53 mg of white solid.
ESI-MS [M+H+]=303

The following were prepared analogously to Example 200

Example 201

N-(2-methoxybenzyl)-N'-(5-phenyl-1H-pyrazole-3-yl)guanidine

Starting from 100 mg 2-methyl-1-(5-phenyl-1H-pyrazole-3-yl)-isourea hydroiodide; 57 mg target product.
ESI-MS [M+H+]=322

Example 202

N-(2,6-dimethoxybenzyl)-N'-(5-phenyl-1H-pyrazole-3-yl)guanidine

Starting from 100 mg 2-methyl-1-(5-phenyl-1H-pyrazole-3-yl)-isourea hydroiodide; 49 mg target product.
ESI-MS [M+H+]=352

Example 203

N-(2,6-dimethoxybenzyl)-N'-1H-pyrazole-3-ylguanidine

Starting from 100 mg 2-methyl-1-(1H-pyrazole-3-yl)-isourea hydroiodide, 46 mg target product.
ESI-MS [M+H+]=276

Example 204

N-(5-tert-butyl-1H-pyrazole-3-yl)-N'-(2,6-dimethoxybenzyl)guanidine

Starting from 120 mg 1-(5-tert-butyl-1H-pyrazole-3-yl)-2-methyl-isothiourea hydroiodide, 82 mg target product.
ESI-MS [M+H+]=332

Example 205

N-(2-methoxybenzyl)-N'-1H-pyrazole-3-ylguanidine

Starting from 130 mg 2-methyl-H1H-pyrazole-3-yl)-isourea hydroiodide; 67 mg target product.
ESI-MS [M+H+]=246

Example 206

N-(2-methoxybenzyl)-N'-[5-(4-methylphenyl)-1H-pyrazole-3-yl]guanidine

Starting from 150 mg 2-methyl-1-(5-p-tolyl-1H-pyrazole-3-yl)-isourea hydroiodide; 79 mg target product.
ESI-MS [M+H+]=336

Example 207

N-(2,6-dimethoxybenzyl)-N'-[5-(4-methylphenyl)-1H-pyrazole-3-yl]guanidine

Starting from 150 mg 2-methyl-1-(5-p-tolyl-1H-pyrazole-3-yl)-isourea hydroiodide; 103 mg target product.
ESI-MS [M+H+]=366

Example 208

N-(2-methoxybenzyl)-N'-[5-(4-methoxyphenyl)-1H-pyrazole-3-yl]guanidine

Starting from 120 mg 1-[5-(4-methoxy-phenyl)-1H-pyrazole-3-yl]-2-methyl-isourea hydroiodide; 56 mg target product.
ESI-MS [M+H+]=352

Example 209

N-(2,6-dimethoxybenzyl)-N'-[5-(4-methoxyphenyl)-1H-pyrazole-3-yl]guanidine

Starting from 120 mg 1-[5-(4-Methoxy-phenyl)-1H-pyrazole-3-yl]-2-methyl-isourea hydroiodide; 54 mg target product.
ESI-MS [M+H+]=382

Example 210

N-(5-tert-butyl-1H-pyrazole-3-yl)-N'-(2-fluoro-6-methoxybenzyl)guanidine

Starting from 170 mg 1-(5-tert-Butyl-1H-pyrazole-3-yl)-2-methyl-isourea hydroiodide; 93 mg target product.
ESI-MS [M+H+]=320

Example 211

N-[5-(4-chlorophenyl)-1H-pyrazole-3-yl]-N'-(2-methoxybenzyl)guanidine

Starting from 150 mg 1-[5-(4-Chloro-phenyl)-1H-pyrazole-3-yl]-2-methyl-isourea hydroiodide; 30 mg target product.
ESI-MS [M+H+]=356/358

Example 212

N-[5-(4-chlorophenyl)-1H-pyrazole-3-yl]-N'-(2,6-dimethoxybenzyl)guanidine

Starting from 140 mg 1-[5-(4-Chloro-phenyl)-1H-pyrazole-3-yl]-2-methyl-isourea hydroiodide; 71 mg target product.
ESI-MS [M+H+]=386/388

Example 213

N-(5-tert-butyl-1H-pyrazole-3-yl)-N'-(2-chloro-6-methoxybenzyl)guanidine

Starting from 150 mg 1-(5-tert-butyl-1H-pyrazole-3-yl)-2-methyl-isourea hydroiodide; 89 mg target product.
ESI-MS [M+H+]=336/338

Example 214

N-(2-methoxybenzyl)-N'-(1-methyl-1H-pyrazole-3-yl)guanidine

Starting from 160 mg 2-methyl-1-(1-methyl-1H-pyrazole-3-yl)-isourea hydroiodide; 34 mg target product.
ESI-MS [M+H+]=260

Example 215

N-(2,6-dimethoxybenzyl)-N'-(1-methyl-1H-pyrazole-3-yl)guanidine

Starting from 160 mg 2-methyl-1-(1-methyl-1H-pyrazole-3-yl)-isourea hydroiodide, 56 mg target product.
ESI-MS [M+H+]=290

Example 216

N-(5-tert-butyl-1H-pyrazole-3-yl)-N'-(2-methoxy-6-methylbenzyl)guanidine

Starting from 130 mg 1-(5-tert-butyl-1H-pyrazole-3-yl)-2-methyl-isourea hydroiodide; 47 mg target product.
ESI-MS [M+H+]=316

Example 217

N-(2-methoxybenzyl)-N'-(4-phenyl-1H-pyrazole-3-yl)guanidine

Starting from 150 mg 2-methyl-1-(4-phenyl-1H-pyrazole-3-yl)-isourea hydroiodide; 76 mg target product.
ESI-MS [M+H+]=322

Example 218

N-(2,6-dimethoxybenzyl)-N'-(4-phenyl-1H-pyrazole-3-yl)guanidine

Starting from 160 mg 2-methyl-1-(4-phenyl-1H-pyrazole-3-yl)-isourea hydroiodide; 83 mg target product.
ESI-MS [M+H+]=352

Example 219

N-(2,6-dimethoxybenzyl)-N'-(1-phenyl-1H-pyrazole-3-yl)guanidine

Starting from 160 mg 2-methyl-1-(1-phenyl-1H-pyrazole-3-yl)-isourea hydroiodide; 34 mg target product.
ESI-MS [M+H+]=352

Example 220

N-(2-methoxybenzyl)-N'-(1-phenyl-1H-pyrazole-3-yl)guanidine

Starting from 130 mg 2-methyl-1-(1-phenyl-1H-pyrazole-3-yl)-isourea hydroiodide; 47 mg target product.
ESI-MS [M+H+]=322

Example 221

N-[2-methoxy-5-(trifluoromethyl)benzyl]-N'-(4-phenyl-1,3-thiazole-2-yl)guanidine 221.1 The preparation of 2-methoxy-5-trifluoromethyl-benzylamine proceeded starting from 2-methoxy-5-trifluoromethyl-benzonitrile by reduction with lithium aluminium hydride in tetrahydrofuran under standard conditions.

221.2 Starting from 100 mg 2-methyl-1-(4-phenyl-thiazole-2-yl)-isourea hydroiodide; 41 mg target product.
ESI-MS [M+H+]=407

Example 222

N-4H-chromeno[4,3-d][1,3]thiazole-2-yl-N'-(2,6-dimethoxybenzyl)guanidine

Reaction analogously to Example 107 starting from 210 mg 3-bromo-2,3-dihydro-4H-chromen-4-one (0.92 mmol) yielded 80 mg of the desired product as a white solid;
ESI-MS [M+H+]=399.1.

Example 223

N-(2,6-dimethoxybenzyl)-N'-(4,5,6,7-tetrahydro[1,3]thiazolo[5,4-c]pyridine-2-yl)guanidine 223.1-3-bromo-4-oxopiperidine-1-carboxylate To 1 g N-benzyl-4-oxopiperidine-1-carboxylate (4.3 mmol) in 20 ml THF were added 0.5 ml glacial acetic acid and 0.22 ml bromine at 10° C., and the mixture was stirred at room temperature for 1 hour. For workup, 20 ml of water were added, the mixture was neutralized with NaHCO₃ and was subsequently extracted multiple times with dichloromethane. The combined organic phases were then washed with saturated NaCl-solution, were dried and were concentrated. In this way, 1.2 g of the desired bromide were obtained as a yellowish oil which was used without further purification.

223.2 Benzyl-2-{[[(2,6-dimethoxybenzyl)amino](imino)methyl]amino}-6,7-dihydro[1,3]thiazolo[5,4-c]pyridine-5(4H)-carboxylate Reaction of 180 mg benzyl-3-bromo-4-oxopiperidine-1-carboxylate analogously to Example 107 yielded 40 mg of the desired product; ESI-MS [M+H+]=482.1.

223.3 N-(2,6-dimethoxybenzyl)-N'-(4,5,6,7-tetrahydro[1,3]thiazolo[5,4-c]pyridine-2-yl)guanidine 0.2 ml HBr (33% in glacial acetic acid) were added to 150 mg benzyl-2-{[[(2,6-dimethoxybenzyl)amino](imino)methyl]amino}-6,7-dihydro[1,3]thiazolo[5,4-c]pyridine-5(4H)-carboxylat (0.28 mmol) in 2 ml glacial acetic acid, and the mixture was stirred for 2 hours at room temperature. After reaction completion, the mixture was evaporation-concentrated, was filtered over C18 Chromabond (water/CH₃CN+ 0.1% glacial acetic acid; 0-30%), and the free base was obtained by stirring with polymer-bound carbonate in methanol. 60 mg; ESI-MS [M+H+]=348.15.

Example 224

N-(5-acetyl-4,5,6,7-tetrahydro[1,3]thiazolo[5,4-c]pyridine-2-yl)-N'-(2,6-dimethoxybenzyl)guanidine Acetylation of 110 mg N-(2,6-dimethoxybenzyl)-N'-(4,5,6,7-tetrahydro[1,3]thiazolo[5,4-c]pyridine-2-yl)guanidine (0.26 mmol, Example 221.3) under standard conditions with acetylchloride and triethylamine in 15 ml THF followed by purification, yielded 16 mg of the desired product as a white solid; ESI-MS [M+H+]=390.15.

Example 225

N-(2,6-dimethoxybenzyl)-N'-[5-(phenylsulfonyl)-4,5,6,7-tetrahydro[1,3]thiazolo[5,4-c]pyridine-2-yl]guanidine Reaction of 30 mg N-(2,6-dimethoxybenzyl)-N'-(4,5,6,7-tetrahydro[1,3]thiazolo[5,4-c]pyridine-2-yl)guanidine (0.09 mmol, Example 221.3) with 18 mg phenylsulfonic acid chloride and 40 mg polymer-bound DMAP (Argonaut; 1.06 mmol/g) in 5 ml dichloromethane followed by chromatographic purification (dichloromethane/methanol 2-4%) yielded 15 mg of the target product; ESI-MS [M+H+]=488.15.

Example 226

N-(5-benzyl-4,5,6,7-tetrahydro[1,3]thiazolo[5,4-c]pyridine-2-yl)-N'-(2,6-dimethoxybenzyl)guanidine 226.1 1-benzyl-3-bromopiperidine-4-one hydrobromide
Bromination of 3 g N-benzyl-4-oxopiperidine (15.85 mmol) analogously to Example 221.1 yielded 5.2 g of the bromide as a light-yellow solid.

226.2 Liberation of the base from hydrobromide and reaction with 200 mg 1-benzyl-3-bromopiperidine-4-one (0.75 mmol) analogously to Example 107 yielded 93 mg of the desired product; ESI-MS [M+H+]=438.3.

Biological Tests

1. [$^3$H]5-CT Binding Assay h5-HT$_{5A}$

Membranes from HEK293-cells, which permanently express the h5-HT$_{5A}$ receptor gene, were incubated in 100 mM Tris-HCl-buffer (pH 7.7), containing 1 mM EDTA in the presence of 2.5 nM [$^3$H]5-CT (600 µl total volume). The total binding is defined as the binding which is observed when the membranes are incubated alone in the presence of the radioligand. The inhibition induced by the compound is determined by incubation of cell membranes in the presence of the radioligand, and of different concentrations of the compound of interest. Unspecific binding is defined by the binding of [$^3$H]5-CT, which is obtained by incubation of the membranes as for the total binding but in the presence of 10 µM methiothepine. Following an incubation of 75 minutes at 30° C. the membrane suspension is filtered through GF/B-filters, wrapped in 0.03% PEI, wherein a Skatron® harvest system is used. The radioactivity retained in the filter is quantified by liquid scintillation counting.

2. Funktional Assay for Human 5-HT5A Receptor Ligands-Serotonin-Induced Increase of GTP-Europium Binding General Description:

Stimulation of G protein-coupled receptors by suitable agonists leads to the binding of GTP to the α-subunit of trimeric G-proteins, followed by the dissociation of the GTP-bound α-subunit from the βγ-subunit and the activation of signal transduction. By using a Europium-labelled GTP-analog, GTP-Eu, the activation of a G-protein-coupled receptor by an agonist can be monitored as an increase in the binding of GTP-Eu to the receptor-G-protein-complex. After removal of unbound GTP-Eu, bound GTP-Eu can be quantified by measuring the time-resolved fluorescence emission in suitable detection apparati.

Cell line: h5HT5A__18.2_SH-sy-5y, a human neuroblastoma cell line, which stably expresses the human 5-HT5A receptor.

Membrane preparation: Cell membranes are prepared according to a standard protocol in the presence of protease inhibitors and are partially purified by two sequential centrifugation steps at 40000×g. Aliquots are stored at −80° C.

Assay:

The assay is performed in filter plates with 96 wells (AcroWell-96, Pall Corp.). The receptor membranes diluted in assay buffer (2.5 µM GDP, 100 mM NaCl, 3 mM MgCl$_2$, 50 mM HEPES pH 7.4) are added to the filter plate (5 µg receptor membrane/well). Test compounds are dissolved in 100% DMSO and serial dilutions are added to the receptor membranes (DMSO final concentration 0.5%). The reaction is started by addition of serotonin (final concentration 1 µM, total assay volume 100 µl). After a first incubation period of 30 min at 30° C., GTP-Eu (final concentration 10 nM) is added, followed by a second incubation period of 30 min at 30° C. The reaction is stopped by rapid vacuum filtration and the wells are washed twice with ice-cold assay buffer. Bound GTP-Eu is measured in a VICTOR multilabel counter (PerkinElmer Corp.) using the time-resolved Europium settings. The data are corrected with respect to the unspecific binding and IC50 values are calculated with PRISM 4.0 (GraphPad Inc.) using standard non-linear curve-fitting algorithms. Kb values are calculated from IC50 values using the Cheng-Prusoff approximation.

In both assays, different concentrations of the test substances are used, and the Ki or the IC50 values are determined. The affinity of selected compounds is shown in the following table:

TABLE 1

Affinity to 5-HT5A (Ki)

| Example # | Binding affinity 5-HT5A (Ki) |
|---|---|
| 1 | +++ |
| 2 | +++ |
| 3 | +++ |
| 4 | ++ |
| 5 | +++ |
| 6 | +++ |
| 7 | + |
| 8 | +++ |
| 9 | +++ |
| 11 | ++ |
| 12 | + |
| 13 | + |
| 14 | ++ |
| 15 | + |
| 16 | + |
| 17 | ++ |
| 18 | + |
| 19 | ++ |
| 20 | + |
| 21 | +++ |
| 22 | + |
| 23 | + |
| 24 | + |
| 26 | + |
| 27 | +++ |
| 28 | ++ |
| 29 | ++ |
| 30 | ++ |
| 31 | ++ |
| 32 | +++ |
| 33 | +++ |
| 34 | +++ |
| 35 | + |
| 36 | +++ |
| 37 | ++ |
| 38 | ++ |
| 39 | +++ |
| 40 | +++ |
| 41 | +++ |
| 42 | +++ |
| 43 | ++ |
| 44 | +++ |
| 45 | +++ |
| 46 | +++ |
| 47 | +++ |
| 48 | ++ |
| 49 | +++ |
| 50 | +++ |
| 51 | +++ |
| 52 | + |
| 53 | ++ |
| 54 | +++ |
| 55 | +++ |
| 56 | +++ |
| 57 | +++ |
| 58 | +++ |
| 59 | +++ |
| 60 | +++ |
| 61 | +++ |
| 62 | ++ |
| 63 | +++ |
| 64 | +++ |
| 65 | +++ |
| 66 | +++ |
| 67 | +++ |
| 68 | +++ |
| 69 | +++ |
| 70 | +++ |
| 71 | +++ |

TABLE 1-continued

Affinity to 5-HT5A (Ki)

| Example # | Binding affinity 5-HT5A (Ki) |
|---|---|
| 72 | +++ |
| 73 | +++ |
| 74 | +++ |
| 75 | +++ |
| 76 | +++ |
| 77 | +++ |
| 78 | +++ |
| 79 | +++ |
| 80 | +++ |
| 81 | +++ |
| 82 | ++ |
| 83 | +++ |
| 84 | +++ |
| 85 | +++ |
| 86 | +++ |
| 87 | +++ |
| 88 | +++ |
| 89 | +++ |
| 90 | +++ |
| 91 | +++ |
| 92 | ++ |
| 93 | +++ |
| 94 | +++ |
| 95 | ++ |
| 96 | +++ |
| 97 | +++ |
| 98 | ++ |
| 99 | ++ |
| 100 | +++ |
| 101 | ++ |
| 102 | +++ |
| 103 | ++ |
| 104 | + |
| 105 | + |
| 106 | + |
| 107 | ++ |
| 108 | + |
| 109 | ++ |
| 110 | +++ |
| 111 | +++ |
| 112 | +++ |
| 113 | +++ |
| 114 | +++ |
| 115 | +++ |
| 116 | +++ |
| 117 | +++ |
| 118 | +++ |
| 119 | +++ |
| 120 | ++ |
| 121 | +++ |
| 122 | +++ |
| 123 | +++ |
| 124 | +++ |
| 125 | +++ |
| 126 | +++ |
| 127 | +++ |
| 128 | +++ |
| 129 | ++ |
| 130 | ++ |
| 131 | +++ |
| 132 | +++ |
| 133 | +++ |
| 134 | ++ |
| 135 | +++ |
| 136 | ++ |
| 137 | + |
| 138 | +++ |
| 139 | +++ |
| 140 | +++ |
| 141 | ++ |
| 142 | +++ |
| 143 | +++ |
| 144 | +++ |
| 145 | +++ |
| 146 | ++ |
| 147 | +++ |
| 148 | +++ |
| 149 | +++ |
| 150 | +++ |
| 151 | +++ |
| 152 | +++ |
| 153 | +++ |
| 154 | +++ |
| 155 | +++ |
| 156 | ++ |
| 157 | +++ |
| 158 | +++ |
| 159 | +++ |
| 160 | +++ |
| 162 | +++ |
| 163 | +++ |
| 164 | +++ |
| 165 | +++ |
| 166 | + |
| 167 | ++ |
| 168 | ++ |
| 169 | +++ |
| 170 | ++ |
| 171 | ++ |
| 172 | +++ |
| 173 | ++ |
| 174 | +++ |
| 175 | + |
| 176 | ++ |
| 177 | +++ |
| 178 | ++ |
| 179 | +++ |
| 180 | +++ |
| 181 | +++ |
| 182 | +++ |
| 183 | ++ |
| 184 | + |
| 185 | + |
| 186 | +++ |
| 187 | +++ |
| 188 | +++ |
| 189 | +++ |
| 190 | +++ |
| 191 | +++ |
| 192 | +++ |
| 193 | +++ |
| 194 | +++ |
| 195 | +++ |
| 196 | +++ |
| 197 | ++ |
| 198 | +++ |
| 199 | +++ |
| 200 | ++ |
| 201 | +++ |
| 202 | +++ |
| 203 | +++ |
| 204 | +++ |
| 205 | ++ |
| 206 | +++ |
| 207 | +++ |
| 208 | +++ |
| 209 | +++ |
| 210 | +++ |
| 211 | +++ |
| 212 | +++ |
| 213 | +++ |
| 214 | +++ |
| 215 | +++ |
| 216 | +++ |
| 217 | + |
| 218 | + |
| 219 | +++ |
| 220 | +++ |
| 221 | + |
| 222 | +++ |

TABLE 1-continued

Affinity to 5-HT5A (Ki)

| Example # | Binding affinity 5-HT5A (Ki) |
|---|---|
| 223 | +++ |
| 222 | +++ |
| 223 | +++ |
| 224 | +++ |
| 225 | +++ |
| 226 | +++ |

+ means an affinity >500 nM
++ means an affinity between 50 and 500 nM
+++ means an affinity <50 nM

The invention claimed is:
1. A guanidine compound of the formula I

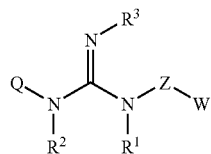

I corresponding enantiomeric, diastereomeric and/or tautomeric forms thereof, as well as pharmaceutically acceptable salts thereof, wherein the given moieties have the following definitions:

W:
 a moiety of the formula W1

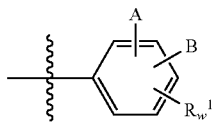

W1 wherein

A:
 $NO_2$, $NH_2$, OH, CN, $CF_3$, $OCF_3$, $CHF_2$, $OCHF_2$, COOH, O—$CH_2$—COOH, halogen, SH, or
 each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl, $C_1$-$C_4$-alkylene-hetaryl or $C_1$-$C_4$-alkylene-aryl, or
 O—$R_A^1$, CO—$R_A^1$, S—$R_A^1$, SO—$R_A^1$, CO—O—$R_A^1$, $NR_A^4$—CO—O—$R_A^1$, O—$CH_2$—COO—$R_A^1$, $NR_A^2R_A^3$, $CONH_2$, $SO_2NH_2$, $NR_A^4$—CO—$R_A^1$, $SO_2$—$R_A^1$, $NR_A^4$—$SO_2$—$R_A^1$, $SO_2$—$NR_A^2R_A^3$ or CO—$NR_A^2R_A^3$;

$R_A^1$:
 each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl, $C_1$-$C_4$-alkylene-aryl, $C_2$-$C_6$-alkenylene-aryl or $C_1$-$C_6$-alkylene-hetaryl;

$R_A^2$:
 hydrogen, OH, CN, or
 each optionally substituted $C_1$-$C_6$-alkyl, $C_2$-$C_6$-alkenyl, $C_2$-$C_6$-alkynyl, $C_1$-$C_4$-alkylene-$C_3$-$C_7$-cycloalkyl, $C_1$-$C_4$-alkylene-heterocycloalkyl, aryl, hetaryl, heterocycloalkyl, $C_1$-$C_4$-alkylene-aryl, $C_1$-$C_4$-alkylene-hetaryl, $C_1$-$C_6$-alkylene-O—$C_1$-$C_6$-alkyl, CO—$C_1$-$C_6$-alkyl, CO-aryl, CO-hetaryl, CO—$C_1$-$C_4$-alkylene-aryl, CO—$C_1$-$C_4$-alkylene-hetaryl, CO—O—$C_1$-$C_6$-alkyl, CO—O-aryl, CO—O—$C_1$-$C_4$-alkylene-aryl, CO—O-hetaryl, CO—O—$C_1$-$C_4$-alkylene-hetaryl, $SO_2$—$C_1$-$C_6$-alkyl, $SO_2$-aryl, $SO_2$-hetaryl, $SO_2$—$C_1$-$C_4$-alkylene-aryl or $SO_2$—$C_1$-$C_4$-alkylene-hetaryl;

$R_A^3$:
 each optionally substituted $C_1$-$C_6$-alkyl, $C_2$-$C_6$-alkenyl, $C_2$-$C_6$-alkynyl, $C_1$-$C_4$-alkylene-$C_3$-$C_7$-cycloalkyl, $C_1$-$C_4$-alkylene-heterocycloalkyl, aryl, hetaryl, heterocycloalkyl, $C_1$-$C_4$-alkylene-aryl, $C_1$-$C_4$-alkylene-hetaryl, $C_1$-$C_6$-alkylene-O—$C_1$-$C_6$-alkyl, CO—$C_1$-$C_6$-alkyl, CO-aryl, CO-hetaryl, CO—$C_1$-$C_4$-alkylene-aryl, CO—$C_1$-$C_4$-alkylene-hetaryl, CO—O—$C_1$-$C_6$-alkyl, CO—O-aryl, CO—O—$C_1$-$C_4$-alkylene-aryl, CO—O-hetaryl, CO—O—$C_1$-$C_4$-alkylene-hetaryl, $SO_2$—$C_1$-$C_6$-alkyl, $SO_2$-aryl, $SO_2$-hetaryl, $SO_2$—$C_1$-$C_4$-alkylene-aryl or $SO_2$—$C_1$-$C_4$-alkylene-hetaryl;
 or the moieties $R_A^2$ and $R_A^3$ form, together with the nitrogen, a 3 to 7-membered, optionally substituted, saturated or aromatic heterocycle which can contain one, two or three different or same heteroatoms from the group O, N, S; wherein optionally two moieties substituted on this heterocycle can together form an anellated, saturated, unsaturated or aromatic carbocycle or heterocycle, wherein the heterocycle can contain up to three different or same heteroatoms O, N, S, and wherein the cycle formed can optionally be substituted or a further, optionally substituted cycle can be condensed onto this cycle;

$R_A^4$:
 hydrogen or
 each optionally substituted $C_1$-$C_6$-alkyl, $C_1$-$C_6$-alkylene-O—$C_1$-$C_6$-alkyl, $C_2$-$C_6$-alkenyl, $C_3$-$C_{12}$-alkynyl, CO—$C_1$-$C_6$-alkyl, CO—O—$C_1$-$C_6$-alkyl, $SO_2$—$C_1$-$C_6$-alkyl, $C_3$-$C_7$-cycloalkyl, aryl, $C_1$-$C_4$-alkylene-aryl, CO—O-arylalkyl, CO—$C_1$-$C_4$-alkylene-aryl, CO-aryl, $SO_2$-aryl, hetaryl, CO-hetaryl or $SO_2$—$C_1$-$C_4$-alkylene-aryl;

B:
 hydrogen or as moiety A is defined,
 or each independently of one another, two of the moieties A, B or $R_W^1$ form, together with a 3 to 7-membered, optionally substituted, saturated or unsaturated carbocycle or an optionally substituted, saturated or unsaturated or aromatic heterocycle which can contain one, two or three further different or same heteroatoms from the group O, N, S; wherein optionally two of the moieties substituted on this carbo- or heterocycle can together form an anellated, saturated, unsaturated or aromatic carbocycle or heterocycle, wherein the heterocycle can contain up to three different or same heteroatoms O, N, S, and wherein the cycle formed can optionally be substituted or a further, optionally substituted cycle can be condensed onto this cycle;

$R_W^1$:
 hydrogen, OH, halogen, $NO_2$, $NH_2$, CN, $CF_3$, $CHF_2$, O—$CF_3$, O—$CHF_2$, or each optionally substituted $C_1$-$C_6$-alkyl, $C_3$-$C_7$-cycloalkyl, $C_1$-$C_6$-alkylene-O—$C_1$-$C_6$-alkyl, $C_1$-$C_6$-thioalkyl, aryl, hetaryl, O—$C_1$-$C_6$-alkyl, O-aryl, O-benzyl, $C_1$-$C_6$-alkylamino, $C_1$-$C_6$-dialkylamino, pyrrolidinyl, piperidinyl, morpholinyl, CO—$C_1$-$C_6$-alkyl, $SO_2$—$C_1$-$C_6$-alkyl, CO-aryl, $SO_2$-aryl, CO—$C_1$-$C_4$-alkylene-aryl, $SO_2$—$C_1$-$C_4$-alkylene-aryl, SO-aryl, $CONH_2$, CONH—$C_1$-$C_6$-alkyl, $SO_2NH$—$C_1$-$C_6$-alkyl, CON—($C_1$-$C_6$-alkyl)$_2$, $SO_2N$—($C_1$-$C_6$-alkyl)$_2$, NH—$SO_2$—$C_1$-$C_6$-alkyl or NH—CO—$C_1$-$C_6$-alkyl;

D:
as moiety A is defined;

Z:
each optionally substituted $C_{1-4}$-alkylene or $C_{1-4}$-alkyleneoxy;

$R^1$, $R^2$, $R^3$ independently of one another:
hydrogen, OH,
each optionally substituted $C_1$-$C_6$-alkyl, O—$C_1$-$C_6$-alkyl, $C_1$-$C_6$-alkylene-O—$C_1$-$C_6$-alkyl, $C_3$-$C_7$-cycloalkyl, O—$C_3$-$C_7$-cycloalkyl, aryl, hetaryl, $C_1$-$C_4$-alkylene-aryl, $C_1$-$C_4$-alkylene-hetaryl, O-aryl, O—$C_1$-$C_4$-alkylene-aryl, O-hetaryl, O—$C_1$-$C_4$-alkylene-hetaryl, CO—$C_1$-$C_6$-alkyl, CO-aryl, CO-hetaryl, CO—$C_1$-$C_4$-alkylene-aryl, CO—$C_1$-$C_4$-alkylene-hetaryl, CO—O—$C_1$-$C_6$-alkyl, CO—O-aryl, CO—O-hetaryl, CO—O—$C_1$-$C_4$-alkylene-aryl, $SO_2$—$C_1$-$C_6$-alkyl, $SO_2$-aryl, $SO_2$-hetaryl, $SO_2$—$C_1$-$C_4$-alkylene-aryl, OCO—$C_1$-$C_6$-alkyl, OCO-aryl, OCO-hetaryl, OCO—$C_1$-$C_4$-alkylene-aryl, OCO—$C_1$-$C_4$-alkylene-hetaryl, $SO_2$—$C_1$-$C_6$-alkyl, $SO_2$-aryl, $SO_2$-hetaryl or $SO_2$—$C_1$-$C_4$-alkylene-aryl, or
each independent from the third moiety two moieties of $R^1$, $R^2$ or $R^3$ together form a 5 to 7-membered, optionally substituted, saturated or unsaturated carbocycle or an optionally substituted, saturated or unsaturated heterocycle which can contain one, two or three further different or same heteroatoms from the group O, N, S, wherein optionally two moieties substituted on this carbo- or heterocycle together can form an anellated, saturated, unsaturated or aromatic carbocycle or heterocycle, wherein the heterocycle can contain up to three different or same heteroatoms O, N, S, and wherein the cycle formed can be optionally substituted or a further, optionally substituted cycle can be condensed onto this cycle;

Q:
a doubly substituted 5-membered hetaryl moiety of formula Q1

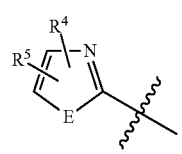

Q1

E: S;

$R_Q^1$:
hydrogen or
each optionally substituted $C_1$-$C_4$-alkyl, CO—$C_1$-$C_4$-alkyl, $SO_2$—$C_1$-$C_4$-alkyl, CO—O—$C_1$-$C_4$-alkyl, aryl, $C_1$-$C_4$-alkylene-aryl, CO-aryl, CO-hetaryl, $SO_2$-aryl, $SO_2$-hetaryl, CO-aryl, CO—$C_1$-$C_4$-alkylene-aryl, $SO_2$—$C_1$-$C_4$-alkylene-aryl or CO—O—$C_1$-$C_4$-alkylene-aryl;

$R^4$, $R^5$ each independently of one another a moiety chosen from the groups 1), 2), 3), 4), 5), 6) or 7):
1) hydrogen, halogen, CN, $CF_3$, $CHF_2$, or
each optionally substituted $C_1$-$C_{10}$-alkyl, $C_2$-$C_{10}$-alkenyl, $C_2$-$C_{10}$-alkynyl, $C_3$-$C_7$-cycloalkyl, $C_1$-$C_6$-alkylene-$C_3$-$C_7$-cycloalkyl, $C_1$-$C_4$-alkylene-aryl, $C_1$-$C_4$-alkylene-hetaryl, $C_1$-$C_6$-alkylene-O—$C_1$-$C_6$-alkyl, $C_1$-$C_6$-alkylene-O-aryl, COO—$C_1$-$C_4$-alkyl or $C_1$-$C_4$-alkylene-COO—$C_1$-$C_4$-alkyl;
2) Phenyl or naphthyl, which are each substituted with $R_Q^2$, $R_Q^3$ and $R_Q^4$, wherein
$R_Q^2$, $R_Q^3$ and $R_Q^4$ each independently of one another represent a substituent from the following group:
hydrogen, $NO_2$, $NH_2$, OH, CN, $CF_3$, $CHF_2$, $OCF_3$, $OCHF_2$, COOH, O—$CH_2$—COOH, SH, halogen, or
each optionally substituted aryl, hetaryl, heterocycloalkyl, $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, $C_1$-$C_4$-alkylene-aryl or $C_1$-$C_4$-alkylene-hetaryl, or
O—$R_Q^5$, S—$R_Q^5$, $NR_Q^7R_Q^8$, CO—$OR_Q^6$, $NR_Q^8$—COO—O—$R_Q^6$, O—$CH_2$—COO—$R_Q^6$, $NR_Q^8$—CO—$R_Q^6$, $SO_2$—$R_Q^6$, $NR_Q^8$—$SO_2$—$R_Q^6$, $SO_2NH_2$, $CONH_2$, $SO_2$—$NR_Q^7R_Q^8$ or CO—$NR_Q^7R_Q^8$, or
two of the moieties $R_Q^2$, $R_Q^3$ or $R_Q^4$ together form a 3 to 7-membered, optionally substituted, saturated, unsaturated or aromatic carbocycle or a an optionally substituted, saturated, unsaturated aromatic heterocycle which can contain up to three further different or same heteroatoms O, N, S and optionally two of the moieties substituted on this heterocycle can together form an anellated, saturated, unsaturated or aromatic carbocycle or heterocycle, wherein the heterocycle can contain up to three different or same heteroatoms O, N, S and the cycle formed can be optionally substituted or a further, optionally substituted cycle can be condensed onto this cycle;

$R_Q^5$ each optionally substituted $C_2$-$C_6$-alkenyl, $C_2$-$C_6$-alkynyl, $C_1$-$C_4$-alkylene-$C_3$-$C_7$-cycloalkyl, $C_1$-$C_4$-alkylene-heterocycloalkyl, heterocycloalkyl or hetaryl, or
$C_1$-$C_6$-alkyl, which is optionally substituted with a substituent from the group consisting of halogen, $NO_2$, $NH_2$, OH, CN, $CF_3$, $CHF_2$, $OCF_3$, $OCHF_2$, NH—($C_1$-$C_6$-alkyl) and N($C_1$-$C_6$-alkyl)$_2$;

$R_Q^6$ each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl or $C_1$-$C_6$-alkylene-O—$C_1$-$C_6$-alkyl;

$R_Q^7$ hydrogen, OH, CN, or
each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl, $C_1$-$C_6$-alkylene-O—$C_1$-$C_6$-alkyl, CO—$C_1$-$C_6$-alkyl, $C_1$-$C_4$-alkylene-aryl, $C_1$-$C_4$-alkylene-hetaryl, CO-aryl, CO-hetaryl, CO—$C_1$-$C_4$-alkylene-aryl, CO—$C_1$-$C_4$-alkylene-hetaryl, CO—O—$C_1$-$C_6$-alkyl, CO—O-aryl, CO—O—$C_1$-$C_4$-alkylene-aryl, CO—O-hetaryl, CO—O—$C_1$-$C_4$-alkylene-hetaryl, $SO_2$—$C_1$-$C_6$-alkyl, $SO_2$-aryl, $SO_2$-hetaryl, $SO_2$—$C_1$-$C_4$-alkylene-aryl or $SO_2$—$C_1$-$C_4$-alkylene-hetaryl;

$R_Q^8$ hydrogen or
each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$- alkylene-$C_3$-$C_7$-cycloalkyl, $C_1$-$C_4$-alkylene-heterocycloalkyl, aryl, hetaryl, heterocycloalkyl, $C_1$-$C_6$-alkylene-O—$C_1$-$C_6$-alkyl, CO—$C_1$-$C_6$-alkyl, CO-aryl, CO-hetaryl, CO—$C_1$-$C_4$-alkylene-aryl, CO—$C_1$-$C_4$-alkylene-hetaryl, CO—O—$C_1$-$C_6$-alkyl, CO—O-aryl, CO—O—$C_1$-$C_4$-alkylene-aryl, CO—O-hetaryl, CO—O—$C_1$-$C_4$-alkylene-hetaryl, $SO_2$—$C_1$-$C_6$-alkyl, $SO_2$-aryl, $SO_2$-hetaryl, $SO_2$—$C_1$-$C_4$-alkylene-aryl or $SO_2$—$C_1$-$C_4$-alkylene-hetaryl;

or the moieties $R_Q^7$ and $R_Q^8$, together with the nitrogen, form a 3 to 7-membered, optionally substituted, saturated or aromatic heterocycle, which can contain one, two or three further different or same heteroatoms O, N, S; and optionally two of the moieties substituted on this heterocycle can together form an anellated, saturated, unsaturated or aromatic carbocycle or heterocycle, wherein the heterocycle can contain up to three different or identical heteroatoms O, N, S, and the cycle formed can optionally be substituted or a further, optionally substituted cycle can be condensed onto this cycle;

3) a 5- or 6-membered hetaryl moiety optionally substituted with 1 or 2 substituents, the hetaryl moiety chosen from the group consisting of:
2-pyrrolyl, 3-pyrrolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl or triazinyl or their anellated derivatives indazolyl, benzothiophenyl, benzofuranyl, indolinyl, benzimidazolyl, benzthiazolyl, benzoxazolyl, quinolinyl and isoquinolinyl; or 2-thienyl or 3-thienyl optionally substituted with one or two substituents, wherein the substituents are chosen from the group consisting of halogen, $NO_2$, $NH_2$, OH, CN, $CF_3$, $OCF_3$, $CHF_2$, O—$CHF_2$, $C_1$-$C_6$-alkyl, O—$C_1$-$C_6$-alkyl, NH—($C_1$-$C_6$-alkyl), N($C_1$-$C_6$-alkyl)$_2$, NHCO—$C_1$-$C_4$-alkyl, $NHSO_2$—$C_1$-$C_4$-alkyl and $SO_2$—$C_1$-$C_4$-alkyl;

4) both moieties $R^4$ and $R^5$ together form a 4 to 7-membered, optionally substituted, saturated or unsaturated or aromatic carbocycle or a 5- or 6-membered optionally substituted, saturated or unsaturated or aromatic heterocycle, which can contain up to three further different or identical heteroatoms O, N, S; and can be substituted with up to two further moieties, wherein optionally two moieties substituted on this carbo or hetero cycle can together form an anellated, saturated, unsaturated or aromatic carbo cycle or heterocycle, wherein the heterocycle can contain up to three different or identical heteroatoms O, N, S and wherein the cycle formed can be optionally substituted or a further, optionally substituted cycle can be condensed onto this cycle;

5) a $C_5$-$C_{18}$-bi- or tricyclic, saturated hydrocarbon moiety;

6) each optionally substituted $C_1$-$C_8$-Alkyl-$NH_2$, $C_1$-$C_8$-Alkyl-$NR_Q^7R_Q^8$, $C_1$-$C_8$-Alkyl-CO—$NR_Q^7R_Q^8$, $C_1$-$C_8$-Alkyl-$SO_2NR_Q^7R_Q^8$, $C_1$-$C_8$-Alkyl-CO—$NH_2$, $C_1$-$C_8$-Alkyl-$SO_2NH_2$, CO—$NH_2$, CO—$NR_Q^7R_Q^8$, $SO_2NH_2$, $SO_2NR_Q^7R_Q^8$, $NR_Q^7R_Q^8$;

7) a 4-7-membered monocyclic saturated heterocycle or bicyclic saturated or unsaturated heterocycle, which can contain up to two different or identical heteroatoms from the group O, N or S, wherein this cycle can also be multiply substituted; for the case that the heterocycle contains an N-atom, this can be substituted with a moiety $R_Q^7$.

2. A guanidine compound of the formula I

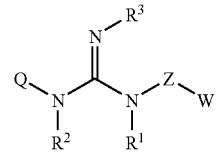

I corresponding enantiomeric, diastereomeric and/or tautomeric forms thereof as well as pharmaceutically acceptable salts thereof, wherein the given moieties have the following definitions:

W:
a moiety of the formula W1

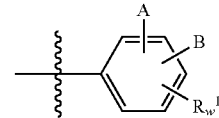

W1 wherein
A:
$NO_2$, $NH_2$, OH, CN, $CF_3$, $OCF_3$, $CHF_2$, $OCHF_2$, COOH, O—$CH_2$—COOH, halogen, SH, or each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl, $C_1$-$C_4$-alkylene-hetaryl or $C_1$-$C_4$-alkylene-aryl, or O—$R_A^1$, CO—$R_A^1$, SO—$R_A^1$, $SO_2$—$R_A^1$, CO—O—$R_A^1$, $NR_A^4$—CO—O—$R_A^1$, O—$CH_2$—COO—$R_A^1$, $NR_A^2R_A^3$, $CONH_2$, $SO_2NH_2$, $NR_A^4$—CO—$R_A^1$, $SO_2$—$R_A^1$, $NR_A^4$—$SO_2$—$R_A^1$, $SO_2$—$NR_A^2R_A^3$ or CO—$NR_A^2R_A^3$;

$R_A^1$:
each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl, $C_1$-$C_4$-alkylene-aryl, $C_2$-$C_6$-alkenylene-aryl or $C_1$-$C_6$-alkylene-hetaryl;

$R_A^2$:
hydrogen, OH, CN, or
each optionally substituted $C_1$-$C_6$-alkyl, $C_2$-$C_6$-alkenyl, $C_2$-$C_6$-alkynyl, $C_1$-$C_4$-alkylene-$C_3$-$C_7$-cycloalkyl, $C_1$-$C_4$-alkylene-heterocycloalkyl, aryl, hetaryl, heterocycloalkyl, $C_1$-$C_4$-alkylene-aryl, $C_1$-$C_4$-alkylene-hetaryl, $C_1$-$C_6$-alkylene-O—$C_1$-$C_6$-alkyl, CO—$C_1$-$C_6$-alkyl, CO-aryl, CO-hetaryl, CO—$C_1$-$C_4$-alkylene-aryl, CO—$C_1$-$C_4$-alkylene-hetaryl, CO—O—$C_1$-$C_6$-alkyl, CO—O-aryl, CO—O—$C_1$-$C_4$-alkylene-aryl, CO—O-hetaryl, CO—O—$C_1$-$C_4$-alkylene-hetaryl, $SO_2$—$C_1$-$C_6$-alkyl, $SO_2$-aryl, $SO_2$-hetaryl, $SO_2$—$C_1$-$C_4$-alkylene-aryl or $SO_2$—$C_1$-$C_4$-alkylene-hetaryl;

$R_A^3$:
each optionally substituted $C_1$-$C_6$-alkyl, $C_2$-$C_6$-alkenyl, $C_2$-$C_6$-alkynyl, $C_1$-$C_4$-alkylene-$C_3$-$C_7$-cycloalkyl, C$_1$-C$_4$-alkylene-heterocycloalkyl, aryl, hetaryl, heterocycloalkyl, C$_1$-C$_4$-alkylene-aryl, C$_1$-C$_4$-alkylene-hetaryl, C$_1$-C$_6$-alkylene-O—C$_1$-C$_6$-alkyl, CO—C$_1$-C$_6$-alkyl, CO-aryl, CO-hetaryl, CO—C$_1$-C$_4$-alkylene-aryl, CO—C$_1$-C$_4$-alkylene-hetaryl, CO—O—C$_1$-C$_6$-alkyl, CO—O-aryl, CO—O—C$_1$-C$_4$-alkylene-aryl, CO—O-hetaryl, CO—O—C$_1$-C$_4$-alkylene-hetaryl, SO$_2$—C$_1$-C$_6$-alkyl, SO$_2$-aryl, SO$_2$-hetaryl, SO$_2$—C$_1$-C$_4$-alkylene-aryl or SO$_2$—C$_1$-C$_4$-alkylene-hetaryl;

or the moieties R$_A^2$ and R$_A^3$ form, together with the nitrogen, a 3 to 7-membered, optionally substituted, saturated or aromatic heterocycle, which can contain one, two or three further different or identical heteroatoms from the group O, N, S; wherein optionally two of the moieties substituted on this heterocycle can together form an anellated, saturated, unsaturated or aromatic carbocycle or heterocycle, wherein the heterocycle can contain up to three different or identical heteroatoms O, N, S and wherein the so-formed cycle can be optionally substituted or a further, optionally substituted cycle can be condensed onto this cycle;

R$_A^4$:

hydrogen, or each optionally substituted C$_1$-C$_6$-alkyl, C$_1$-C$_6$-alkylene-O—C$_1$-C$_6$-alkyl, C$_2$-C$_6$-alkenyl, C$_3$-C$_{12}$-alkynyl, CO—C$_1$-C$_6$-alkyl, CO—O—C$_1$-C$_6$-alkyl, SO$_2$—C$_1$-C$_6$-alkyl, C$_3$-C$_7$-cycloalkyl, aryl, C$_1$-C$_4$-alkylene-aryl, CO—O-arylalkyl, CO—C$_1$-C$_4$-alkylene-aryl, CO-aryl, SO$_2$-aryl, hetaryl, CO-hetaryl or SO$_2$—C$_1$-C$_4$-alkylene-aryl;

B:

hydrogen or as moiety A is defined, or each independently of one another, two of the moieties A, B or R$_w^1$ together form a 3 to 7-membered, optionally substituted, saturated or unsaturated carbocycle or an optionally substituted, saturated or unsaturated or aromatic heterocycle which can contain one, two or three further different or identical heteroatoms from the group O, N, S; wherein optionally two moieties substituted on this carbo- or heterocycle can together form an anellated, saturated, unsaturated or aromatic carbocycle or heterocycle, wherein the heterocycle can contain up to three different or identical heteroatoms O, N, S and wherein the cycle formed can optionally be substituted or a further, optionally substituted cycle can be condensed onto this cycle;

R$_W^1$:

hydrogen, OH, halogen, NO$_2$, NH$_2$, CN, CF$_3$, CHF$_2$, O—CF$_3$, O—CHF$_2$, or each optionally substituted C$_1$-C$_6$-alkyl, C$_3$-C$_7$-cycloalkyl, C$_1$-C$_6$-alkylene-O—C$_1$-C$_6$-alkyl, C$_1$-C$_6$-thioalkyl, aryl, hetaryl, O—C$_1$-C$_6$-alkyl, O-aryl, O-benzyl, C$_1$-C$_6$-alkylamino, C$_1$-C$_6$-dialkylamino, pyrrolidinyl, piperidinyl, morpholinyl, CO—C$_1$-C$_6$-alkyl, SO$_2$—C$_1$-C$_6$-alkyl, CO-aryl, SO$_2$-aryl, CO—C$_1$-C$_4$-alkylene-aryl, SO$_2$—C$_1$-C$_4$-alkylene-aryl, SO-aryl, CONH$_2$, CONH—C$_1$-C$_6$-alkyl, SO$_2$NH—C$_1$-C$_6$-alkyl, CON—(C$_1$-C$_6$-alkyl)$_2$, SO$_2$N—(C$_1$-C$_6$-alkyl)$_2$, NH—SO$_2$C$_1$-C$_6$-alkyl or NH—CO—C$_1$-C$_6$-alkyl;

D:

as moiety A is defined;

Z:

each optionally substituted C$_{1-4}$-alkylene or C$_{1-4}$-alkyleneoxy;

R$^1$, R$^2$, R$^3$ independently of one another:

hydrogen, OH, or each optionally substituted C$_1$-C$_6$-alkyl, O—C$_1$-C$_6$-alkyl, C$_1$-C$_6$-alkylene-O—C$_1$-C$_6$-alkyl, C$_3$-C$_7$-cycloalkyl, O—C$_3$-C$_7$-cycloalkyl, aryl, hetaryl, C$_1$-C$_4$-alkylene-aryl, C$_1$-C$_4$-alkylene-hetaryl, O-aryl, O—C$_1$-C$_4$-alkylene-aryl, O-hetaryl, O—C$_1$-C$_4$-alkylene-hetaryl, CO—C$_1$-C$_6$-alkyl, CO-aryl, CO-hetaryl, CO—C$_1$-C$_4$-alkylene-aryl, CO—C$_1$-C$_4$-alkylene-hetaryl, CO—O—C$_1$-C$_6$-alkyl, CO—O-aryl, CO—O-hetaryl, CO—O—C$_1$-C$_4$-alkylene-aryl, SO$_2$—C$_1$-C$_6$-alkyl, SO$_2$-aryl, SO$_2$-hetaryl, SO$_2$—C$_1$-C$_4$-alkylene-aryl, OCO—C$_1$-C$_6$-alkyl, OCO-aryl, OCO-hetaryl, OCO—C$_1$-C$_4$-alkylene-aryl, OCO—C$_1$-C$_4$-alkylene-hetaryl, SO$_2$—C$_1$-C$_6$-alkyl, SO$_2$-aryl, SO$_2$-hetaryl or SO$_2$—C$_1$-C$_4$-alkylene-aryl, or each independently of the third moiety, two moieties of R$^1$, R$^2$ or R$^3$ together form a 5 to 7-membered, optionally substituted, saturated or unsaturated carbocycle or an optionally substituted, saturated or unsaturated heterocycle which can contain one, two or three further different or identical heteroatoms from the group O, N, S, wherein optionally two of the moieties substituted on this carbo- or heterocycle can together form an anellated, saturated, unsaturated or aromatic carbocycle or heterocycle wherein the heterocycle can contain up to three different or identical heteroatoms O, N, S and wherein the cycle formed is optionally substituted or a further, optionally substituted cycle is condensed onto this cycle;

Q:

a doubly substituted 5-membered hetaryl moiety of formula Q1

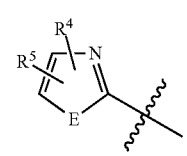

Q1

E: S;

R$_Q^1$:

hydrogen, or each optionally substituted C$_1$-C$_4$-alkyl, CO—C$_1$-C$_4$-alkyl, SO$_2$—C$_1$-C$_4$-alkyl, CO—O—C$_1$-C$_4$-alkyl, aryl, C$_1$-C$_4$-alkylene-aryl, CO-aryl, CO-hetaryl, SO$_2$-aryl, SO$_2$-hetaryl, CO—O-aryl, CO—C$_1$-C$_4$-alkylene-aryl, SO$_2$—C$_1$-C$_4$-alkylene-aryl or CO—O—C$_1$-C$_4$-alkylene-aryl;

R$^4$, R$^5$ each independently of one another a moiety chosen from the groups 1), 2), 3), 4) or 5):

1) hydrogen, halogen, CN, CF$_3$, CHF$_2$, or each optionally substituted C$_1$-C$_{10}$-alkyl, C$_2$-C$_{10}$-alkenyl, C$_2$-C$_{10}$-alkynyl, C$_3$-C$_7$-cycloalkyl, C$_1$-C$_6$-alkylene-C$_3$-C$_7$-cycloalkyl, C$_1$-C$_4$-alkylene-aryl, C$_1$-C$_4$-alkylene-hetaryl, C$_1$-C$_6$-alkylene-O—C$_1$-C$_6$-alkyl, C$_1$-C$_6$-alkylene-O-aryl, COO—C$_1$-C$_4$-alkyl or C$_1$-C$_4$-alkylene-COO—C$_1$-C$_4$-alkyl;

2) Phenyl or naphthyl, which are each substituted with $R_Q^2$, $R_Q^3$ and $R_Q^4$, wherein $R_Q^2$, $R_Q^3$ and $R_Q^4$ each independently of one another represent a substituent from the following group:

hydrogen, $NO_2$, $NH_2$, OH, CN, $CF_3$, $CHF_2$, $OCF_3$, $OCHF_2$, COOH, O—$CH_2$—COOH, SH, halogen, or each optionally substituted aryl, hetaryl, heterocycloalkyl, $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, $C_1$-$C_4$-alkylene-aryl or $C_1$-$C_4$-alkylene-hetaryl, or O—$R_Q^5$, S—$R_Q^5$, $NR_Q^7R_Q^8$, CO—$OR_Q^6$, $NR_Q^8$—CO—$R_Q^6$, O—$CH_2$—COO—$R_Q^6$, $NR_Q^8$—CO—$R_Q^6$, $SO_2$—$R_Q^6$, $NR_Q^8$—$SO_2$—$R^6$, $SO_2NH_2$, $CONH_2$, $SO_2$—$NR_Q^7R_Q^8$ or CO—$NR_Q^7R_Q^8$ or two of the moieties $R_Q^2$, $R_Q^3$ or $R_Q^4$ together form a 3 to 7-membered, optionally substituted, saturated, unsaturated or aromatic carbocycle or an optionally substituted, saturated or unsaturated aromatic heterocycle, which can contain up to three further different or identical heteroatoms O, N, S and optionally two moieties substituted on this heterocycle can together form an anellated, saturated, unsaturated or aromatic carbocycle or heterocycle, wherein the heterocycle can contain up to three different or identical heteroatoms O, N, S and the cycle formed can optionally be substituted or a further, optionally substituted cycle can be condensed onto this cycle;

$R_Q^5$ each optionally substituted $C_2$-$C_6$-alkenyl, $C_2$-$C_6$-alkynyl, $C_1$-$C_4$-alkylene-$C_3$-$C_7$-cycloalkyl, $C_1$-$C_4$-alkylene-heterocycloalkyl, heterocycloalkyl or hetaryl, or $C_1$-$C_6$-alkyl, which is optionally substituted with a substituent from the group consisting of halogen, $NO_2$, $NH_2$, OH, CN, $CF_3$, $CHF_3$, $OCF_3$, $OCHF_2$, NH—($C_1$-$C_6$-alkyl) and N($C_1$-$C_6$-alkyl)$_2$;

$R_Q^6$ each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl or $C_1$-$C_6$-alkylene-O—$C_1$-$C_6$-alkyl;

$R_Q^7$ hydrogen, OH, CN, or each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl, $C_1$-$C_6$-alkylene-O—$C_1$-$C_6$-alkyl, CO—$C_1$-$C_6$-alkyl, $C_1$-$C_4$-alkylene-aryl, $C_1$-$C_4$-alkylene-hetaryl, CO-aryl, CO-hetaryl, CO—$C_1$-$C_4$-alkylene-aryl, CO—$C_1$-$C_4$-alkylene-hetaryl, CO—O—$C_1$-$C_6$-alkyl, CO—O-aryl, CO—O—$C_1$-$C_4$-alkylene-aryl, CO—O-hetaryl, CO—O—$C_1$-$C_4$-alkylene-hetaryl, $SO_2$—$C_1$-$C_6$-alkyl, $SO_2$-aryl, $SO_2$-hetaryl, $SO_2$—$C_1$-$C_4$-alkylene-aryl or $SO_2$—$C_1$-$C_4$-alkylene-hetaryl;

$R_Q^8$ each optionally substituted $C_1$-$C_6$-alkyl, $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl, $C_1$-$C_4$-alkylene-heterocycloalkyl, aryl, hetaryl, heterocycloalkyl, $C_1$-$C_6$-alkylene-O—$C_1$-$C_6$-alkyl, CO—$C_1$-$C_6$-alkyl, CO-aryl, CO-hetaryl, CO—$C_1$-$C_4$-alkylene-aryl, CO—$C_1$-$C_4$-alkylene-hetaryl, CO—O—$C_1$-$C_6$-alkyl, CO—O-aryl, CO—O—$C_1$-$C_4$-alkylene-aryl, CO—O-hetaryl, CO—O—$C_1$-$C_4$-alkylene-hetaryl, $SO_2$—$C_1$-$C_6$-alkyl, $SO_2$-aryl, $SO_2$-hetaryl, $SO_2$—$C_1$-$C_4$-alkylene-aryl or $SO_2$—$C_1$-$C_4$-alkylene-hetaryl;

or the moieties $R_Q^7$ and $R_Q^8$ form, together with the nitrogen, a 3 to 7-membered, optionally substituted, saturated or aromatic heterocycle which can contain one, two or three further or different identical heteroatoms O, N, S; and optionally two moieties substituted on this heterocycle can form an anellated, saturated, unsaturated or aromatic carbocycle or heterocycle, wherein the heterocycle can contain up to three different or identical heteroatoms O, N, S and the cycle formed can optionally be substituted or a further, optionally substituted cycle can be condensed onto this cycle;

3) a 5- or 6-membered hetaryl moiety optionally substituted with one or two substituents from the group consisting of:

2-pyrrolyl, 3-pyrrolyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl or triazinyl or their anellated derivatives indazolyl, benzothiophenyl, benzofuranyl, indolinyl, benzimidazolyl, benzthiazolyl, benzoxazolyl, quinolinyl and isoquinolinyl; or 2-thienyl or 3-thienyl optionally substituted with one or two substituents, wherein the substituents are chosen from the group consisting of halogen, $NO_2$, $NH_2$, OH, CN, $CF_3$, $OCF_3$, $CHF_2$, O—$CHF_2$, $C_1$-$C_6$-alkyl, O—$C_1$-$C_6$-alkyl, NH—($C_1$-$C_6$-alkyl), N($C_1$-$C_6$-alkyl)$_2$, NHCO—$C_1$-$C_4$-alkyl, $NHSO_2$—$C_1$-$C_4$-alkyl and $SO_2$—$C_1$-$C_4$-alkyl;

4) both moieties $R^4$ and $R^5$ together form a 4 to 7-membered, optionally substituted, saturated or unsaturated or aromatic carbocycle or a 5- or 6-membered optionally substituted, saturated or unsaturated or aromatic heterocycle, which can contain up to three further different or identical heteroatoms O, N, S and can be substituted with up to two further moieties, wherein optionally two moieties substituted on this carbo- or heterocycle can form an anellated, saturated, unsaturated or aromatic carbocycle or heterocycle, wherein the heterocycle can contain up to three different or identical heteroatoms O, N, S and wherein the cycle formed can be optionally substituted or a further, optionally substituted cycle can be condensed onto this cycle;

5) a $C_5$-$C_1$— bi- or tricyclic, saturated hydrocarbon moiety.

3. The compound according to claim 1, wherein the given moieties have the following definition:

W: W1;

A: halogen, OH, CN, $CF_3$, $CHF_2$, $OCF_3$, $OCHF_2$, or each optionally substituted $C_1$-$C_6$-alkyl or $C_2$-$C_6$-alkenyl, O—$CH_2$—COO—$R_A^1$, O—$R_A^1$, S—$R_A^1$, $NR_A^2R_A^3$, $NR_A^4$—CO—$R_A^1$ or CO—$NR_A^4R_A^1$;

$R_A^1$: each optionally substituted $C_1$-$C_4$-alkyl, $C_3$-$C_7$-cycloalkyl, phenyl or benzyl;

$R_A^2$: hydrogen, or each optionally substituted $C_1$-$C_4$-alkyl, phenyl, benzyl, phenethyl, CO—$C_1$-$C_4$-alkyl, CO-aryl, CO—O—

$C_1$-$C_4$-alkyl, $SO_2$—$C_1$-$C_4$-alkyl, $SO_2$-aryl, $SO_2$-hetaryl or $SO_2$—$C_1$-$C_4$-alkylene-aryl;

$R_A^3$: each optionally substituted $C_1$-$C_4$-alkyl, phenyl, benzyl, phenethyl, CO—$C_1$-$C_4$-alkyl, CO-aryl, CO—O—$C_1$-$C_4$-alkyl, $SO_2$—$C_1$-$C_4$-alkyl, $SO_2$-aryl, $SO_2$-hetaryl, or $SO_2$—$C_1$-$C_4$-alkylene-aryl;

or the moieties $R_A^2$ and $R_A^3$ together form an optionally substituted 5- or 6-membered saturated or unsaturated ring, which can contain up to two identical or different heteroatoms from the group O and N;

$R_A^4$: hydrogen or an optionally substituted $C_1$-$C_4$-alkyl moiety;

B: hydrogen or as moiety A is defined;

$R_W^1$: hydrogen, F, Cl, CN, $CF_3$, O—$CF_3$, or
each optionally substituted $C_1$-$C_4$-alkyl, aryl, $C_1$-$C_6$-alkylamino or $C_1$-$C_6$-dialkylamino;

$R^1$, $R^2$, $R^3$ independently of one another:
hydrogen, OH, $C_1$-$C_4$-alkyl, $C_1$-$C_6$-alkylene-O—$C_1$-$C_6$-alkyl, substituted aryl, benzyl, CO—$C_1$-$C_6$-alkyl, CO-aryl, CO—$C_1$-$C_4$-alkylene-aryl, OCO—$C_1$-$C_6$-alkyl, OCO-aryl or OCO—$C_1$-$C_4$-alkylene-hetaryl;

Q is Q1;

$R_Q^1$: hydrogen, optionally substituted $C_1$-$C_4$-alkyl, in the aryl moiety optionally substituted benzyl, CO—$C_1$-$C_4$-alkyl, optionally substituted benzoyl, $SO_2$—$C_1$-$C_4$-alkyl or in the aryl moiety optionally substituted $SO_2$-aryl.

4. The compound according to claim 1, wherein the given moieties have the following definitions:
A: OH, F, Cl, $OCF_3$, $OCHF_2$, optionally substituted $C_1$-$C_4$-alkyl, O—$C_1$-$C_4$-alkyl or S—$C_1$-$C_4$-alkyl;
B: hydrogen, OH, F, Cl, $CF_3$, $OCF_3$, $OCHF_2$, optionally substituted $C_1$-$C_4$-alkyl, O—$C_1$-$C_4$-alkyl or S—$C_1$-$C_4$-alkyl;
$R_W^1$: hydrogen, F, Cl, CN, $CF_3$ or O—$CF_3$;
$R^1$, $R^2$, $R^3$ independently of one another:
hydrogen, OH, O-methyl, O-phenyl, acetyl, benzoyl, O-acetyl, or O-benzoyl;
Q is chosen from the group consisting of

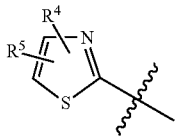

$R_Q^1$: hydrogen, $CH_3$, methanesulfonyl, phenylsulfonyl or tosyl.

5. The compound according to claim 1, wherein the given moieties have the following definitions:
A: OH, $OCF_3$, $OCH_3$, O-ethyl, O-propyl or O-i-propyl;
Z: —$CH_2$—, —$CH_2$—O—, —$CH_2$—$CH_2$— or —$CH_2$—$CH_2$—O—;
two of the moieties $R^1$, $R^2$, or $R^3$, are hydrogen, and the third moiety is hydrogen, OH, acetyl or benzoyl;
Q:

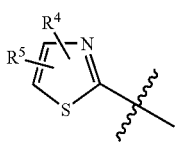

6. The compound according to claim 1, wherein $R^4$ and/or $R^5$ each independently of one another represents a moiety chosen from the groups 1), 2), 3), 4) or 5):
1) hydrogen, F, Cl, CN, $CF_3$, or
each optionally substituted $C_1$-$C_6$-alkyl, $C_2$-$C_6$-alkenyl, $C_1$-$C_6$-alkylene-O—$C_1$-$C_6$-alkyl or $C_3$-$C_7$-cycloalkyl;
2) Phenyl or naphthyl, which are each substituted with $R_Q^2$, $R_Q^3$, and $R_Q^4$, wherein
$R_Q^2$, $R_Q^3$, and $R_Q^4$ each independently of one another represent a substituent from the following group:
hydrogen, CN, $CF_3$, $CHF_2$, $OCF_3$, $OCHF_2$, F, Cl, OH or each optionally substituted phenyl or hetaryl, $C_1$-$C_4$-alkyl, $C_5$-$C_7$-cycloalkyl, O—$R_Q^5$, $NR_Q^7R_Q^8$, CO—$OR_Q^6$, $NR_Q^8$—CO—O—$R_Q^6$, O—$CH_2$—COO—$R_Q^6$, $NR_Q^8$—CO—$R_Q^6$, $SO_2$—$R_Q^6$, $NR_Q^8$—$SO_2$—$R_Q^6$, $NR_Q^8$—CO—O—$R_Q^6$, $SO_2NH_2$, $CONH_2$, $SO_2$—$NR_Q^7R_Q^8$ or CO—$NR_Q^7R_Q^8$;
$R_Q^5$: $C_1$-$C_4$-Alkyl, which is optionally substituted with a substituent from the group consisting of F, Cl, OH, CN, $CF_3$, $OCF_3$, NH—($C_1$-$C_4$-alkyl) and N($C_1$-$C_4$-alkyl)$_2$;
$R_Q^6$: each optionally substituted $C_1$-$C_6$-alkyl, aryl, hetaryl or phenyl;
$R_Q^7$: hydrogen, each optionally substituted $C_1$-$C_4$-alkyl, allyl, aryl, hetaryl, benzyl, phenethyl or $CH_2$-hetaryl;
$R_Q^8$, each optionally substituted $C_1$-$C_4$-alkyl, allyl, aryl, hetaryl, benzyl, phenethyl or $CH_2$-hetaryl;
or $R_Q^7$ and $R_Q^8$ form an optionally substituted 3- or 7-membered saturated or unsaturated ring which can contain up to two identical or different hetero atoms from the group O and N;
3) benzothiophenyl, benzofuranyl, quinolinyl and isoquinolinyl;
4) both moieties $R^4$ and $R^5$ together form one of the following rings:

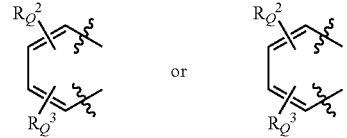

wherein $R_Q^2$ and $R_Q^3$ are as defined under 2);
5) Adamantyl.

7. The compound according to claim 1, wherein the given moieties have the following definitions:
W: W1;
A: halogen, OH, CN, $CF_3$, $CHF_2$, $OCF_3$, $OCHF_2$, or
each optionally substituted $C_1$-$C_6$-alkyl or $C_2$-$C_6$-alkenyl,
O—$CH_2$—COO—$R_A^1$, O—$R_A^1$, S—$R_A^1$, $NR_A^2R_A^3$, $NR_A^4$—CO—$R_A^1$, $SO_2NH_2$, $NR_A^4$—$SO_2$—$R_A^1$, $SO_2$—$NR_A^2R_A^3$ or CO—$NR_A^4R_A^1$;
$R_A^1$: each optionally substituted $C_1$-$C_4$-alkyl, $C_3$-$C_7$-cycloalkyl, phenyl or benzyl;
$R_A^2$: hydrogen, or
each optionally substituted $C_1$-$C_4$-alkyl, phenyl, benzyl, phenethyl, CO—$C_1$-$C_4$-alkyl, CO-aryl, CO—O—$C_1$-$C_4$-alkyl, $SO_2$—$C_1$-$C_4$-alkyl, $SO_2$-aryl, $SO_2$-hetaryl or $SO_2$—$C_1$-$C_4$-alkylene-aryl;
$R_A^3$: each optionally substituted $C_1$-$C_4$-alkyl, phenyl, benzyl, phenethyl, CO—$C_1$-$C_4$-alkyl, CO-aryl, CO—O—$C_1$-$C_4$-alkyl, $SO_2$—$C_1$-$C_4$-alkyl, $SO_2$-aryl, $SO_2$-hetaryl, or $SO_2$—$C_1$-$C_4$-alkylene-aryl;

or the moieties $R_A^2$ and $R_A^3$ together form an optionally substituted 5- or 6-membered saturated or unsaturated ring, which can contain up to two identical or different heteroatoms from the group O and N;

$R_A^4$: hydrogen or an optionally substituted $C_1$-$C_4$-alkyl moiety;

B: hydrogen or as moiety A is defined;

$R_W^1$: hydrogen, F, Cl, CN, $CF_3$, O—$CF_3$, or each optionally substituted $C_1$-$C_4$-alkyl, aryl, $C_1$-$C_6$-alkylamino or $C_1$-$C_6$-dialkylamino;

$R^1$, $R^2$, $R^3$ independently of one another:
hydrogen, OH, $C_1$-$C_4$-alkyl, $C_1$-$C_6$-alkylene-O—$C_1$-$C_6$-alkyl, substituted aryl, benzyl, CO—$C_1$-$C_6$-alkyl, CO-aryl, CO—$C_1$-$C_4$-alkylene-aryl, OCO—$C_1$-$C_6$-alkyl, OCO-aryl or OCO—$C_1$-$C_4$-alkylene-hetaryl;

Q is Q1;

$R_Q^1$: hydrogen, optionally substituted $C_1$-$C_4$-alkyl, in the aryl moiety optionally substituted benzyl, CO—$C_1$-$C_4$-alkyl, optionally substituted benzoyl, $SO_2$—$C_1$-$C_4$-alkyl or in the aryl moiety optionally substituted $SO_2$-aryl.

8. The compound according to claim 1, wherein the given moieties have the following definitions:
A: OH, F, Cl, $OCF_3$, $OCHF_2$, optionally substituted $C_1$-$C_4$-alkyl, O—$C_1$-$C_4$-alkyl or S—$C_1$-$C_4$-alkyl;
B: hydrogen, OH, F, Cl, $CF_3$, $OCF_3$, $OCHF_2$, optionally substituted $C_1$-$C_4$-alkyl, O—$C_1$-$C_4$-alkyl or S—$C_1$-$C_4$-alkyl;
$R_W^1$: hydrogen, F, Cl, CN, $CF_3$ or O—$CF_3$;
$R^1$, $R^2$, $R^3$ independently of one another:
hydrogen, OH, O-methyl, O-phenyl, acetyl, benzoyl, O-acetyl, or O-benzoyl;

Q is

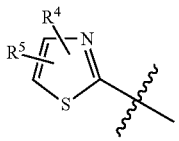

$R_Q^1$: hydrogen, $CH_3$, phenyl, benzyl, methanesulfonyl, phenylsulfonyl or tosyl.

9. The compound according to claim 1, wherein the given moieties have the following definitions:
A: OH, $OCF_3$, $OCH_3$, O-ethyl, O-propyl or O-i-propyl;
Z: —$CH_2$—, —$CH_2$—O—, —$CH_2$—$CH_2$— or —$CH_2$—$CH_2$—O—;
two of the moieties $R^1$, $R^2$, or $R^3$ are hydrogen, and the third moiety is hydrogen, OH, acetyl or benzoyl;

Q:

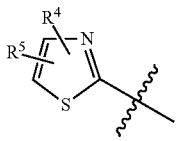

$R_Q^1$: hydrogen, $CH_3$, phenyl, benzyl, methanesulfonyl, phenylsulfonyl or tosyl.

10. Guanidine compound according to claim 1, wherein $R^4$ and/or $R^5$ each independently from one another represent a moiety chosen from the groups 1), 2), 3), 4), 5) or 6):

1) hydrogen, F, Cl, CN, $CF_3$, or
each optionally substituted $C_1$-$C_6$-alkyl, $C_2$-$C_6$-alkenyl, $C_1$-$C_6$-alkylene-O—$C_1$-$C_6$-alkyl or $C_3$-$C_7$-cycloalkyl;

2) Phenyl or naphthyl, which are each substituted with $R_Q^2$, $R_Q^3$, and $R_Q^4$, wherein
$R_Q^2$, $R_Q^3$, and $R_Q^4$ each independently of one another represent a substituent from the following group:
hydrogen, CN, $CF_3$, $CHF_2$, $OCF_3$, $OCHF_2$, F, Cl, OH or each optionally substituted phenyl or hetaryl, $C_1$-$C_4$-alkyl, $C_5$-$C_7$-cycloalkyl, O—$R_Q^5$, $NR_Q^7R_Q^8$, CO—$OR_Q^6$, $NR_Q^8$—CO—O—$R_Q^6$, O—$CH_2$—COO—$R_Q^6$, $NR_Q^8$—CO—$R_Q^6$, $SO_2$—$R_Q^6$, $NR_Q^8$—$SO_2$—$R_Q^6$, $NR_Q^8$—CO—O—$R_Q^6$, $SO_2NH_2$, $CONH_2$, $SO_2$—$NR_Q^7R_Q^8$ or CO—$NR_Q^7R_Q^8$;

$R_Q^5$: $C_1$-$C_4$-alkyl, which is optionally substituted with a substituent from the group consisting of F, Cl, OH, CN, $CF_3$, $OCF_3$, NH—($C_1$-$C_4$-alkyl) and N($C_1$-$C_4$-alkyl)$_2$;

$R_Q^6$: each optionally substituted $C_1$-$C_6$-alkyl, aryl, hetaryl or phenyl;

$R_Q^7$, hydrogen, each optionally substituted $C_1$-$C_4$-alkyl, allyl, aryl, hetaryl, benzyl, phenethyl or $CH_2$-hetaryl;

$R_Q^8$, hydrogen, each optionally substituted $C_1$-$C_4$-alkyl, allyl, aryl, hetaryl, benzyl, phenethyl or $CH_2$-hetaryl;

or $R_Q^7$ and $R_Q^8$ form an optionally substituted 3- or 7-membered saturated or unsaturated ring, which can contain up to two identical or different heteroatoms from the group O and N;

3) benzothiophenyl, benzofuranyl, quinolinyl and isoquinolinyl;

4) both moieties $R^4$ and $R^5$ together form one of the following rings:

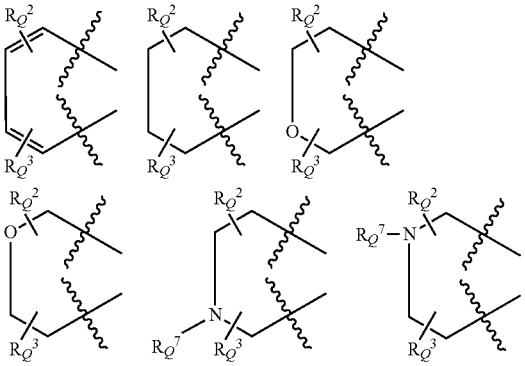

wherein $R_Q^2$ and $R_Q^3$ are defined as under 2); or together can form an anellated 5- or 6-membered ring;

5) adamantyl;

6) each optionally substituted azetidine-3-yl, pyrrolidine-2-yl, pyrrolidine-3-yl, piperidine-2-yl, piperidine-3-yl, piperidine-4-yl, tetrahydro-2H-pyrane-4-yl, tetrahydrofuran-3-yl, azepan-4-yl, azepan-3-yl, azepan-2-yl, 1,4-diazepane-5-yl, 1,2,3,6-tetrahydropyridine-4-yl, or 2,5-dihydro-1H-pyrrol-3-yl.

11. The compound according to claim 1, wherein one moiety from $R^4$ and $R^5$ is chosen from group 1), and the other moiety from $R^4$ and $R^5$ is chosen from the group 1), 2) or 3).

12. A pharmaceutical composition, comprising at least one guanidine compound according to claim 1, as well as a pharmaceutically acceptable carrier or dilution agent.

\* \* \* \* \*